(12) United States Patent
Tchao et al.

(10) Patent No.: US 8,585,555 B2
(45) Date of Patent: *Nov. 19, 2013

(54) INTERACTIVE ATHLETIC EQUIPMENT SYSTEM

(75) Inventors: Michael Tchao, Portland, OR (US); Christopher A. Robinette, Lake Oswego, OR (US); Jason Nims, Portland, OR (US)

(73) Assignee: Nike, Inc., Beaverton, OR (US)

( * ) Notice: Subject to any disclaimer, the term of this patent is extended or adjusted under 35 U.S.C. 154(b) by 48 days.

This patent is subject to a terminal disclaimer.

(21) Appl. No.: 13/334,781

(22) Filed: Dec. 22, 2011

(65) Prior Publication Data

US 2012/0095578 A1     Apr. 19, 2012

Related U.S. Application Data

(63) Continuation of application No. 12/397,061, filed on Mar. 3, 2009, now Pat. No. 8,088,044.

(60) Provisional application No. 61/033,355, filed on Mar. 3, 2008.

(51) Int. Cl.
*A63B 71/00*     (2006.01)

(52) U.S. Cl.
USPC .................................................... 482/8

(58) Field of Classification Search
USPC ................. 482/1–9, 901–902; 434/247, 255; 700/91–92; 705/2–3
IPC ....................................................... A63B 71/00
See application file for complete search history.

(56) References Cited

U.S. PATENT DOCUMENTS

| | | | |
|---|---|---|---|
| 5,149,084 A | 9/1992 | Dalebout et al. | |
| 7,670,263 B2 * | 3/2010 | Ellis et al. | 482/8 |
| 7,927,253 B2 | 4/2011 | Vincent et al. | |
| 8,221,290 B2 | 7/2012 | Vincent et al. | |
| 2006/0025282 A1 | 2/2006 | Redmann | |
| 2006/0205569 A1 * | 9/2006 | Watterson et al. | 482/54 |
| 2007/0156335 A1 * | 7/2007 | McBride et al. | 701/209 |
| 2008/0274755 A1 | 11/2008 | Cholkar et al. | |
| 2009/0048070 A1 * | 2/2009 | Vincent et al. | 482/8 |
| 2009/0048918 A1 | 2/2009 | Dawson et al. | |
| 2009/0050699 A1 | 2/2009 | Basar et al. | |
| 2009/0233770 A1 | 9/2009 | Vincent et al. | |
| 2012/0277040 A1 | 11/2012 | Vincent et al. | |

FOREIGN PATENT DOCUMENTS

CN     101367011 A     2/2009

OTHER PUBLICATIONS

The First Office Action for Chinese patent application No. 200980109267.1 issued Sep. 3, 2012.
International Preliminary Report on Patentability for International Application No. PCT/US2009/035877, mailed Sep. 16, 2010, 7 pages.

(Continued)

*Primary Examiner* — Oren Ginsberg
(74) *Attorney, Agent, or Firm* — Banner & Witcoff, Ltd

(57) ABSTRACT

Systems and techniques for the collection and display of athletic information. Athletic data relating to a single person or group of people is collected at a central location, and subsequently displayed at a desired remote location so that the person or people can review and critique their performance. In addition, athletic data for multiple persons can be collected at a central location, and subsequently displayed to a user at a desired remote location, so that the user can compare his or her athletic activities to others.

17 Claims, 58 Drawing Sheets

(56) References Cited

OTHER PUBLICATIONS

International Search Report and Written Opinion of International Application No. PCT/US2009/035877, mailed Jul. 2, 2009, 10 pages.

Aug. 29, 2013 Third Office Action issued in Chinese Patent Application No. 200980109267.1.

* cited by examiner

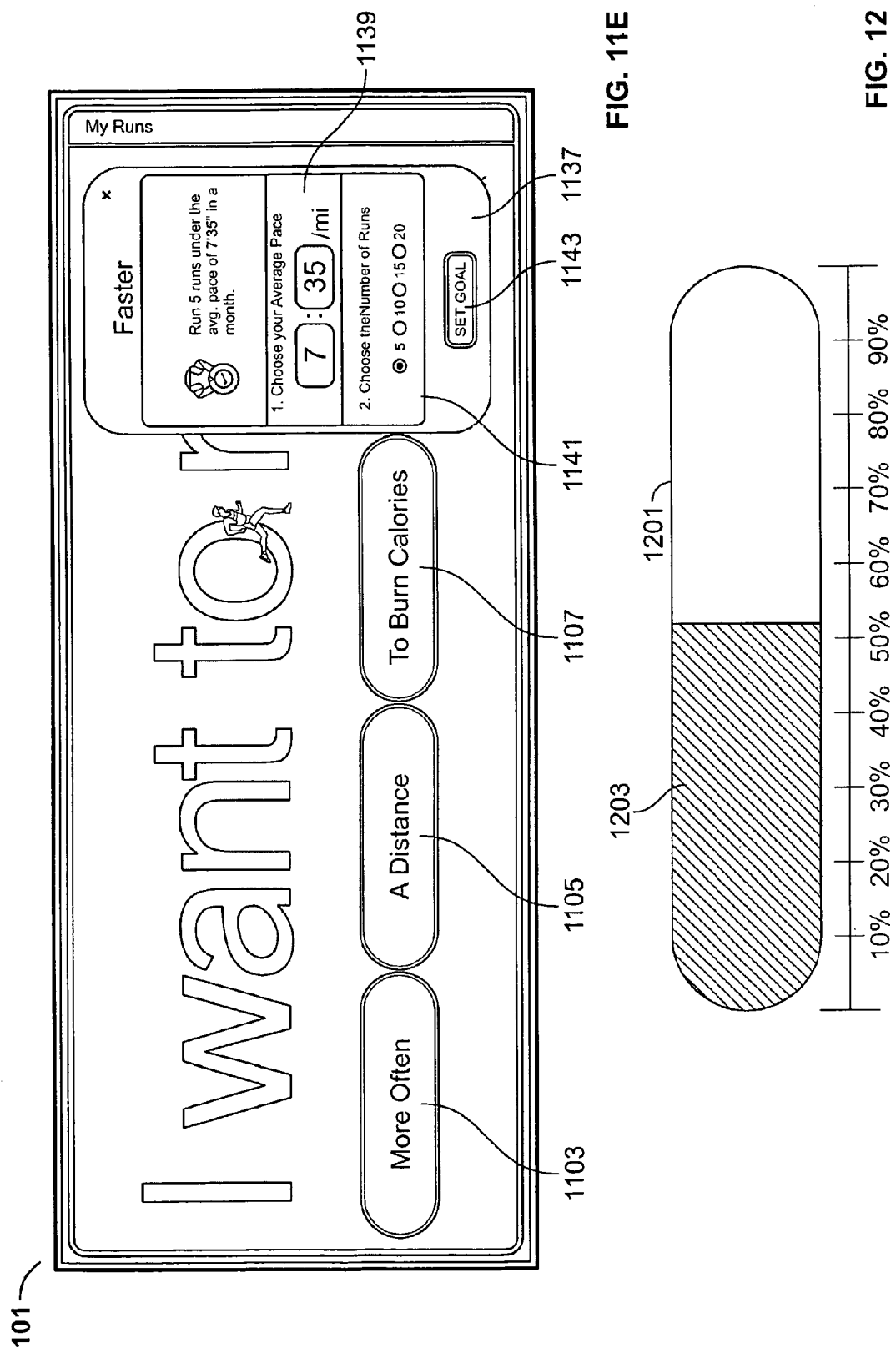

Top 10. Sort By:

| | | |
|---|---|---|
| distance: | ⓐ week | ⓐ month | ⓐ ever |
| duration: | ⓐ week | ⓐ month | ⓐ ever |
| fastest 5k: | ⓐ week | ⓐ month | ⓐ ever |
| fastest 10k: | ⓐ week | ⓐ month | ⓐ ever |

Last week's totals were calculated on Sunday at midnight GMT. Last month's totals were calculated on the last day of the month at midnight GMT.

Events | Run World | Leaderboard

GENDER: ALL ▼ | AGE: ALL ▼ | GEO: ALL ▼

| 1 | HAYABUSA KAZ | 209.36 mi |
| 2 | Chuck Jonard | 130.84 mi |
| 3 | slinki | 96.28 mi |
| 4 | angekar | 83.42 mi |
| 5 | Salep | 82.13 mi |
| 6 | filo66go | 81.02 mi |
| 7 | JeSquared | 80.13 mi |
| 8 | Ngster | 77.7 mi |
| 9 | ひびきん | 77.59 mi |
| 10 | PreLives13 | 77.14 mi |

| 2932 | Rauchholz | 20.25 mi |

Community

FIG. 14A

| | Events | Run World | Leaderboard |
|---|---|---|---|
| | GENDER: ALL ▸ | AGE: ALL ▸ | GEO: ALL ▸ |
| 1 | Chuck Jonard | | 203:32'21" |
| 2 | nikeclubrunsf | | 141:44'42" |
| 3 | Run'n4Cancer | | 109:00'17" |
| 4 | HAYABUSA KAZ | | 99:04'36" |
| 5 | shin0073 | | 91:18'44" |
| 6 | JSD | | 87:40'07" |
| 7 | shimizuhi | | 73:08'49" |
| 8 | しん+ | | 70:38'27" |
| 9 | alfredrennt | | 67:49'49" |
| 10 | lorraine | | 63:50'44" |
| 28636 | Rauchholz | | 1:47'34" |

Top 10. Sort By:

distance: ⊙ week | ⊙ month | ⊙ ever
duration: ⊙ week | ⊙ month | ⊙ ever
fastest 5k: ⊙ week | ⊙ month | ⊙ ever
fastest 10k: ⊙ week | ⊙ month | ⊙ ever Last week's totals were calculated on Sunday at midnight GMT. Last month's totals were calculated on the last day of the month at midnight GMT.

Community

FIG. 14B

| | | |
|---|---|---|
| Events | Run World | Leaderboard |

GENDER: ALL / m / f  AGE: ALL ▼  GEO: ALL ▼

| | | |
|---|---|---|
| 1 | USA KAZ | 209.36 mi |
| 2 | Chuck Jonard | 104.3 mi |
| 3 | Inkus | 101.79 mi |
| 4 | slinki | 96.28 mi |
| 5 | Salep | 84.48 mi |
| 6 | omar123 | 81.6 mi |
| 7 | angekar | 78.63 mi |
| 8 | Ngster | 77.7 mi |
| 9 | JSD | 75.81 mi |
| 10 | vincentc2 | 75.28 mi |
| 2111 | Rauchholz | 20:25 mi |

🌐 Top 10. Sort By:

distance: ⊙ week | ⊙ month | ⊙ ever
duration: ⊙ week | ⊙ month | ⊙ ever
fastest 5k: ⊙ week | ⊙ month | ⊙ ever
fastest 10k: ⊙ week | ⊙ month | ⊙ ever Last week's totals were calculated on Sunday at midnight GMT. Last month's totals were calculated on the last day of the month at midnight GMT.

Community

INTERACTIVE ATHLETIC EQUIPMENT SYSTEM

CROSS-REFERENCE TO RELATED APPLICATIONS

The present application is a continuation of co-pending U.S. application Ser. No. 12/397,061, entitled "INTERACTIVE ATHLETIC EQUIPMENT SYSTEM," and filed on Mar. 3, 2009, which is a continuation-in-part of and claims the benefit of and priority to U.S. Patent Application No. 61/033,355 filed on Mar. 3, 2008. The contents of the above noted applications are hereby incorporated by reference in their entirety and made a part hereof.

FIELD OF THE INVENTION

The present invention relates to the collection and display of athletic information. Some aspects of the invention have particular applicability to the collection of athletic information over a network, and displaying the collected information.

BACKGROUND OF THE INVENTION

While most people appreciate the importance of physical fitness, many have difficulty finding the motivation required to maintain a regular exercise program. Some people find it particularly difficult to maintain an exercise regimen that involves continuously repetitive motions, such as running, walking and bicycling.

Experienced athletes and trainers have found that feedback provides many people with motivation to maintain a regular exercise program. When a person can directly experience the results provided by an exercise program, that person typically will be encouraged to continue exercising. Unfortunately, the physical improvements obtained from exercise often come too slowly to provide sufficient motivation for many people to maintain a regular exercise program. It would therefore be useful for many athletes to have a more immediate, visual type of feedback to provide motivation for regular exercise.

Many experienced athletes and trainers also have found that competition may provide an even stronger motivation to maintain a regular exercise program. Some athletes, for example, will be more motivated to exercise when competing against a partner than by exercising alone. These athletes may, for example, exercise with a partner, enter into athletic contests such as races, or even just compare their current performance ability with a friend's.

BRIEF SUMMARY OF THE INVENTION

Various aspects of the invention relate to the collection and display of athletic information. With some implementations of the invention, athletic data relating to a single person is collected and displayed so that the person can fully critique his or her performance. For example, a set of athletic data corresponding to athletic activity performed by a person over a first time period may be displayed as a graph. If the set of athletic data is generated from, e.g., a person running or walking, then the person's speed may be plotted against his or her distance over the time period for the activity. With some implementations, the set of athletic data can be analyzed, and the analysis results can be displayed simultaneously with the graph. For example, with a set of athletic data obtained from a person running, the data can be analyzed to determine the change in speed (i.e., acceleration or deceleration) between fixed distances (first mile, second mile, etc.). This information can then be displayed with the graph, so that the person can review when and how much he or she changed speed during the run.

With still other implementations of the invention, a person can compare a set of athletic data with another set of athletic data having a desired characteristic. For example, if a selected set of athletic data is generated from, e.g., a person running over a particular time period, then the person may wish to compare his or her performance for that "run" with his or her best speed for a similar previous run. Thus, if the run covered a distance of, e.g., 4 miles, earlier sets of athletic data will be analyzed to determine which data sets correspond to runs of approximately 4 miles. The data set having, e.g., the highest mean speed can then be identified, and data from that previously data set displayed simultaneously with data from the selected data set. For example, data from each athletic data set may be plotted as graph and rendered on a display. The person can then compare the selected set of athletic data with the set of athletic data representing his or her "best" speed in detail.

Still further, some implementations may collect sets of athletic data obtained over different time periods, and concurrently display data from these sets. Thus, if a person has multiple runs over a period of days, data from each run may be simultaneously displayed. For example, an icon, such as a bar or line, can be displayed for each data set. A dimension of the icon, such as, e.g., its height, can then correspond to some data in that data set, such as the median speed of the run or the total distance traveled over the run. With some implementations, data from multiple sets may be aggregated and displayed. For examples, runs falling within a specified category (e.g., occurring during the same week or month) can be grouped together, and the total distance data (or, alternatively, the total time data) for each data set in a group can be added together. An icon, such as a bar or line, then can be displayed to represent the sum of the data from each group. A dimension of the icon, such as, e.g., its height, may correspond to the data added together from its corresponding group of data sets.

In addition, some examples of the invention may allow a person to specify a goal related to an athletic activity. A person may, e.g., set a goal of running a specified total distance within a specified period of time. With these implementations of the invention, data from multiple sets of a person's athletic data may be aggregated and displayed in contrast with the person's specified goal. The goal may be displayed, for example, as an empty shape, like an oval. The aggregated data may then be displayed as fill within the empty shape. Thus, if the aggregated data shows that the person is within 80% of his or her goal, then the shape representing the goal will be displayed as 80% filled.

With some implementations, sets of athletic data may be obtained from a plurality of different persons and displayed. For example, one or more sets of data from each of a plurality of different persons may be collected. Data from each person's data sets can then be aggregated and displayed to each person. For example, a set of athletic data can be generated for each run a person makes. For each person, data from his or her data sets, such as distance data, can be added up. An icon, such as a bar or line, can then be displayed for each person to represent the sum of the data from his or her data sets. A dimension of the icon, such as, e.g., its height, may correspond to the sum of the data added from each of a person's data sets.

Still further, some examples of the invention may allow a person to "invite" one or more other persons to share athletic data corresponding to their athletic activities. With some implementations of the invention, for example, a user may send an invitation via electronic mail or a similar electronic medium to one or more other persons. Athletic data from only those invited persons may then be displayed simultaneously as noted above. This arrangement allows each invited person (including the inviting host, who inherently invites himself or herself and thus is considered an invitee as well) to compare his or her current athletic data with the other invitees.

With still other implementations of the invention, a person may alternately or additional specify a common goal for the invitees. For example, the inviting host may specify a total combined distance that the invitees (including the host) are to run within a specified amount of time. Data from multiple sets of athletic data for each invitee may be aggregated and displayed in contrast with the person's specified goal. Again, the goal may be represented by the display of, for example, an empty shape, like an oval. The data aggregated from each invitee may then be displayed as fill within the empty shape. Thus, if the aggregated data shows that the collective athletic activity of the invitees is within 60% of the specified goal, then the shape representing the goal will be displayed as 60% filled.

For yet other implementations of the invention, the performance data collected from one or more users or athletes may be collected by an athletic device or machine and/or displayed on an athletic device or machine console so that the user or athlete may have a substantially real-time display of their performance against personal goals, benchmarks, or milestones. The user or athlete may also have a display of their performance in a competition or challenge.

These and other features of the invention will become apparent from the following detailed description.

BRIEF DESCRIPTION OF THE DRAWINGS

FIGS. 10 and 11A-11E illustrate examples of user interfaces that may be provided to select goals for a user according to various implementations of the invention.

FIG. 12 illustrates an example of a user interface that may be provided to indicate a user's progress toward achieving an athletic activity goal according to various implementations of the invention.

FIGS. 14A-14F illustrate examples of user interfaces that may be provided to compare a user's athletic data with the athletic data of other participating users according to various implementations of the invention.

Figure 23:
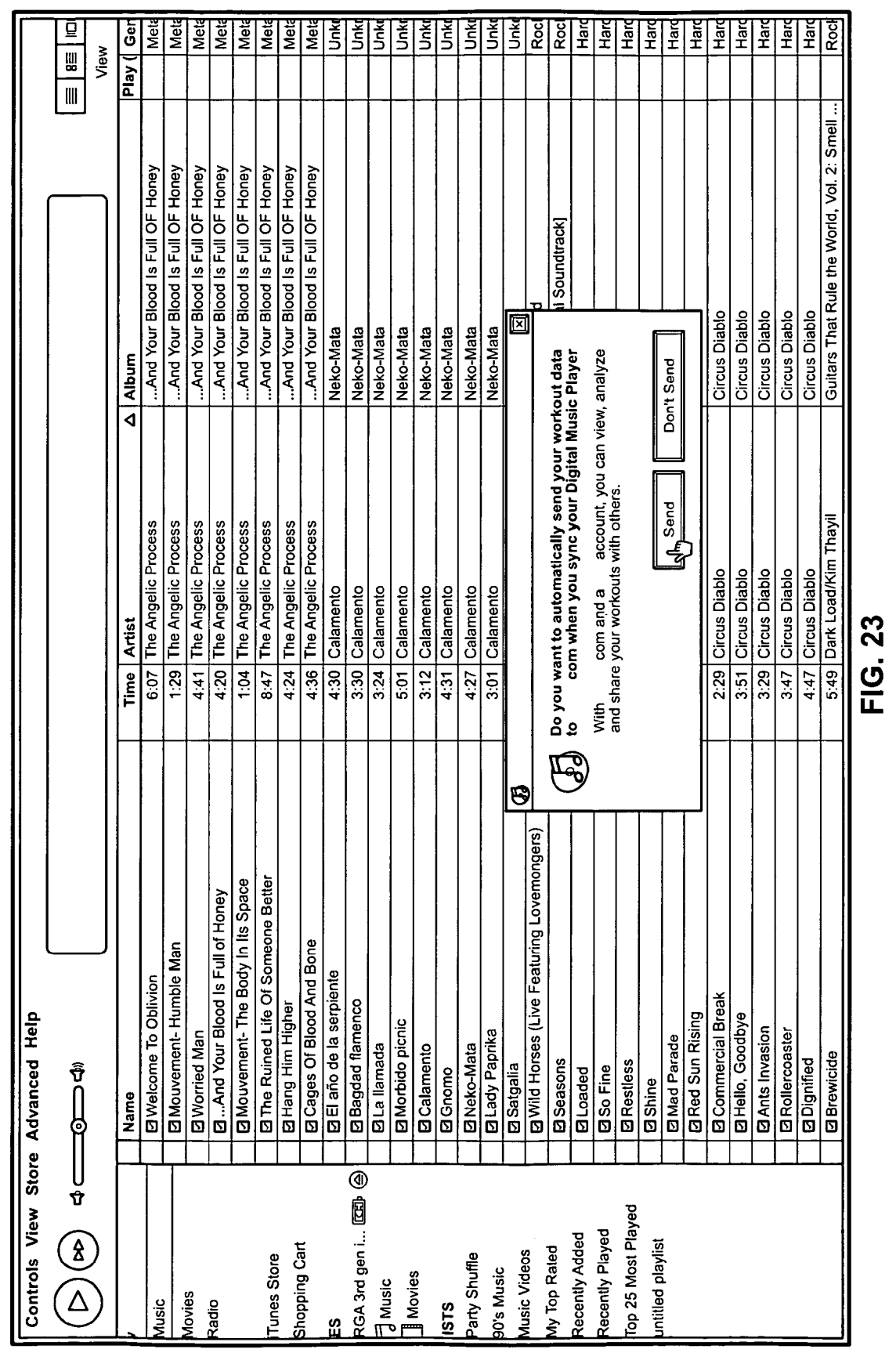

FIG. 23 illustrates an example user interface for configuring data synching between a portable music player and an athletic performance tracking site according to one or more aspects described herein.

FIGS. 24 and 25 illustrate example user interfaces for graphically illustrating a user's workout according to one or more aspects described herein.

FIG. 26 illustrates an example user interface showing a user's past workouts in both a common unit and an athletic activity specific unit according to one or more aspects described herein.

FIG. 27 illustrates an example user interface providing additional workout information upon hovering over one of the past workout bars according to one or more aspects described herein.

FIG. 29 illustrates an example user interface showing only workouts recorded or stored in a common unit according to one or more aspects described herein.

FIG. 31 illustrates an example user interface providing an option for a user to view goals according to one or more aspects described herein.

FIG. 32 illustrates an example user interface showing a user's goal and the user's current progress in reaching the goal according to one or more aspects described herein.

FIG. 33 illustrates an example user interface providing an option for a user to view challenges according to one or more aspects described herein.

Figure 34:
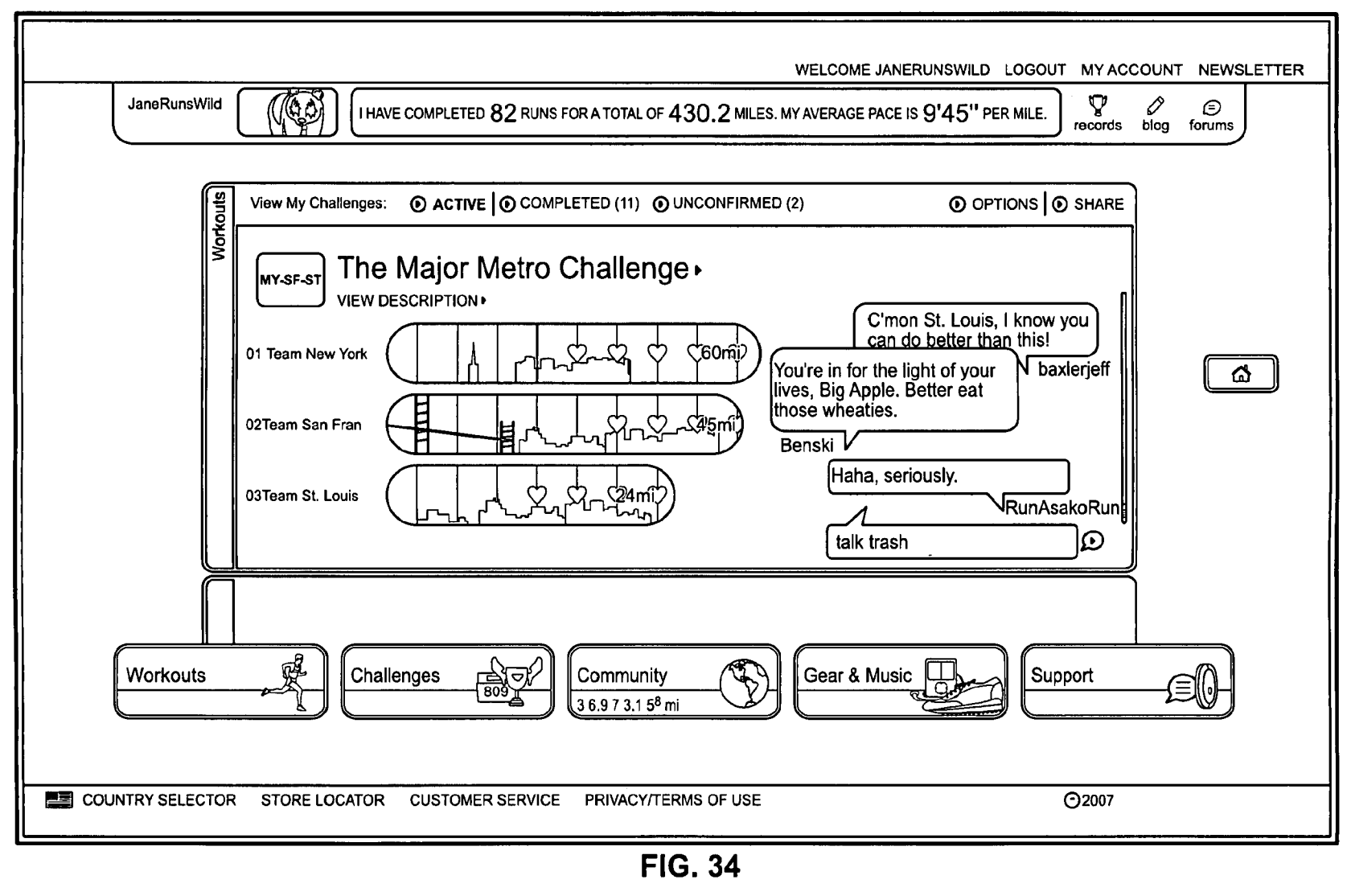

FIGS. 34, 35, 36 and 37 illustrate example user interfaces showing various challenges in which a user is participating according to one or more aspects described herein.

FIG. 39 illustrates an example user interface that tracks and displays a progress of a user in completing a training program according to one or more aspects described herein.

DETAILED DESCRIPTION OF THE INVENTION

Operating Environment

Overview

Figure 1:
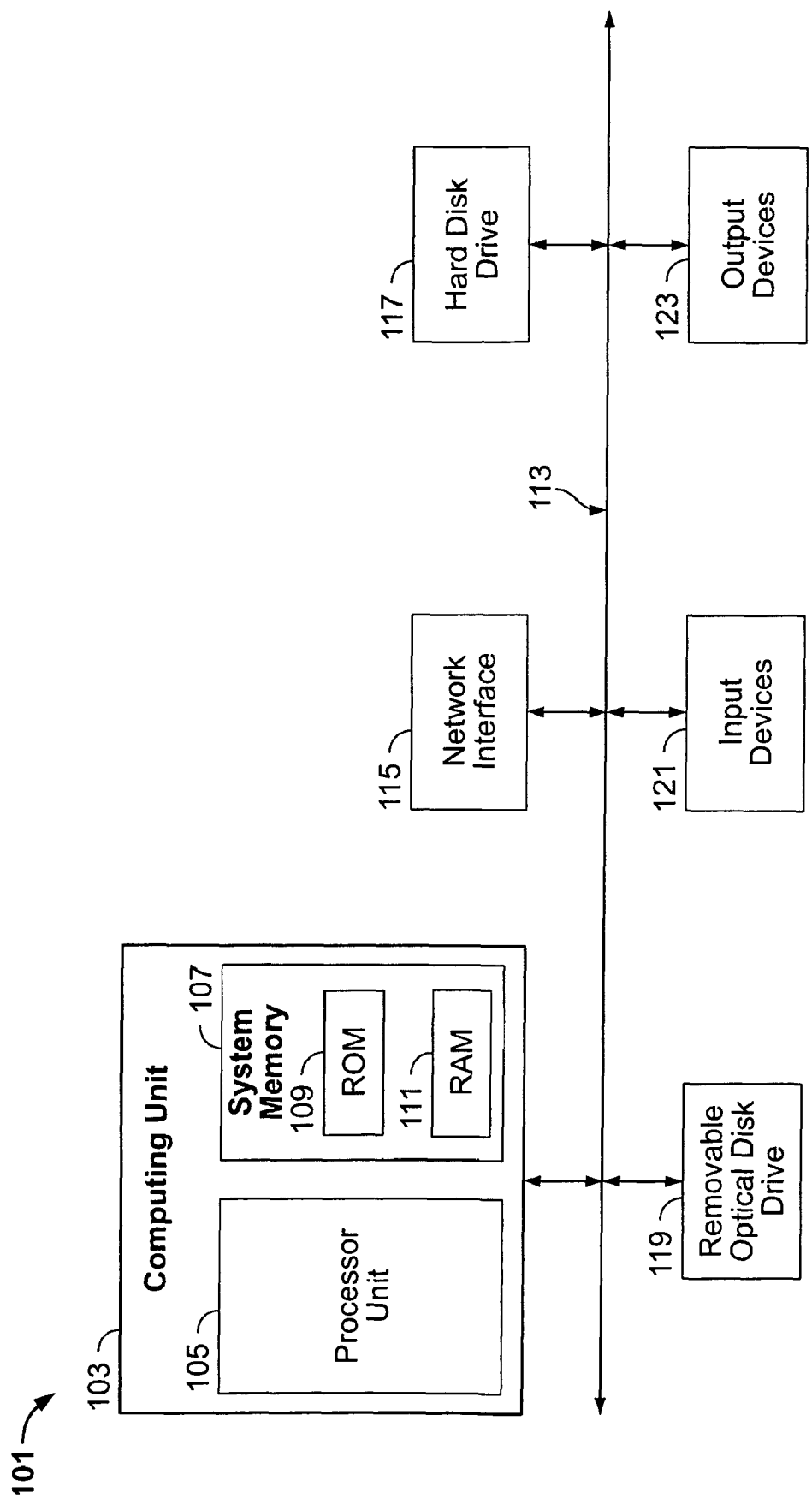
FIG. 1 illustrates a computing device that may be used to implement various examples of the invention.

Aspects of the invention relate to the measurement, collection and display of athletic information. As will be appreciated by those of ordinary skill in the art, athletic information must first be obtained from an individual person. With various implementations of the invention, one or more different athletic information monitoring devices may be used to measure and record athletic data corresponding to athletic activity performed by a person. Typically, an athletic information monitoring device will incorporate a sensor for measuring parameters relating to the person being monitored, and a computing device for processing the parameters measured by the sensor.

Once an athletic information monitoring device has recorded athletic information for a person's athletic activity, the person may then transfer the recorded athletic information to one or more separate devices, in order to view the recorded athletic data. A user may, for example, download the recorded athletic information from an athletic information monitoring device to a separate collection device. The collection device may, in turn, transfer the athletic information collected from the athletic information monitoring device to a separate display configuration device, where the athletic information can be organized and configured for subsequent viewing with, e.g., still another device. As will be discussed in more detail below, various implementations of the invention will allow a person to record, collect and display athletic information using a group of computing devices communicating over a network, such as the Internet.

For example, some implementations of the invention may allow a person to measure and record athletic information using a special-purpose computing device. The user can then transfer the recorded athletic information to a local computing device, such as a personal desktop or laptop computer. More particularly, a user can download recorded athletic information from the athletic information monitoring device to a collection software tool on a local computer that acts as a "client" in a computer network. The collection software tool will then transfer the downloaded athletic information through the network to a remote "server" computer. A display configuration software tool on the remote server computer will then save the transferred athletic information. Later, a person can use the client computer or another local computer to retrieve the stored athletic information from the server computer. In response to a display request from a local computer, the display configuration software tool will configure the requested athletic information for display on the local computer, and then transmit the configured athletic information to the local computer for display.

Computing Device

Various examples of the invention may be implemented using electronic circuitry configured to perform one or more functions. For example, with some embodiments of the invention, the athletic information monitoring device, the collection device, the display device or any combination thereof may be implemented using one or more application-specific integrated circuits (ASICs). More typically, however, components of various examples of the invention will be implemented using a programmable computing device executing firmware or software instructions, or by some combination of purpose-specific electronic circuitry and firmware or software instructions executing on a programmable computing device.

Accordingly, FIG. 1 shows one illustrative example of a computer 101 that can be used to implement various embodiments of the invention. As seen in this figure, the computer 101 has a computing unit 103. The computing unit 103 typically includes a processing unit 105 and a system memory 107. The processing unit 105 may be any type of processing device for executing software instructions, but will conventionally be a microprocessor device. The system memory 107 may include both a read-only memory (ROM) 109 and a random access memory (RAM) 111. As will be appreciated by those of ordinary skill in the art, both the read-only memory (ROM) 109 and the random access memory (RAM) 111 may store software instructions for execution by the processing unit 105.

The processing unit 105 and the system memory 107 are connected, either directly or indirectly, through a bus 113 or alternate communication structure to one or more peripheral devices. For example, the processing unit 105 or the system memory 107 may be directly or indirectly connected to additional memory storage, such as the hard disk drive 115, the removable magnetic disk drive 117, the optical disk drive 119, and the flash memory card 121. The processing unit 105 and the system memory 107 also may be directly or indirectly connected to one or more input devices 123 and one or more output devices 125. The input devices 123 may include, for example, a keyboard, touch screen, a remote control pad, a pointing device (such as a mouse, touchpad, stylus, trackball, or joystick), a scanner, a camera or a microphone. The output devices 125 may include, for example, a monitor display, television, printer, stereo, or speakers.

Still further, the computing unit 103 will be directly or indirectly connected to one or more network interfaces 127 for communicating with a network. This type of network interface 127, also sometimes referred to as a network adapter or network interface card (NIC), translates data and control signals from the computing unit 103 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 127 may employ any suitable connection agent for connecting to a network, including, for example, a wireless transceiver, a power line adapter, a modem, or an Ethernet connection.

It should be appreciated that, in addition to the input, output and storage peripheral devices specifically listed above, the computing device may be connected to a variety of other peripheral devices, including some that may perform input, output and storage functions, or some combination thereof. For example, the computer 101 may be connected to a digital music player, such as an IPOD® brand digital music player available from Apple, Inc. of Cupertino, Calif. As known in the art, this type of digital music player can server as both an output device for a computer (e.g., outputting music from a sound file or pictures from an image file) and a storage device. In addition, this type of digital music play also can serve as an input device for inputting recorded athletic information, as will be discussed in more detail below.

In addition to a digital music player, the computer 101 may be connected to or otherwise include one or more other peripheral devices, such as a telephone. The telephone may be, for example, a wireless "smart phone." As known in the art, this type of telephone communicates through a wireless network using radio frequency transmissions. In addition to simple communication functionality, a "smart phone" may also provide a user with one or more data management functions, such as sending, receiving and viewing electronic messages (e.g., electronic mail messages, SMS text messages, etc.), recording or playing back sound files, recording or playing back image files (e.g., still picture or moving video image files), viewing and editing files with text (e.g., Microsoft Word or Excel files, or Adobe Acrobat files), etc. Because of the data management capability of this type of telephone, a user may connect the telephone with the computer 101 so that their data maintained may be synchronized.

Of course, still other peripheral devices may be included with our otherwise connected to a computer 101 of the type illustrated in FIG. 1, as is well known in the art. In some cases, a peripheral device may be permanently or semi-permanently connected to the computing unit 103. For example, with many computers, the computing unit 103, the hard disk drive 117, the removable optical disk drive 119 and a display are semi-permanently encased in a single housing. Still other peripheral devices may be removably connected to the computer 101, however. The computer 101 may include, for example, one or more communication ports through which a peripheral device can be connected to the computing unit 103 (either directly or indirectly through the bus 113). These communication ports may thus include a parallel bus port or a serial bus port, such as a serial bus port using the Universal Serial Bus (USB) standard or the IEEE 1394 High Speed Serial Bus standard (e.g., a Firewire port). Alternately or additionally, the computer 101 may include a wireless data "port," such as a Bluetooth interface, a Wi-Fi interface, an infrared data port, or the like.

It should be appreciated that a computing device employed according various examples of the invention may include more components than the computer 101 illustrated in FIG. 1, fewer components than the computer 101, or a different combination of components than the computer 101. Some implementations of the invention, for example, may employ one or more computing devices that are intended to have a very specific functionality, such as a digital music player or server computer. These computing devices may thus omit unnecessary peripherals, such as the network interface 115, removable optical disk drive 119, printers, scanners, external hard drives, etc. Some implementations of the invention may alternately or additionally employ computing devices that are intended to be capable of a wide variety of functions, such as a desktop or laptop personal computer. These computing devices may have any combination of peripheral devices or additional components as desired.

Athletic Information Monitoring Device

Figure 2:
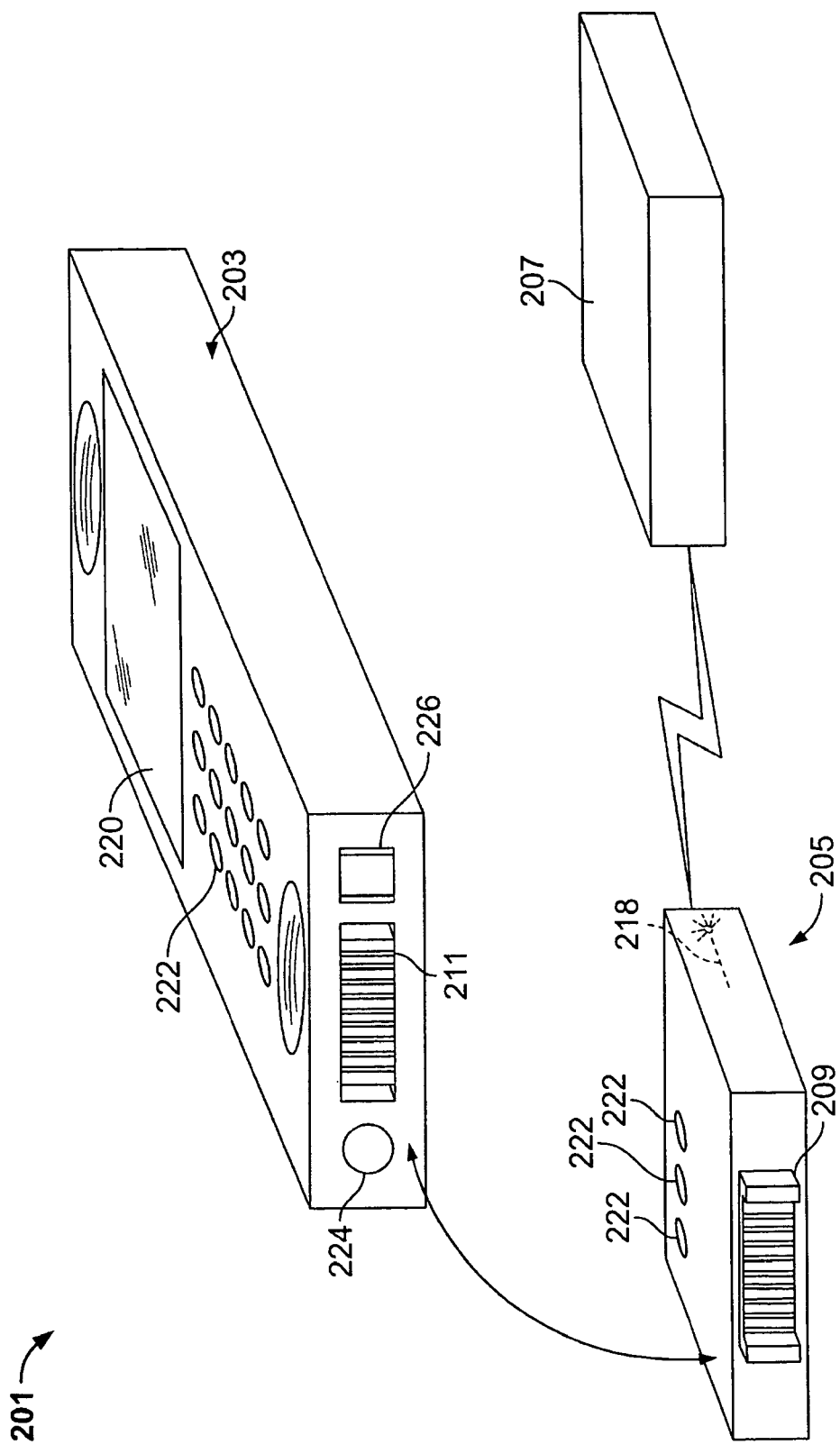
FIGS. 2 and 3 illustrate an example of an athletic information monitoring device that may be employed according to various examples of the invention.

FIG. 2 illustrates one example of an athletic information monitoring device 201 that may be employed according to various examples of the invention to measure athletic information corresponding a user's athletic activity. As shown in this figure, the athletic information monitoring device 201 includes a digital music player 203, an electronic interface device 205, and an athletic parameter measurement device 207. As will be described in more detail, the digital music player 203 is (releasably) connected to the electronic interface device 205, and the combination is worn or otherwise carried by the user while he or she is performing an athletic activity, such as running or walking. The athletic parameter measurement device 207 also is worn or carried by the user while he or she is performing an athletic activity, and measures one or more athletic parameters relating to the athletic performance being performed by the user. The athletic parameter measurement device 207 transmits signals to the electronic interface device 205 that correspond to the measured athletic parameter. The electronic interface device 205 receives the signals from the athletic parameter measurement device 207, and provides the received information to the digital music player 203.

Figure 3:
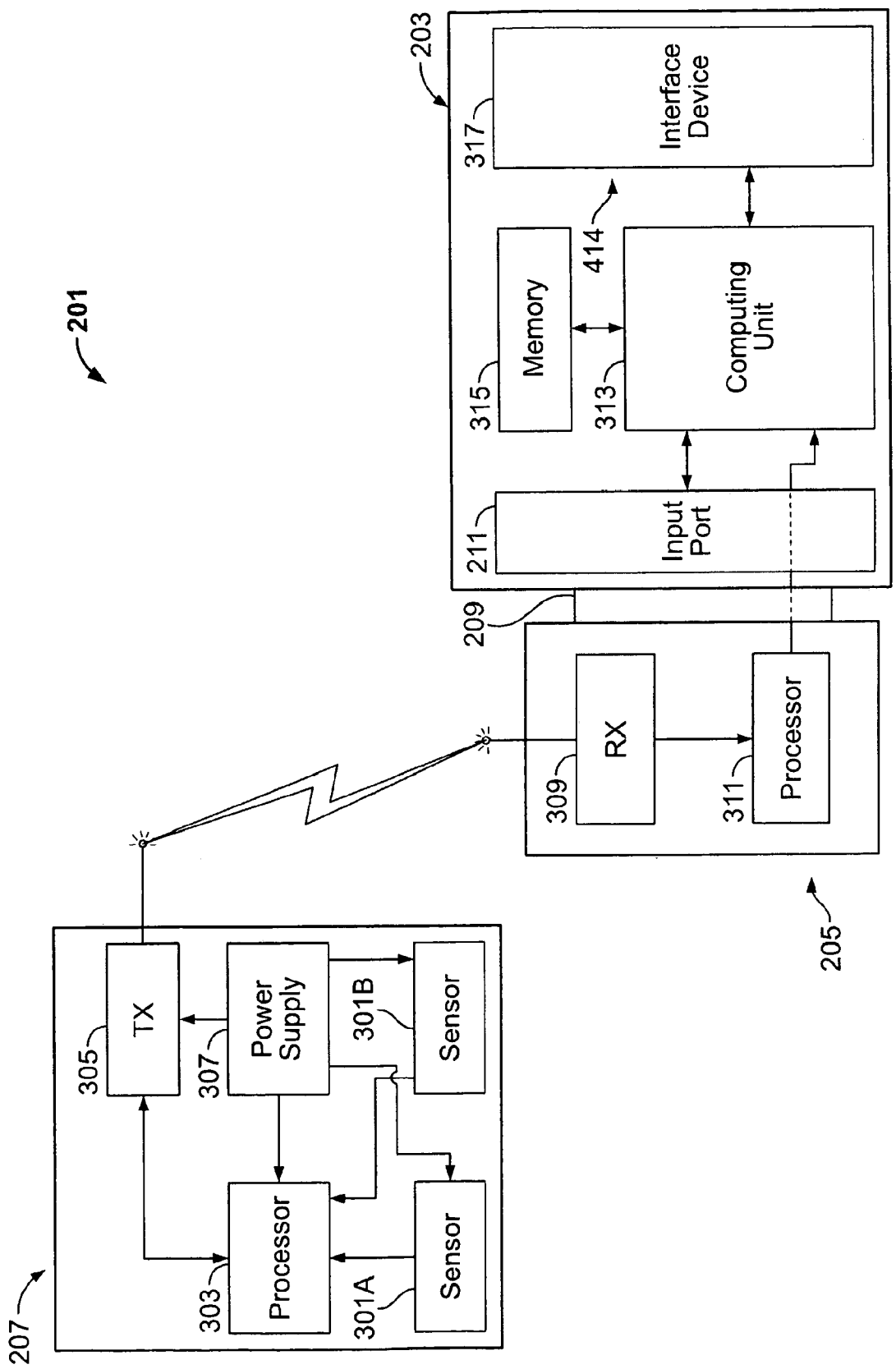
Figure 4:
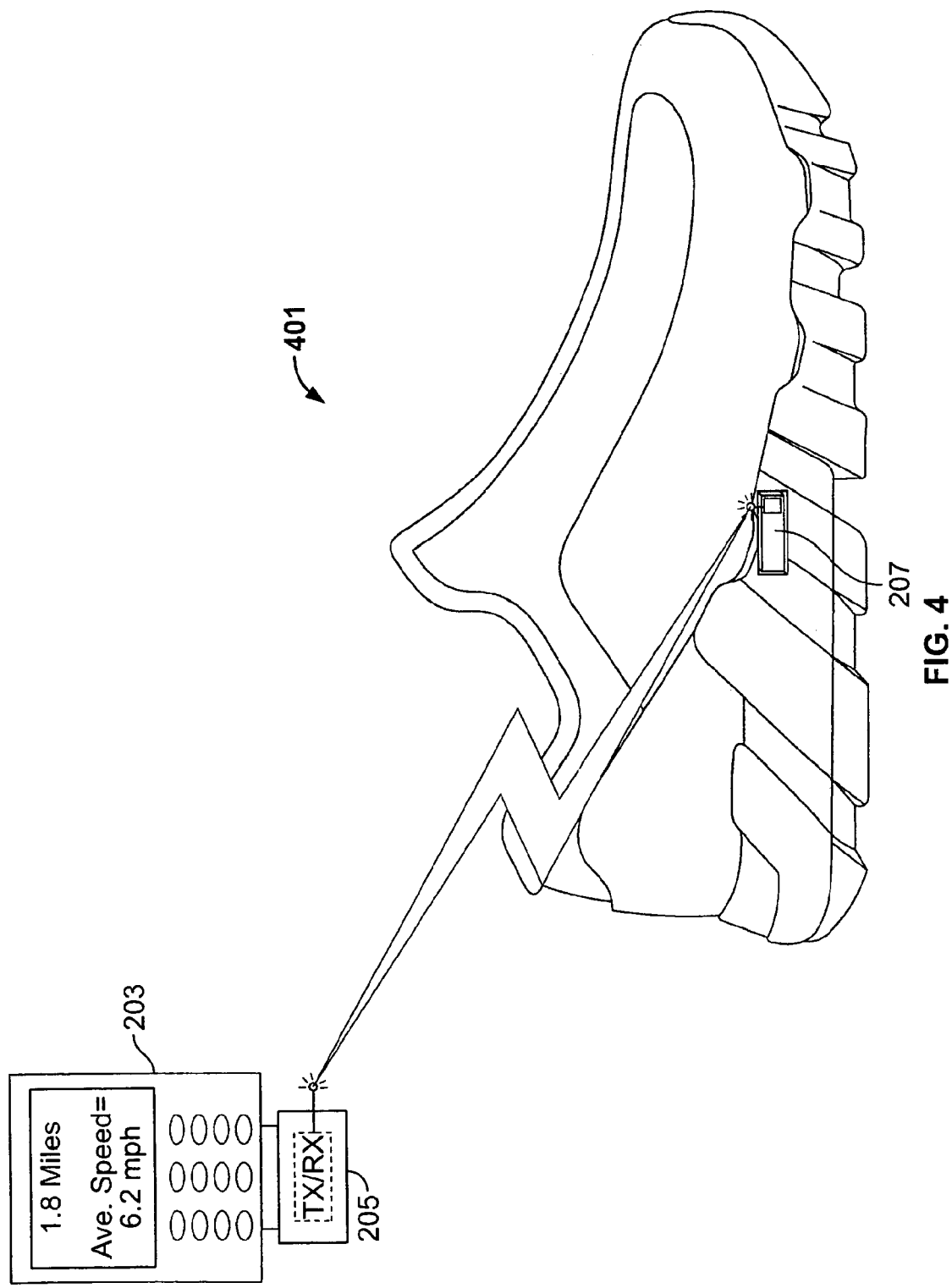
FIG. 4 illustrates one environment in which an athletic parameter measurement device according to various examples of the invention may be employed.

As shown in more detail in FIG. 3, the athletic parameter measurement device 207 includes one or more sensors 301 for measuring an athletic parameter associated with a person wearing or otherwise using the athletic parameter measurement device 207. With the illustrated implementations, for example, the sensors 301A and 301B may be accelerometers (such as piezoelectric accelerometers) for measuring the acceleration of the athletic parameter measurement device 207 in two orthogonal directions. The athletic parameter measurement device 207 is carried or otherwise worn by a user to measure the desired athletic parameter while the user exercises. For example, as shown in FIG. 4, the athletic parameter measurement device 207 may be located the sole of a user's shoe 401 while the user walks or runs. With this arrangement, the sensors 301 will produce electrical signals corresponding to the movement of the user's foot. As known in the art, these signals can then be used to generate athletic data representative of the athletic activity performed by the user.

The athletic parameter measurement device 207 also includes a processor 303 for processing the electrical signals output by the sensors 301. With some implementations of the invention, the processor 303 may be a programmable microprocessor. For still other implementations of the invention, however, the processor 303 may be a purpose-specific circuit device, such as an ASIC. The processor 303 may perform any desired operation on the signals output from the sensors 301, such as curve smoothing, noise filtering, outlier removal, amplification, summation, integration, or the like. The processor 303 provides the processed signals to a transmitter 307. The athletic parameter measurement device 207 also includes a power supply 307, for providing power to the sensors 301, the processor 303, and the transmitter 305 as needed. The power supply 307 may be, for example, a battery.

The athletic parameter measurement device 207 transmits the processed signals to the electronic interface device 205, as seen in FIG. 4. Returning now to FIG. 3, the electronic interface device 205 includes a receiver 309 which receives the processed signals transmitted by the transmitter 305 in the athletic parameter measurement device 207. The receiver 309 relays the processed signals to a second processor 311, which processes the signals further. Like the processor 303, the processor 311 may perform any desired operation on the processed signals, such as curve smoothing, noise filtering, outlier removal, amplification, summation, integration, or the like.

The processor 303 provides the processed signals to the digital music player 203. Referring back now to FIG. 2, the electronic interface device 205 includes a connector system 209 that physically plugs into and connects with a conventional input port 211 provided on digital music player 203. The input port 211 into which the connector system 209 of the electronic interface device 205 connects may be any desired type of input port for transferring data, such as a parallel data port, a serial data port, an earphone or microphone jack, etc.) The connector system 209 may include any suitable connecting devices, such as wires, pins, electrical connectors, and the like, so as to make an electrical connection or other suitable connection with corresponding elements provided in the input port 211 of the digital music player 203 (e.g., to allow electronic and/or data communications between the interface device 205 and the electronic interface device 205). If necessary or desired, additional securing elements may be provided to securely connect the interface device 205 to the digital music player 203, such as straps, hooks, buckles, clips, clamps, clasps, retaining elements, mechanical connectors, and the like.

Returning now to FIG. 3, the processor 311 provides the processed signals to the computing unit 313. The computing unit 313 may initially store the processed signals in the memory 315. Further, with some implementations of the invention, the computing unit 313 may operate on the processed signals provided by the athletic information monitoring device 201 to generate a set of athletic data corresponding to the athletic activity performed by the user. For example, if the athletic information monitoring device 201 includes accelerometers for measuring the movement of the user's foot, the computing unit 313 may analyze the processed signals from the athletic information monitoring device 201 to generate a set of athletic data describing the user's speed at specific instances during the user's athletic activity and the total distance traveled by the user at each of those specific instances. Various techniques for determining a user's speed from accelerometer signals are described in, for example, U.S. Pat. No. 6,898,550 to Blackadar et al., entitled "Monitoring Activity Of A User In Locomotion On Foot," and issued on May 24, 2005, U.S. Pat. No. 6,882,955 to Ohlenbusch et al., entitled "Monitoring Activity Of A User In Locomotion On Foot," and issued on Apr. 19, 2005, U.S. Pat. No. 6,876,947 to Darley et al., entitled "Monitoring Activity Of A User In Locomotion On Foot," and issued on Apr. 5, 2005, U.S. Pat. No. 6,493,652 to Ohlenbusch et al., entitled "Monitoring Activity Of A User In Locomotion On Foot," and issued on Dec. 10, 2002, U.S. Pat. No. 6,298,314 to Blackadar et al., entitled "Detecting The Starting And Stopping Of Movement Of A Person On Foot," and issued on Oct. 2, 2001, U.S. Pat. No. 6,052,654 to Gaudet et al., entitled "Measuring Foot Contact Time And Foot Loft Time Of A Person In Locomotion," and issued on Apr. 18, 2000, U.S. Pat. No. 6,018,705 to Gaudet et al., entitled "Measuring Foot Contact Time And Foot Loft Time Of A Person In Locomotion," and issued on Jan. 25, 2000, each of which are incorporated entirely herein by reference.

The athletic data set may also include a time value associated with each speed value and/or each distance value. If the athletic information monitoring device 201 can be employed to collect athletic information from different users, then the athletic data computing unit 313 may additionally prompt the user to identify himself or herself in some way. This identification information may then be included with the athletic data set generated from the information provided by the athletic information monitoring device 201. Once the computing unit 313 has generated a set of athletic data from the information provided by the athletic information monitoring device 201, the computing unit 313 may store the athletic data set in the memory 315. As will be discussed in more detail below, when the digital music player 203 subsequently is connected to a computing device implementing an athletic information collection tool, the computing unit 313 will download the athletic data to a display configuration tool hosted on a remote computing device.

While wireless communication between the between the athletic parameter measurement device 207 and the interface device 205 is described for the embodiments illustrated in FIGS. 2-4, any desired manner of communicating between the athletic parameter measurement device 207 and the interface device 205 may be used without departing from the invention, including wired connections. Also, any desired way of placing data derived from the physical or physiological data from the athletic parameter measurement device 207 in the proper form or format for display on or output from electronic device 210 may be provided without departing from the invention. For example, if desired, the athletic parameter measurement device 207 may be specially designed and/or programmed for use with one or more specific electronic devices, e.g., pre-programmed and/or wired to operate with a specific device or devices and to provide output data in a form and format suitable for those devices. In this situation, the interface devices 205 may be marketed and sold to specifically target certain electronic devices, such as specific models of digital music players and even other electronic devices, such as telephones, watches, personal digital assistants, etc. As another alternative, if desired, the interface devices 205 may be programmed at a later time to operate with a wide variety of different electronic devices, e.g., by downloading display or device driver and/or format data for specific electronic devices from the Internet, from disk, or from another source, etc.

If desired, in accordance with at least some examples of this invention, the electronic interface device 205 may further include a display 220 and/or a user input system 222, such as one or more rotary input devices, switches, buttons (as shown in the illustrated example in FIG. 2), mouse or trackball elements, touch screens, or the like, or some combination thereof. The display 220 may be employed to show, for example, information relating to music being played by the digital music player 203, information relating to the athletic information signals being received by the digital music player 203, athletic data being generated by the digital music player 203 from the received athletic information signals, etc. The user input system 222 may be employed, for example: to control one or more aspects of the processing of the input data received via interface device 205, to control input data receipt (e.g., timing, types of information received, on-demand data requests, etc.), to control data output to or by the electronic device 203, to control the athletic parameter measurement device 207, etc. Alternatively or additionally, if desired, the input system on the digital music player 203 (e.g., buttons 222, a touch screen, a digitizer/stylus based input, a rotary input device, a trackball or roller ball, a mouse, etc.), may be used to provide user input data to the interface device 205 and/or to the athletic parameter measurement device 207. As still another example, if desired, a voice input system may be provided with the interface device 205 and/or the digital music player 203, e.g., to enable user input via voice commands. Any other desired type of user input system, for control of any system elements and/or for any purpose, may be provided without departing from the invention.

The digital music player 203 may include additional input and/or output elements, e.g., such as ports 224 and 226 shown in FIG. 2, e.g., for headphones (or other audio output), power supplies, wireless communications, infrared input, microphone input, or other devices. If desired, and if these ports 224 and/or 226 would be covered when the interface device 205 is attached to the electronic device 203, the interface device 205 may be equipped with similar external ports to ports 224 and/or 226, and internal circuitry may be provided in the interface device 205 to enable the user to plug the same additional devices into the interface device 205 as they might plug into the digital music player 203 and still take advantage of the same functions (e.g., to thereby allow the necessary data, signals, power, and/or information to pass through the interface device 205 to the user, to another output, and/or to the digital music player 203).

It should be appreciated that, while some specific embodiments of the invention described above relate to a digital music player 203, alternate examples of the invention may be implemented using any portable electronic device. For example, with some implementations of the invention, the athletic parameter measurement device 207 may be used in conjunction with a mobile telephone, a watch, a personal digital assistant, anther type of music player (such as a compact disc or satellite radio music player), a portable computer, or any other desired electronic device. Still further, some implementations of the invention may alternately or additionally omit the use of the interface device 205. For example, the athletic parameter measurement device 207 may be configured to communicate using the Bluetooth wireless communication protocol, so that it can be employed with Bluetooth-capable mobile telephones, personal digital assistants, watches or personal computers. Of course, still other wireless or wired communication techniques could be employed while omitting the interface device 205.

It also should be appreciated that, while a specific example of an athletic parameter measurement device 207 has been described above for ease of understanding, any type of desired athletic parameter measurement device 207 can be employed with various embodiments of the invention. For example, with some implementations of the invention, the athletic parameter measurement device 207 may be a heart rate monitor, a blood oxygen monitor, a satellite positioning device (e.g., a Global Positioning Satellite (GPS) navigation device), a device for measuring the electrical activity of the user (e.g., an EKG monitor), or any other device that measures one or more physical parameters of the user. Still further, the athletic parameter measurement device 207 may measure one or more operational parameters of some device being manipulated by the user, such as the speed and/or distance of a bicycle, the speed and/or work performed by a treadmill, rowing machine, elliptical machine, stationary bicycle, the speed and/or distance traveled by skis (water or snow), skates (roller or ice), or snowshoes or the like worn by the user, etc.

Also, while the athletic parameter measurement device 207 has been described as being separate for the digital music player 203 or other portable electronic device that receives the signals from the athletic parameter measurement device 207, with some implementations of the invention the athletic parameter measurement device 207 may be incorporated into the digital music player 203 or other portable electronic device. For example, some implementations of the invention may employ a music player, mobile telephone, watch or personal digital assistant that incorporates accelerometers, a satellite positioning device, or any other desired device for measuring athletic activity. Still further, it should be appreciated that various implementations of the invention may employ a plurality of athletic parameter measurement devices 207, incorporated into the digital music player 203 or other portable electronic device, separate from the digital music player 203 or other portable electronic device, or some combination thereof.

Athletic Collection and Display Tools

Figure 5:
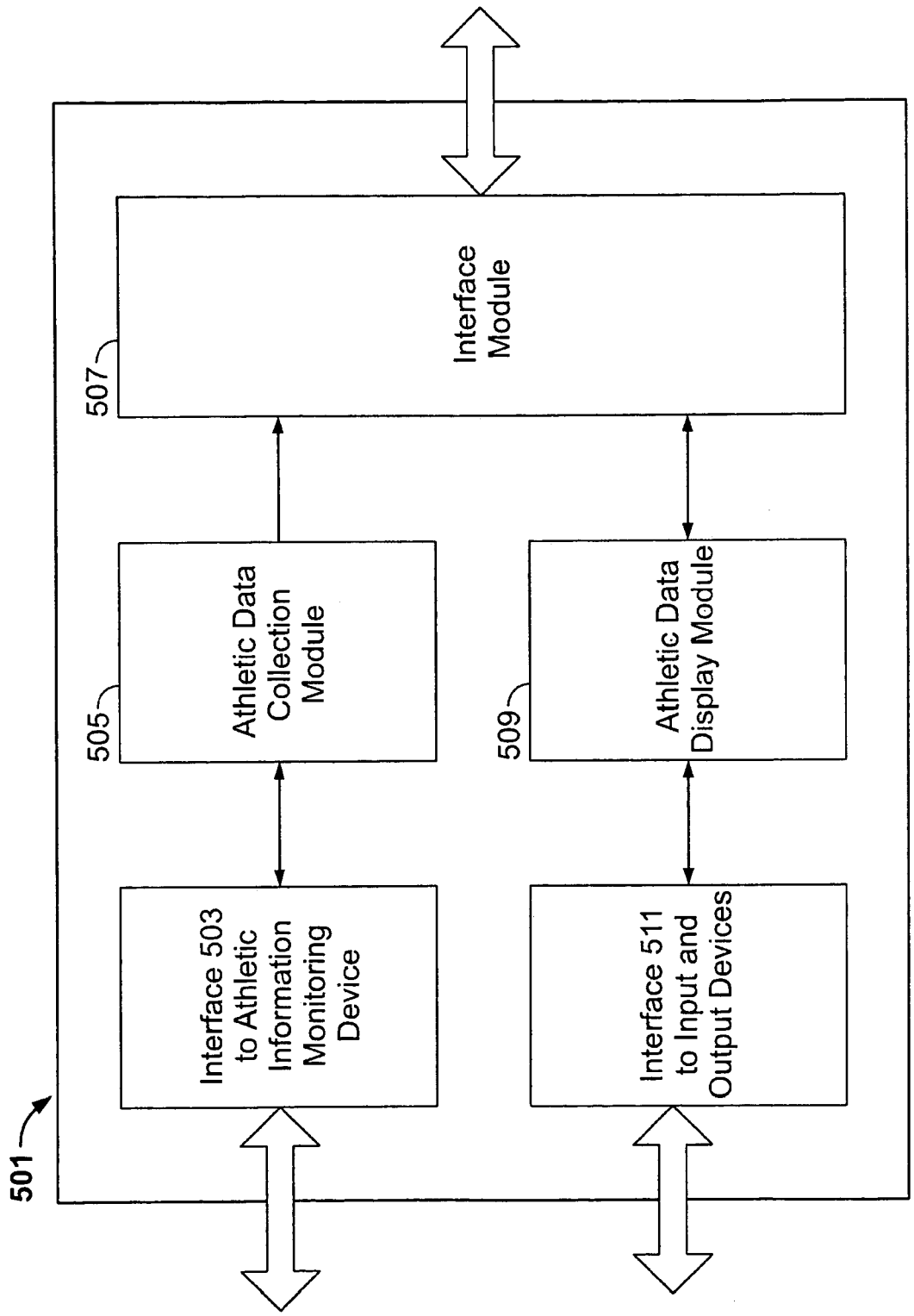
FIG. 5 illustrates an example of an athletic information collection and display device that may be employed to collect and/or display athletic data according to various implementations of the invention.

FIG. 5 illustrates an example of an athletic information collection and display device 501 that may be employed to collect and/or display athletic data according to various implementations of the invention. As will be discussed in more detail below, the athletic information collection and display device 501 may both collect and display athletic data. The athletic information collection and display device 501 may be implemented using any suitable variation of the computing device 101 previously described. In some situations, however, the information collection and display device 501 may be commercially implemented using a desktop or laptop personal computer using, e.g., a version of the Microsoft Windows operating system available from Microsoft Corporation of Redmond, Wash., a version of the Apple Macintosh operating system available for Apple Corporation of Cupertino, Calif., or a version of the Unix or Linux operating systems available from a plurality of vendors.

As shown FIG. 5, the athletic information collection and display device 501 includes an interface 503 for receiving data from the athletic information monitoring device 201. The interface 503 may be implemented using, e.g., electrical components, software components (such as application program interfaces (APIs)), or some combination thereof. The athletic information collection and display device 501 also has an athletic data collection module 505. With various examples of the invention, the athletic data collection module 505 may detect when the digital music player 203 or other portable electronic device storing one or more athletic data sets is connected to the athletic information collection and display device 501 through the interface 503, establish a communication session with the digital music player 203 or other portable electronic device to retrieve the athletic data set or sets. In some implementations of the invention, the athletic data collection module 505 may delete athletic data sets from the digital music player 203 or other portable electronic device after the athletic data sets have been retrieved.

With some examples of the invention, the athletic data collection module 505 may perform some further operations on the athletic data sets retrieved from the digital music player 203 or other portable electronic device. For example, if the athletic information monitoring device 201 can be employed to collect athletic information from different users, then the athletic data collection module 505 may additionally prompt the user to identify himself or herself (if this information was not previously obtained by the athletic information collection and display device 501). This identification information may then be included with the retrieved athletic data sets.

As previously noted, the athletic information collection and display device 501 typically will generate sets of athletic data from information measured by one or more athletic parameter measurement devices 207. With some embodiments of the invention, however, the athletic information collection and display device 501 may instead store the raw information provided by the athletic parameter measurement devices 207. With these embodiments, the athletic data collection module 505 may retrieve the raw information from the digital music player 203 or other portable electronic device, and then generate athletic data sets from the raw information itself. Of course, still other examples of the invention may divide functions relating to the generation of athletic data from the raw information measured by athletic parameter measurement devices 207 between the athletic data collection module 505 and the digital music player 203 or other portable electronic device as desired.

The athletic data collection module 505 may be implemented by, for example, software instructions executed by a computing unit 113 of a computing device 101. With some examples of the invention the athletic data collection module 505 may be implemented by a conventional software tool, such as a browser. Alternately, athletic data collection module 505 may be implemented by a purpose-specific software tool or by a conventional software tool enhanced to perform athletic data collection functions. For example, the athletic data collection module 505 may be implemented by a software tool that incorporates a conventional browser to perform a variety of functions. These functions may include, e.g., selecting, purchasing, and downloading music and video content in addition to collecting athletic data from a digital music player 203 or other portable electronic device.

Once the athletic data collection module 505 has collected the processed signals provided by the athletic information monitoring device 201, the athletic data collection module 505 transmits the athletic data set to an athletic data display configuration device 601 through an interface module 507. The athletic information collection and display device 501 may communicate with the athletic data display configuration device 601 through a conventional network, such as the Internet. With these configurations, the interface module 507 may be implemented using any conventional type of network interface, such as a network interface card. Of course, any type of desired hardware or software combination alternately may be used to allow the athletic data collection module 505 to send the collected athletic data to the athletic data display configuration device 601. With some implementations of the invention, the athletic data collection module 505 may automatically forward collected athletic data to the athletic data display configuration device 601. For example, the athletic data collection module 505 may attempt to forward collected athletic data to the athletic data display configuration device 601 immediately after collection, at a prescheduled interval, upon the detection of a network connection to the athletic data display configuration device 601, or some combination thereof. Alternately or additionally, the athletic data collection module 505 may prompt a user to specify when collected athletic data is sent to the athletic data display configuration device 601.

Figure 6:
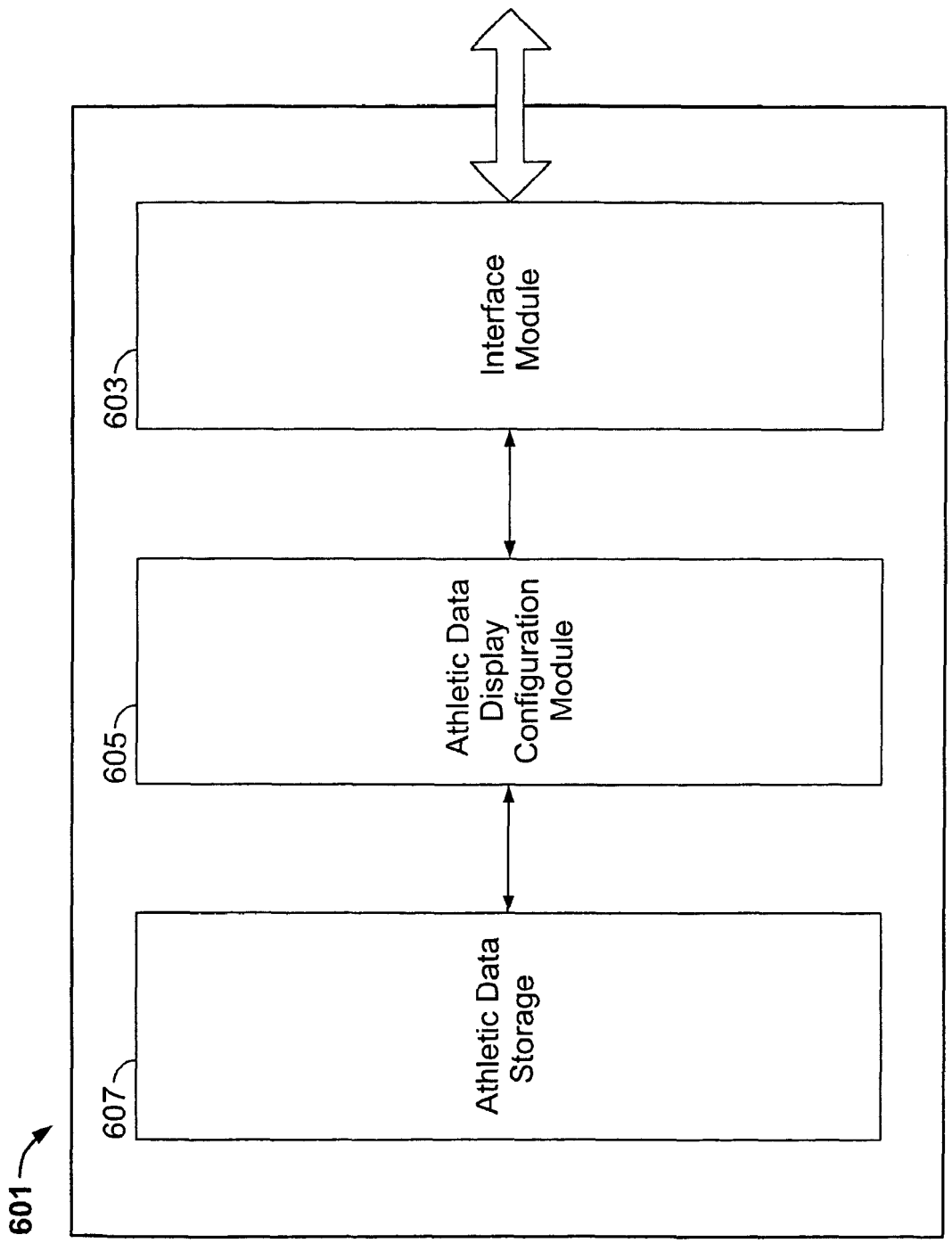
FIG. 6 illustrates an example of an athletic data display configuration device that may be employed according to various examples of the invention.

FIG. 6 illustrates an example of an athletic data display configuration device 601 that may be employed according to various examples of the invention. As seen in this figure, the athletic data display configuration device 601 includes an interface module 603 for communicating with the athletic information collection and display device 501. As previously noted, the athletic information collection and display device 501 may communicate with the athletic data display configuration device 601 through a conventional network, such as the Internet. With these configurations, the interface module 603 may be implemented using any conventional type of network interface, such as a network interface card. Of course, any type of desired hardware or software combination alternately may be used to allow the athletic data display configuration device 601 to communicate with the athletic information collection and display device 501.

The athletic data display configuration device 601 also includes an athletic data display configuration module 605, and an athletic data storage 607. When the interface 603 of the athletic data display configuration device 601 receives athletic data from the athletic information collection and display device 501, it provides the received athletic data to the athletic data display configuration module 605. The athletic data display configuration module 603 may then store the athletic data in the athletic data storage 607 for future use. As will be discussed in more detail below, the athletic data display configuration module 605 also will retrieve athletic data from the athletic data storage 607, and configure the retrieved athletic data for display through one or more user interfaces in a manner that is meaningful to a user.

Returning now to FIG. 5, when a user wishes to view information relating to his or her athletic activities (or the athletic activities of another, as will be discussed in more detail below), the user submits this request to the athletic information collection and display device 501. More particularly, the user can employ conventional input and output devices, such as a keyboard, mouse, display and the like. The display request is then provided to an athletic data display module 509 through a conventional interface input/output interface 511. As well known in the art, the interface input/output interface 511 may be implemented using any desired combination of hardware and software components, such as conventional application programming interfaces (APIs) used to detect and process input from input devices, and to send data to and otherwise control output devices.

With some examples of the invention, the athletic data display module 509 may be implemented using any conventional tool for receiving input to request and control the display of data, and then subsequently displaying the data in the manner requested. For example, the athletic data display module 509 may be implemented using a conventional browser program, such as Microsoft Internet Explorer, Mozilla Firefox, or Opera executing on a computing unit 113. With still other embodiments of the invention, the athletic data display module 509 may be implemented using a conventional browser program that has been enhanced by one or more display tools, such as an ActiveX plug-in, a Java script or a version of the Macromedia Flash Player or Adobe Flash Player, available from Adobe Systems Incorporated of San Jose, Calif. In still other embodiments of the invention, the athletic data display module 509 may be implemented by, for example, a purpose-specific software tool for displaying athletic data.

As will be discussed in more detail below, when a user activates the athletic data display module 509, he or she is provided with a user interface prompting the use to select what collected athletic data he or she wishes to view, the format in which the user wishes to view the collected athletic data, etc. This user interface may be generated by the athletic data display module 509, the athletic data display configuration module 605, or some combination thereof. When a user employs the provided user interface to submit a request to view athletic data, the athletic data display module 509 relays the request to the athletic data display configuration module 605. In response, the athletic data display configuration module 605 configures the requested athletic data for display by the athletic data display module 509. For example, as will be discussed in more detail below, a user may request to view the total distance run by a user for each day in a one week period. In response, the athletic data display configuration module 605 will retrieve the relevant distance data from the athletic data storage 607. It will then configure the retrieved distance data to be displayed through a desired image (e.g., a bar graph), and provide the configured athletic data to the athletic data display module 509 for display to the user.

It should be noted that, with some embodiments of the invention, the data display configuration functions may be divided between the athletic data display module 509 and the athletic data display configuration module 605. For example, if the athletic data display module 509 is implemented by a simple browser, then the athletic data display module 509 may serve as a "thin client" for the athletic data display configuration module 605. That is, all of the data display configuration functions may be performed by the athletic data display configuration module 605. The athletic data display module 509 will then only display the information provided to it. Alternately, if the athletic data display module 509 is implemented by a purpose-specific software tool, then most or all of the data display configuration functions may be performed by the athletic data display module 509. With these examples, the athletic data display configuration module 605 may be used only to store and retrieve athletic data from the athletic data storage 607.

Figure 7:
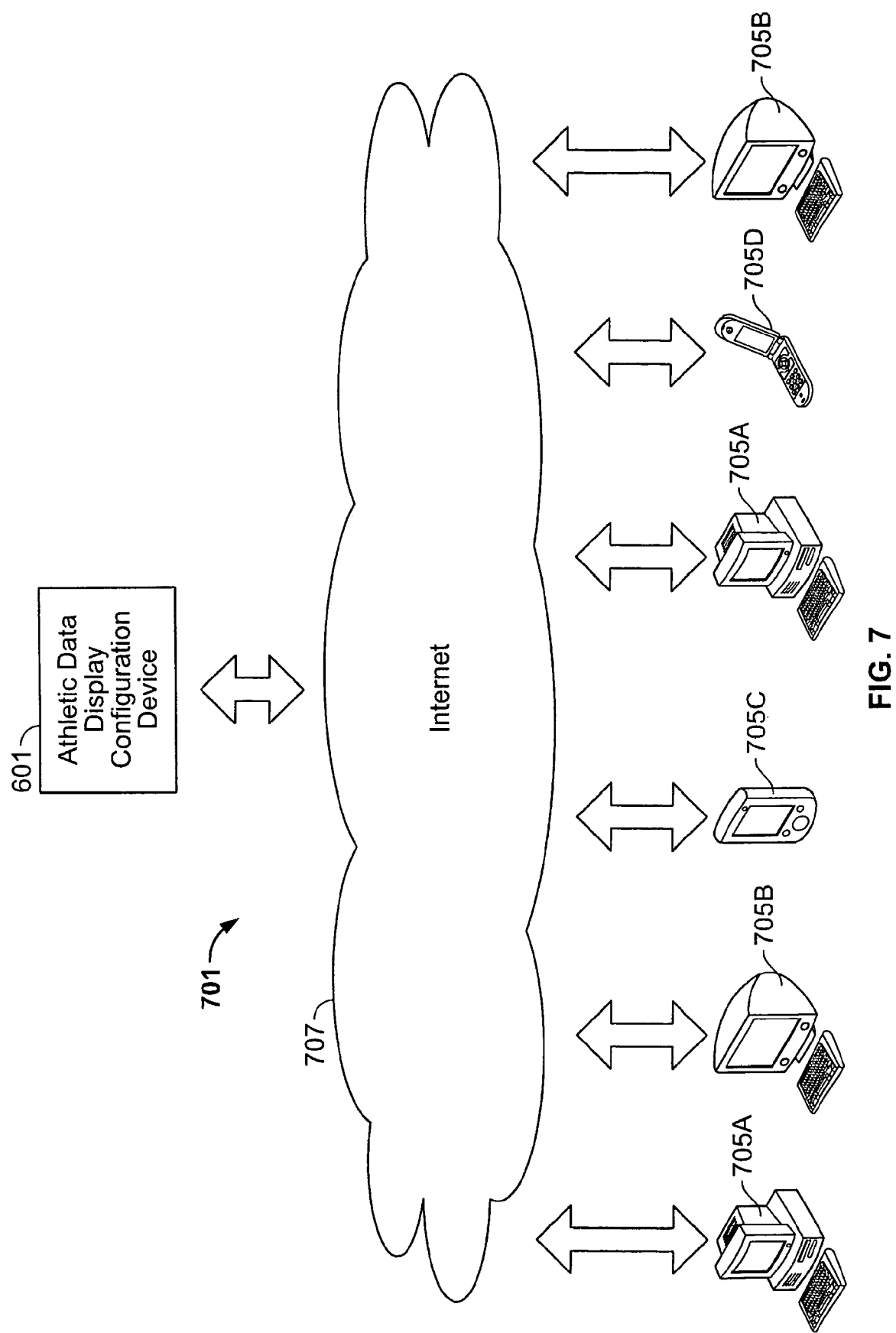
FIG. 7 illustrates a network including an athletic data display configuration device and a plurality of client devices of the type that may be employed according to various examples of the invention.

Typically, the athletic data display configuration device 601 will be implemented at a remote location from the athletic information collection and display device 501. The athletic information collection and display device 501 then may be connected to the athletic data display configuration device 601 through an electronic communication network, as previously noted. The electronic communication network may be a public network, such as the Internet, a private network, or include some combination of both. For example, FIG. 7 illustrates a network 701 including an athletic data display configuration device 601 and a plurality of client devices 705 for collecting and/or displaying athletic data. These client devices 705 may include personal computers 705A using some version of the Microsoft Windows operating systems available from Microsoft Corporation of Redmond, Wash., personal computers 705B using some version of the Apple operating system, personal digital assistants 705C and telephones 705D. Of course, various examples of the invention may alternately or additionally include any other desired electronic device that can be configured to collect and/or display athletic data as discussed above.

It should be appreciated that a client device 705 may perform an athletic data collection function, an athletic data display function, or both. That is, while the example of the athletic information collection and display device 501 described above is capable of both collecting and displaying athletic data, some client devices 705 may only collect athletic data. Further, some client devices may only display athletic data. For example, a user may employ a GPS-equipped smart telephone to collect athletic data and transmit the collected athletic data to the athletic data display configuration device 601. The user may then employ a personal computer equipped with only a conventional browser to subsequently download and display the collected athletic data.

Display of a User's Athletic Information

Display of Athletic Activity Values

In response to receiving a request to review athletic information from a user via the athletic data display module 509, the athletic data display configuration module 605 will determine the user's identity. The athletic data display configuration module 605 will then retrieve the athletic data associated with the user from the athletic data storage 607. Next, the athletic data display configuration module 605 will prepare a user interface for displaying the requested athletic data, and transmit the user interface with the athletic data to the athletic data display module 509 for display to the user.

Figure 8A:
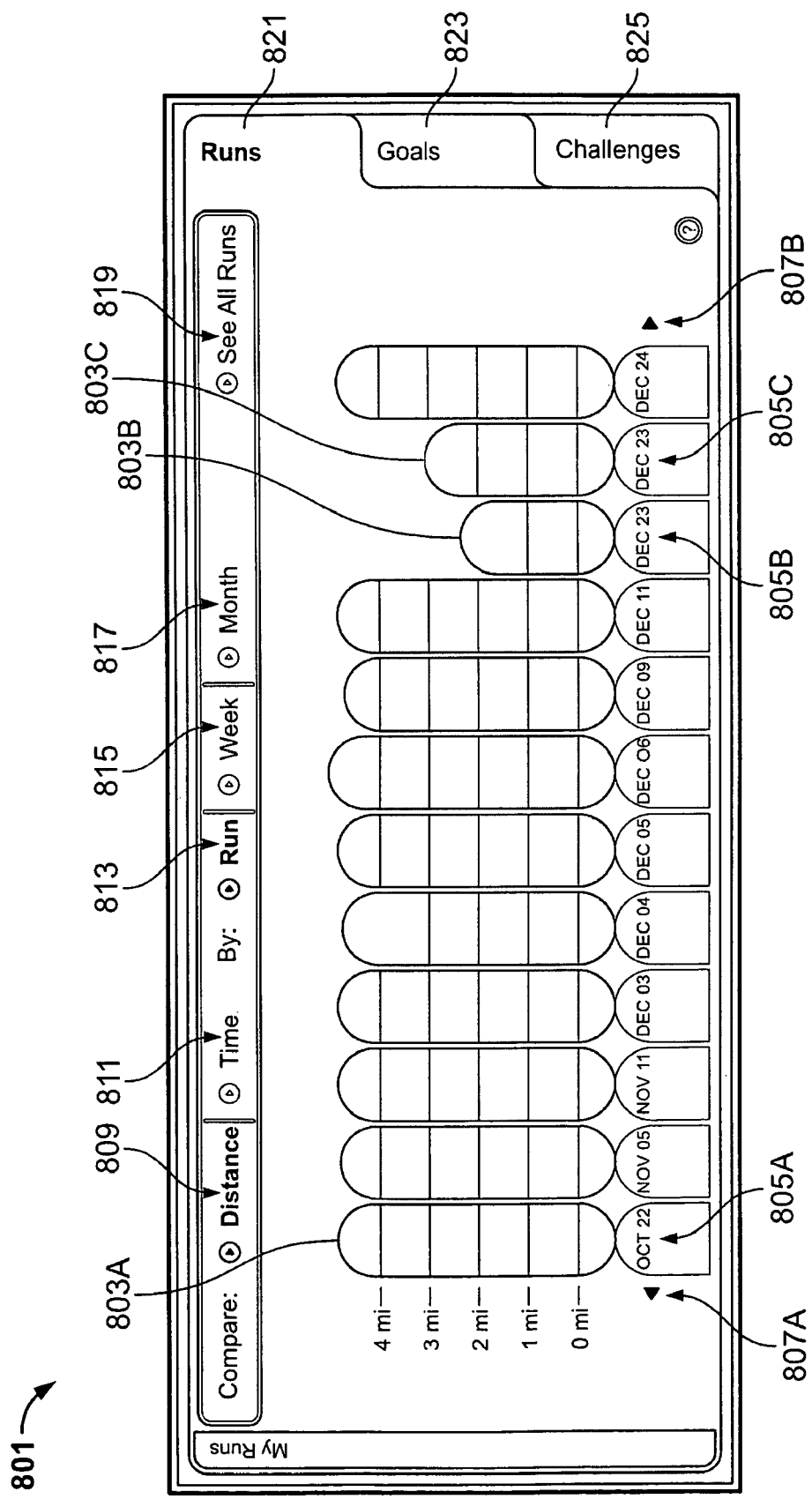
FIGS. 8A-8F, 9A and 9B illustrate examples of user interfaces that may be provided to display athletic data for a user according to various implementations of the invention.

FIG. 8A illustrates an example of an initial user interface that may be provided to a user according to various implementations of the invention. As seen in this figure, the user interface 801 includes a plurality of icons 803. Each icon 803 represents an athletic data value corresponding to an athletic activity performed by the user over a specified time period. More particularly, each icon 803 represents a distance value corresponding to athletic activity performed by a user. A calendar date field 805 associated with each icon 803 is shown at the bottom of each icon 803 to indicate the date on which the corresponding athletic activity was performed, as illustrated in FIG. 8. The user interface 801 also displays a number of control buttons 807-819 that allow the user to select what athletic data values will be displayed in the user interface as well as the time periods for which the athletic data values will be displayed. In addition, the interface 801 includes tabs 821-825, which will be discussed in more detail below.

As shown in FIG. 8A, the user has activated the "Distance" button 809 and the "Run" button 813. In response, the display 801 initially shows an icon 803 for the each of the most recent, e.g., twelve sets of athletic data collected by the server that corresponds to the user. As previously noted, each data set includes athletic data values generated from athletic information measured during a single, discrete athletic activity performed by a person over a particular time period. Further, the height of each icon 803 will correspond to the total distance value included in the set of athletic data represented by the icon 803. For example, on October 22, the user traveled a total distance of 4.05 miles during a run, whereas the user traveled a total distance of only 1.59 miles during a first run on December 23. Accordingly, the icon 803A corresponding to the athletic activity on October 22 will be proportionally larger than the icon 803B representing the athletic data collected for the user's first run on December 23, as shown in this figure. If the user wishes to view icons 803 for athletic activities performed before or after the athletic activities corresponding to the displayed icons 803, the user can view those additional icons 803 by activating the desired arrow buttons 807.

Figure 8B:
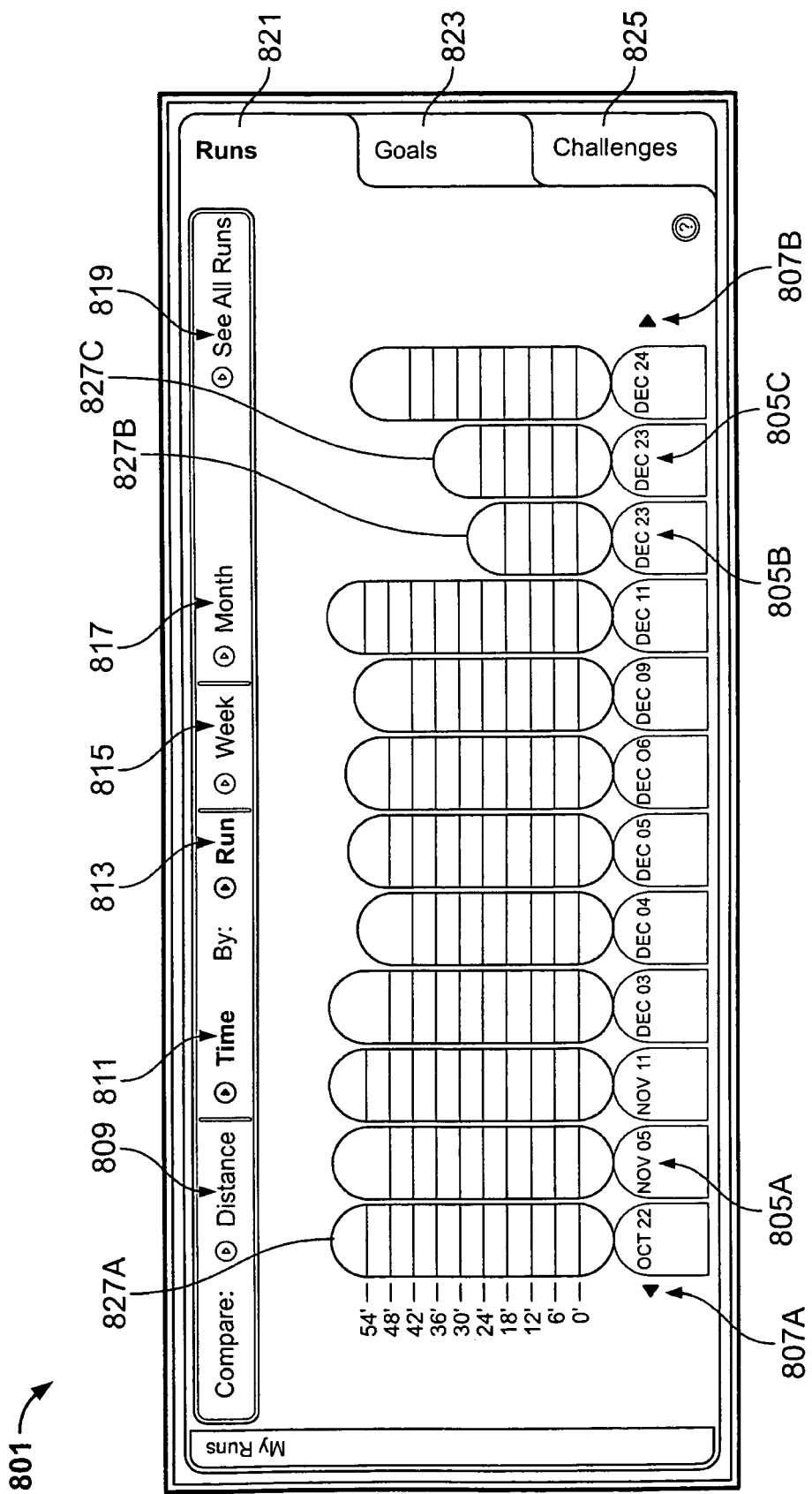

If a user subsequently selects the "Time" button 811, the athletic data display configuration module 605 will reconfigure the user interface 801 to display new icons 827 so that each icon 827 represents a total time value for each of the data sets. For example, as shown in FIG. 8B, the height of each icon 827 will correspond to the total time value in each represented data set. For example, if the length of the user's run on October 22 was 54 minutes, 2 seconds, whereas the duration of the user's first run on December 23 was only 18 minutes, 11 seconds, then the icon 827A corresponding to the athletic data set for October 22 will be proportionally taller than the icon 827B representing the athletic data set collected for the user's run on December 23.

In addition to displaying only distance and time information, the user interface 801 may optionally display additional information. For example, with some implementations of the invention, a user may employ a pointing device to select a specific icon 803 or 827. In response to the selection by, e.g. positioning a cursor over the icon, the user interface 801 may display additional information from the athletic data set represented by the selected icon. For example, the user interface 801 may use, e.g., a pop-up display (not shown) to display data values for the total distance, time, speed, and calories burned for the athletic activity represented by the selected icon 803 or 827. Still further, the user interface may use, e.g., color information to distinguish between the most-recently collected sets of athletic data and athletic data sets that were collected at an earlier time. Thus, the icons 803 or 827 representing data sets collected during the most recent download from an athletic information monitoring device 201 may be illustrated using, e.g., a light green color, while icons 803 or 827 representing previously-collected athletic data sets may be displayed with a dark green color.

Figure 9A:
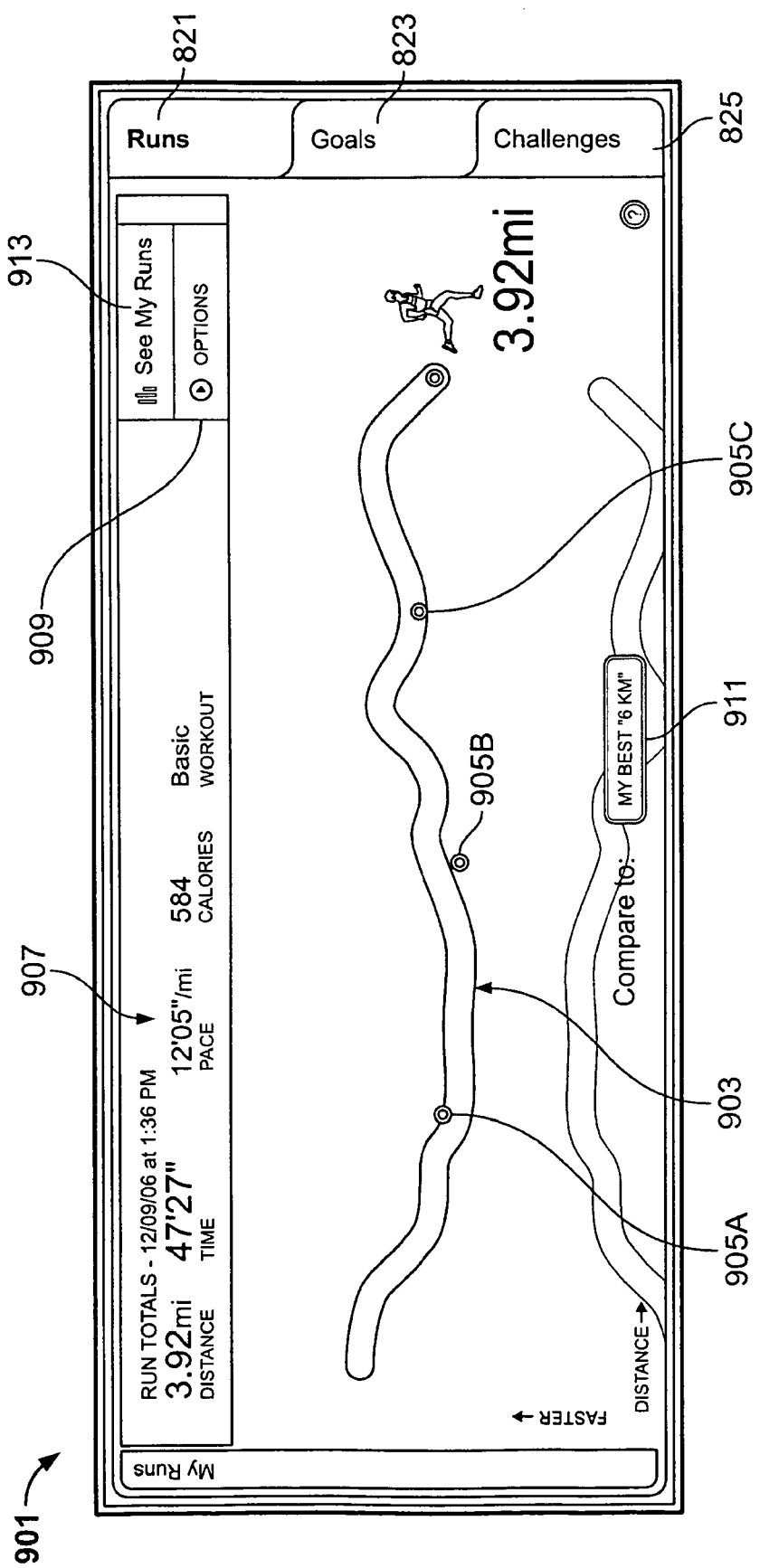

With some implementations of the invention, a user may obtain still more detailed information regarding an athletic data set by "activating" the icon 803 or 827 representing the athletic data set. For example, a user may position a cursor over a desired icon 803 or 827 using a pointing device, and then depress a selection button to activate the icon 803 or 827. In response, the athletic data display configuration module 605 will configure and provide a user interface graphically illustrating the data values in the corresponding athletic data set in more detail. For example, as illustrated in FIG. 9A, various implementations of the inventions may display a user interface 901 plotting a first type of data in the data set against a second type of data in the data set to provide a visual graph 903. More particularly, as illustrated in this figure, the athletic data display configuration module 605 will plot speed values in the athletic data set against distance values data in the athletic data set, providing the graph 903. In this manner, a user can view what his or her instantaneous speed was at various points during the run. In addition, the graph 903 may include other relevant information such as, for example, an icon showing the type of athletic activity (e.g., running) and an indication on of the total distance traveled.

With some implementations of the invention, the graph 903 also may include specific distance waypoints 905, which will show the particular speed value measured at the distance during the athletic activity represented by the position of the waypoint 905. For example, if the user employs a pointing device to move a cursor over waypoint 905A, the user interface 901 will display a pop-up window (not shown) indicating that the user had an average speed of 12 minutes, 12 seconds at the first mile. Similarly, if the user employs a pointing device to move a cursor over the waypoint 905B, the user interface 901 will display a pop-up window (not shown) indicating that the user had an average speed of 12 minutes, 17 seconds at the second mile. If the user then employs a pointing device to move a cursor over the waypoint 905C, the user interface 901 will display a pop-up window (not shown) indicating that the user had an average speed of 12 minutes, 3 seconds at the third mile.

The user interface 901 also may include a value field 907 indicating the total distance value, total time value, total average pace value, total calories burned value, and athletic activity type value corresponding to the represented athletic activity. It also may include an "Options" button 909. If the user activates the "Options" button 909, the interface 901 may display additional command buttons (not shown) that allow the user to name the selected athletic data set or delete the athletic data set. Still further, the interface may include a "Comparison" button 911.

If the user selects the "Comparison" button 911, the athletic data display configuration module 605 will determine a time or distance classification for the selected athletic activity. For example, if the total distance value collected for the selected athletic activity is approximately 6 kilometers, then the athletic data display configuration module 605 will classify the athletic data set corresponding to the selected athletic activity as a "6 kilometer" athletic data set. Similarly, if the total distance value collected for the selected athletic activity is proximal to another specified distance category (e.g., 1 mile, 10 kilometers, 15 kilometers, 10 miles, 26 miles, etc.), then the athletic data display configuration module 605 will classify the athletic data set based upon the relevant category.

Figure 9B:
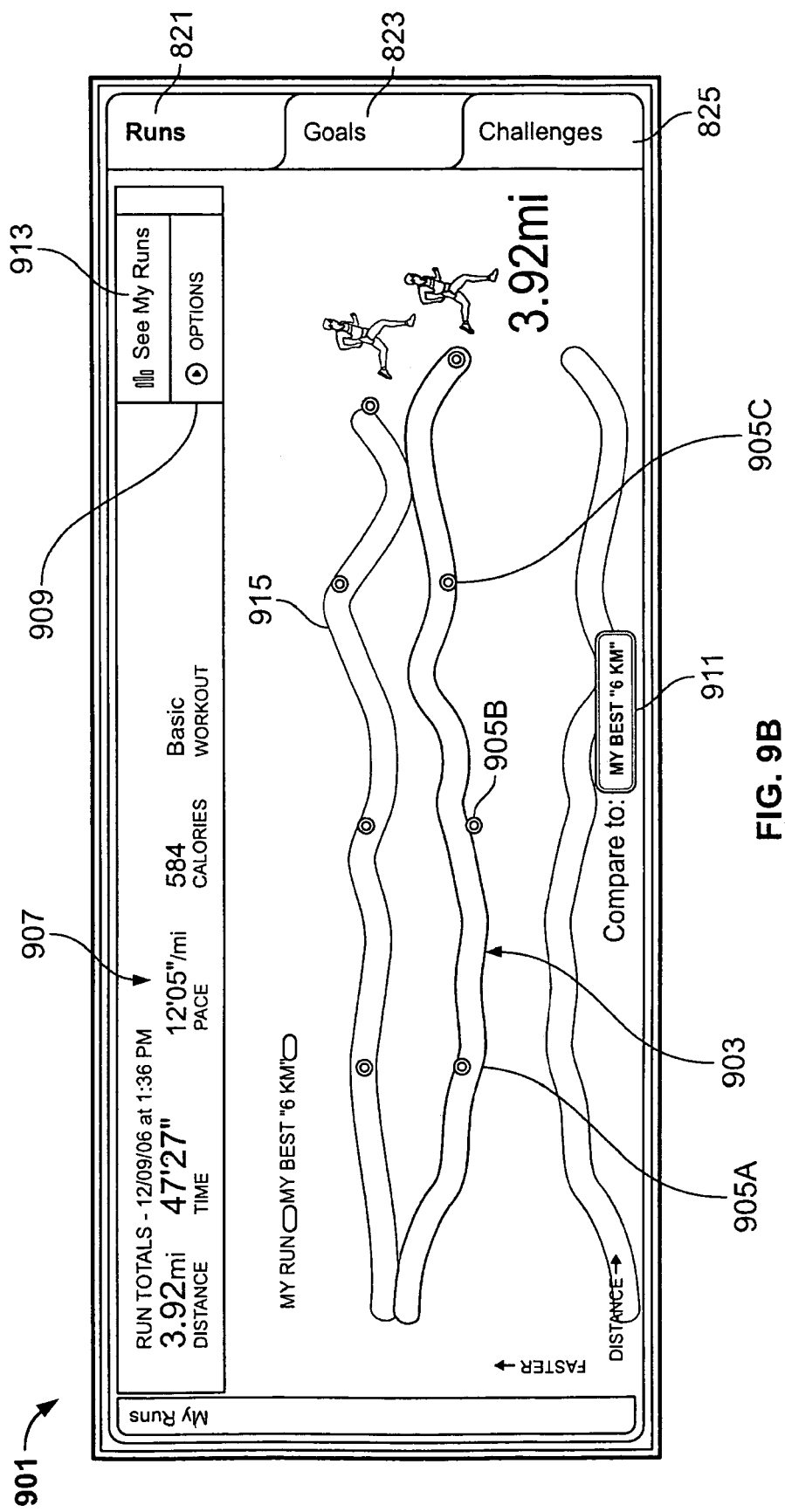

After the athletic data display configuration module 605 has classified the athletic data set, it examines the other athletic data sets in that classification to determine which athletic data set has the highest total distance value (or, if the classification is based upon time or speed, the lowest total time value or the highest average speed value). Once the athletic data display configuration module 605 identifies the "best" set of athletic data for the determined classification, it will then reconfigure the user interface 901 to include a graph of this "best" athletic data set as shown in FIG. 9B. As seen in this figure, the graph 915 may have the same characteristics and features as the graph 905 representing the selected athletic activity session.

If the user selects the "See My Runs" button 913, the athletic data display configuration module 605 will configure and provide the interface 801 for display, as shown in FIGS. 8A and 8B. Returning now to those figures, if the user selects the "Week" button 815 or the "Month" button 817, the athletic data display configuration module 605 will modify the user interface 801 to display one or more icons representing an aggregation of multiple sets of athletic data. More particularly, the athletic data display configuration module 605 will aggregate data values from each athletic data set based upon the designated time period.

Figure 8C:
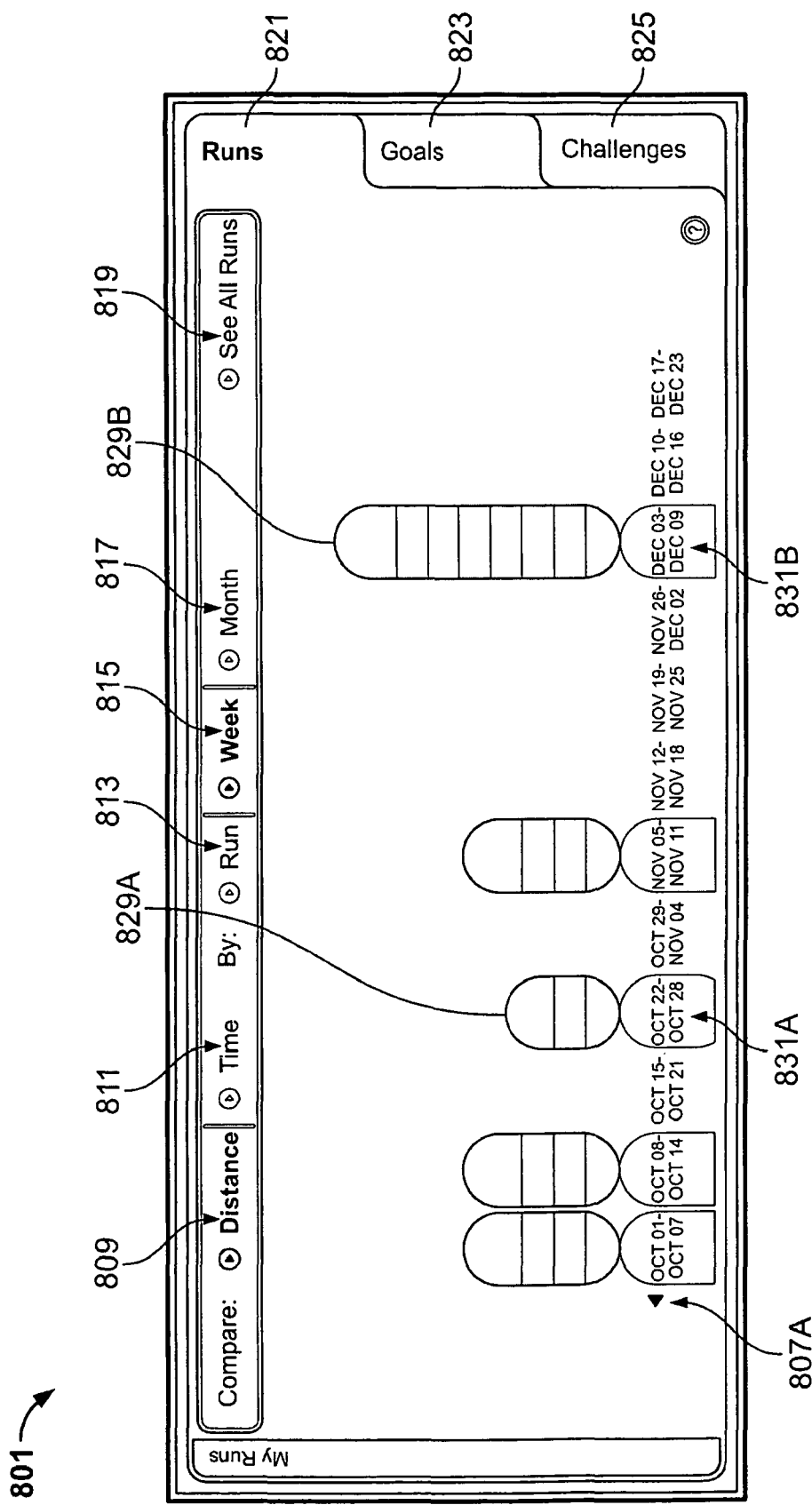

For example, if the user has selected the "Distance" button 809 in addition to the "Week" button 815, then the athletic data display configuration module 605 will add up the total distance data values for each set of athletic data corresponding to an athletic activity session occurring within a particular calendar week. The athletic data display configuration module 605 will then modify the user interface 801 to include icons 829, where each icon 829 graphically represents the sum of total distance values in the athletic data sets generated during a particular week. The athletic data display configuration module 605 may also modify the user interface 801 to include a calendar week field 831 specifying the calendar week to which each icon 829 is associated. As shown in FIG. 8C, the height of each icon represents the sum of the total distance values for each athletic data set for the specified week period. For example, the user may have run a total of 4.05 miles during the weekly period from October 22 to October 28. On the other hand, the user may have run a total distance of 20.25 miles during the week period of December 3 to December 9. Accordingly, the icon 829B representing the aggregated athletic data for the week of December 3 to December 9 will be proportionally larger than the icon 829A representing the athletic data aggregated from the athletic data sets obtained for the week of October 22 to October 28.

Figure 8D:
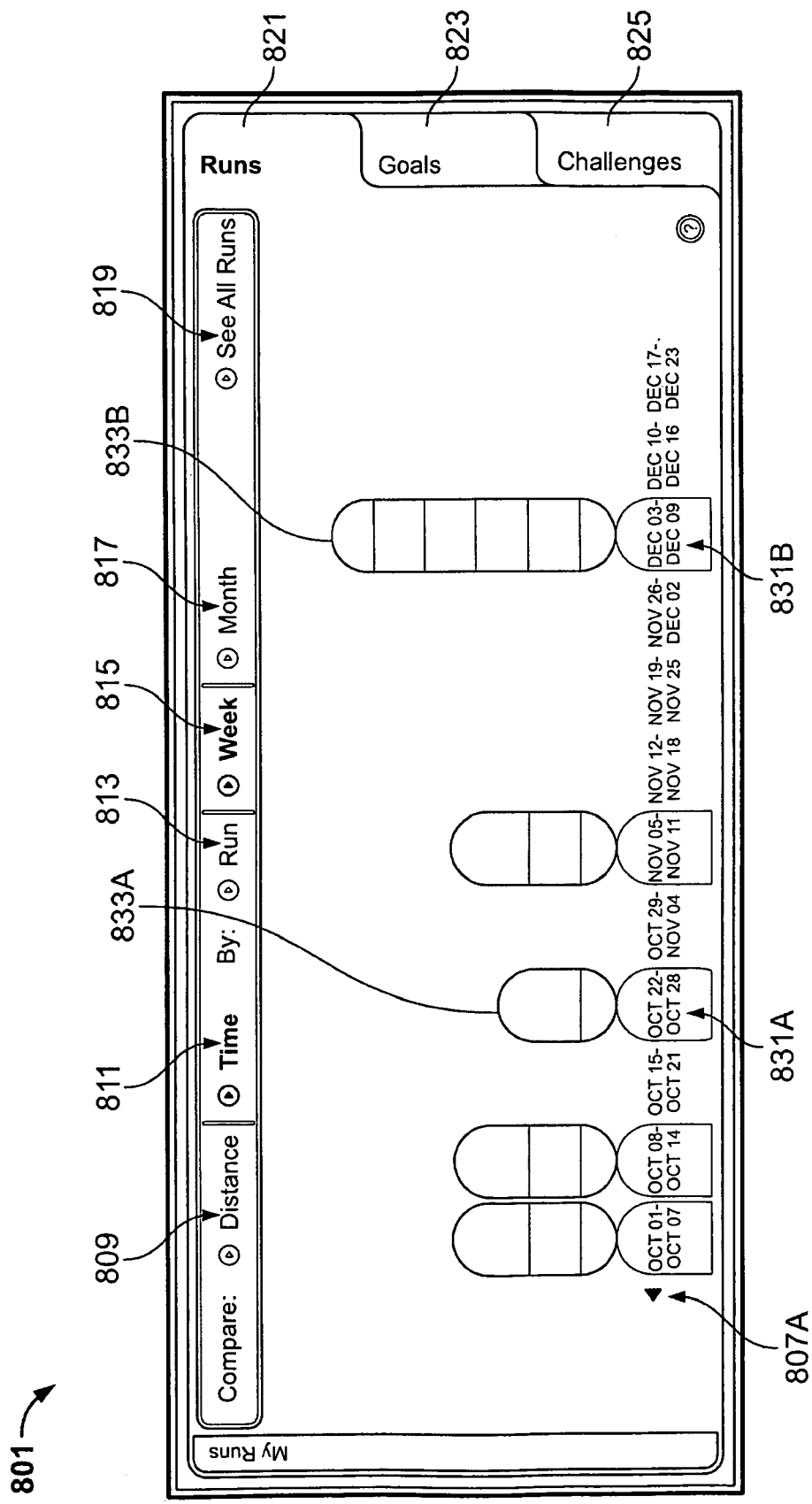

Similarly, if the user selects the "Time" button 811, the athletic data display configuration module 605 will modify the user interface 801 to display icons 833 that represent the sum of total time values for aggregated sets of athletic data. More particularly, as shown in FIG. 8D, a height of each icon 833 will represent the sum of the total time values for each athletic data set obtained during the corresponding weekly period. For example, if a user ran for a total time of 54 minutes 2 seconds during the week from October 22 to October 28, but ran for a total time of 4 hours 7 minutes and 24 seconds during the week of December 3 to December 9, then the icon 833B representing the aggregation of athletic data for the week of December 3 to December 9 will be proportionally larger than the icon 833A representing the aggregation of athletic data for the weekly period of October 22 to October 28.

Figure 8E:
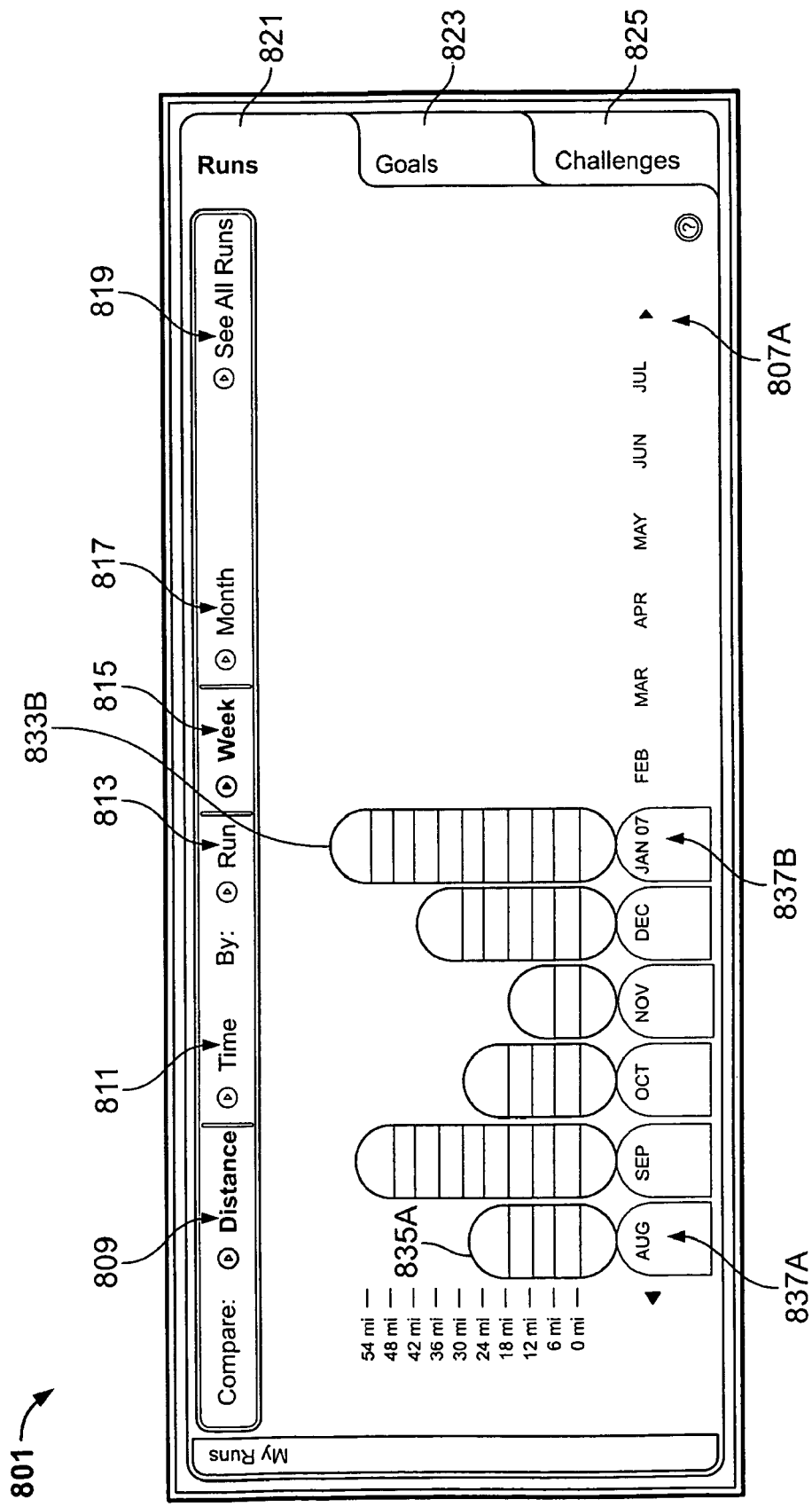

Similarly, if the user selects the "Month" button 817, the athletic data display configuration module 605 will modify the user interface 801 to display icons representing the aggregations of data values from athletic data sets obtained over each monthly time period. For example, if the user has selected the "Distance" button 809 as well, the user interface 801 may display an icon 835 representing the aggregation of total distance values from data sets obtained for athletic activity sessions performed during each calendar month, as illustrated in FIG. 8E. The user interface 801 also may include a calendar month field 837 specifying the calendar month to which each icon 835 is associated. As shown in this figure, the user interface 801 thus includes an icon 835A representing the aggregation of total distance values from data sets obtained for athletic activity sessions performed during the month of August, and another icon 835B representing the aggregation of total distance values from data sets obtained for athletic activity sessions performed during the month of January. The height of the icon 835A represents the sum of the total distance values for each athletic data set obtained for athletic activity sessions performed in August (i.e., 18.84 miles), while the height of the icon 835B correspond to the sum of each of the total distance data values for each athletic data set obtained for athletic activity sessions performed in January (i.e., 58.84 miles).

Figure 8F:
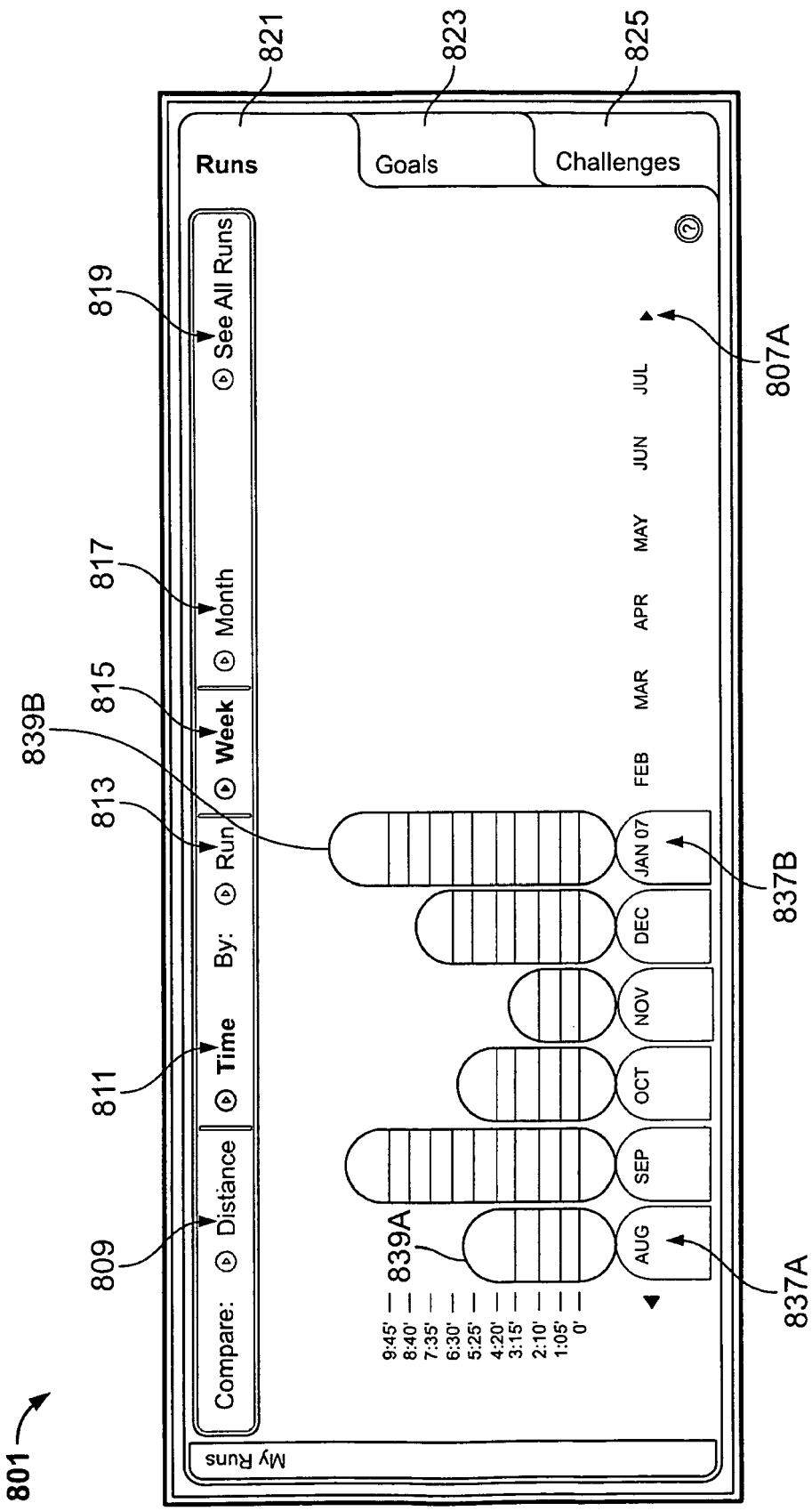

If, on the other hand, the user has selected the "Time" button 811, the user interface 801 may display an icon 839 representing the aggregation of total time values from data sets obtained for athletic activity sessions performed during each calendar month, as illustrated in FIG. 8F. As shown in this figure, the user interface 801 thus includes an icon 839A representing the aggregation of total distance values from data sets obtained for athletic activity sessions performed during the month of August, and another icon 839B representing the aggregation of total time values from data sets obtained for athletic activity sessions performed during the month of January. The height of the icon 839A represents the sum of the total time values for each athletic data set obtained for athletic activity sessions performed in August (i.e., 4 hours, 6 minutes, 1 second), while the height of the icon 839B correspond to the sum of each of the total time data values for each athletic data set obtained for athletic activity sessions performed in January (i.e., 10 hours, 47 minutes, 27 seconds).

In addition to displaying only distance and time information, the user interface 801 may optionally display additional information aggregated from multiple sets of athletic data. For example, with some implementations of the invention, a user may employ a pointing device to select a specific icon 829, 833, 835 or 839. In response to the selection by, e.g. positioning a cursor over the icon, the user interface 801 may display additional information from the aggregation of athletic data sets represented by the selected icon. For example, the user interface 801 may provide, e.g., a pop-up display (not shown) to display sum of total distance data values corresponding to the aggregation of athletic activity information represented by the selected icon, the some of the total time data values corresponding to the aggregation of athletic activity information represented by the selected icon, the average of the average speed data values corresponding to the aggregation of athletic activity information represented by the selected icon speed, and the sum of the calories burned data values data values corresponding to the aggregation of athletic activity information represented by the selected icon.

It should be noted that the athletic data display configuration module 605 (or, with some implementations of the invention, the athletic data display module 509) may aggregate data from multiple athletic data sets in advance of receiving a request to display aggregated athletic data from a user. Alternately, the athletic data display configuration module 605 (or, with some implementations of the invention, the athletic data display module 509) may aggregate data from multiple athletic data sets only in response to a specific request from a user to view the aggregated data.

Display of Goals

Figure 10:
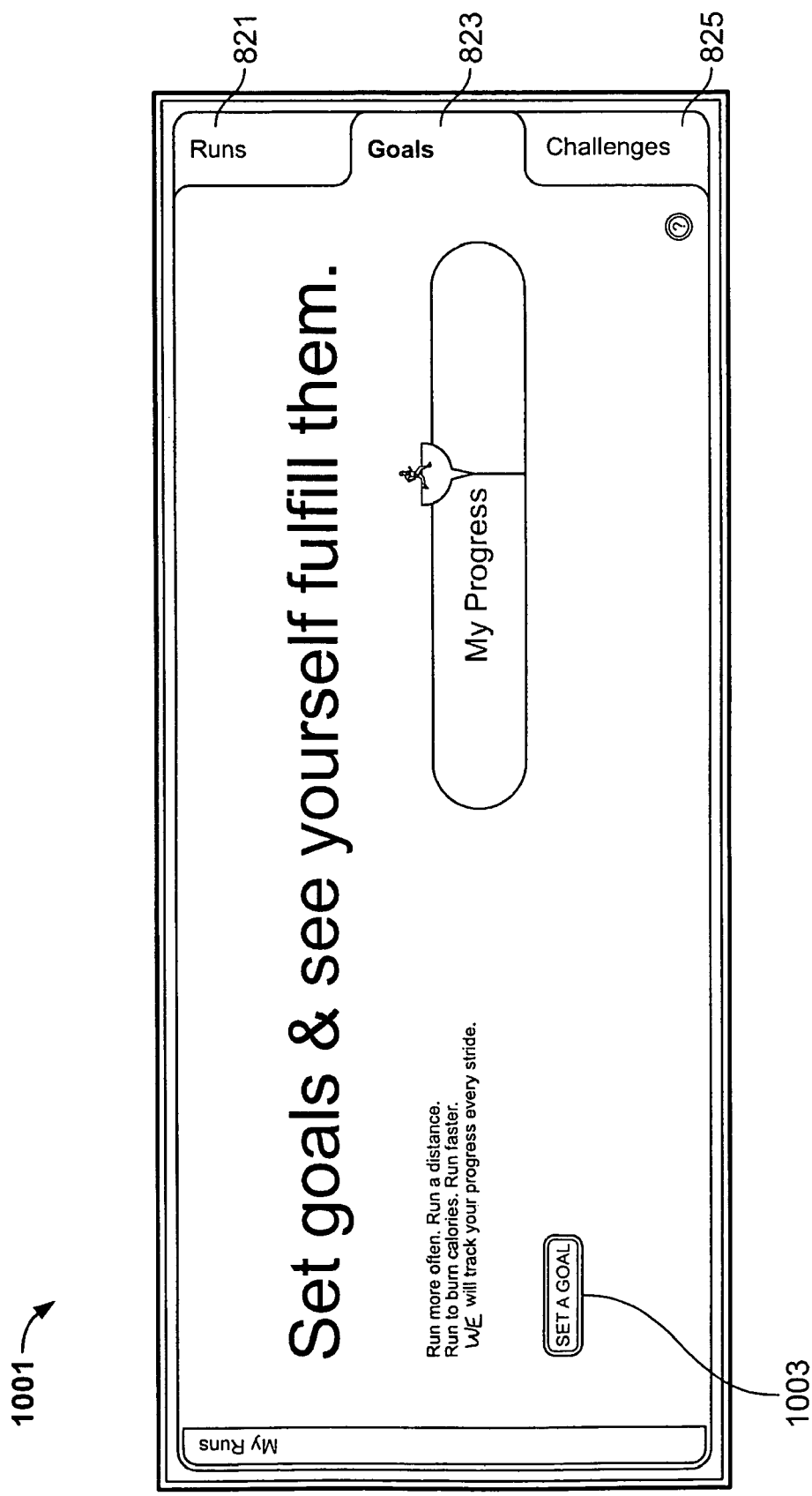

In addition to displaying specific athletic data values or aggregates of athletic data values, various embodiments of the invention may alternately or additionally permit a user to set a goal relating to his or her athletic activities, and then view one or more images graphically illustrating the user's progress toward accomplishing those goals. For example, with the embodiments illustrated in FIGS. 8A-9B, a user can select the "Goals" tab 823 shown in these figures. In response, the athletic data display configuration module 605 may configure and provide the user interface 1001 illustrated in FIG. 10. As seen in this figure, the user interface 1001 includes a "Set A Goal" button 1003 prompting the user to select a desired goal relating to his or her athletic activities.

When the user activates the "Set A Goal" button 1003, the athletic data display configuration module 605 will configure and provide the user interface 1101 shown in FIG. 11. As seen in this figure, the user interface 1101 includes a "More Often" button 1103, a "Distance" button 1105, a "Burn More Calories" button 1107, a "Faster" button 1109, and a "Back" button 1111. As known in the art, activating the "Back" button 1111 will cause the athletic data display configuration module 605 (or, with some examples of the invention, the athletic data display module 509) to configure and display the previously displayed configuration of the user interface 1101, or if the currently displayed configuration of the user interface 1101 is its initial configuration, a previously shown user interface.

Figure 11A:
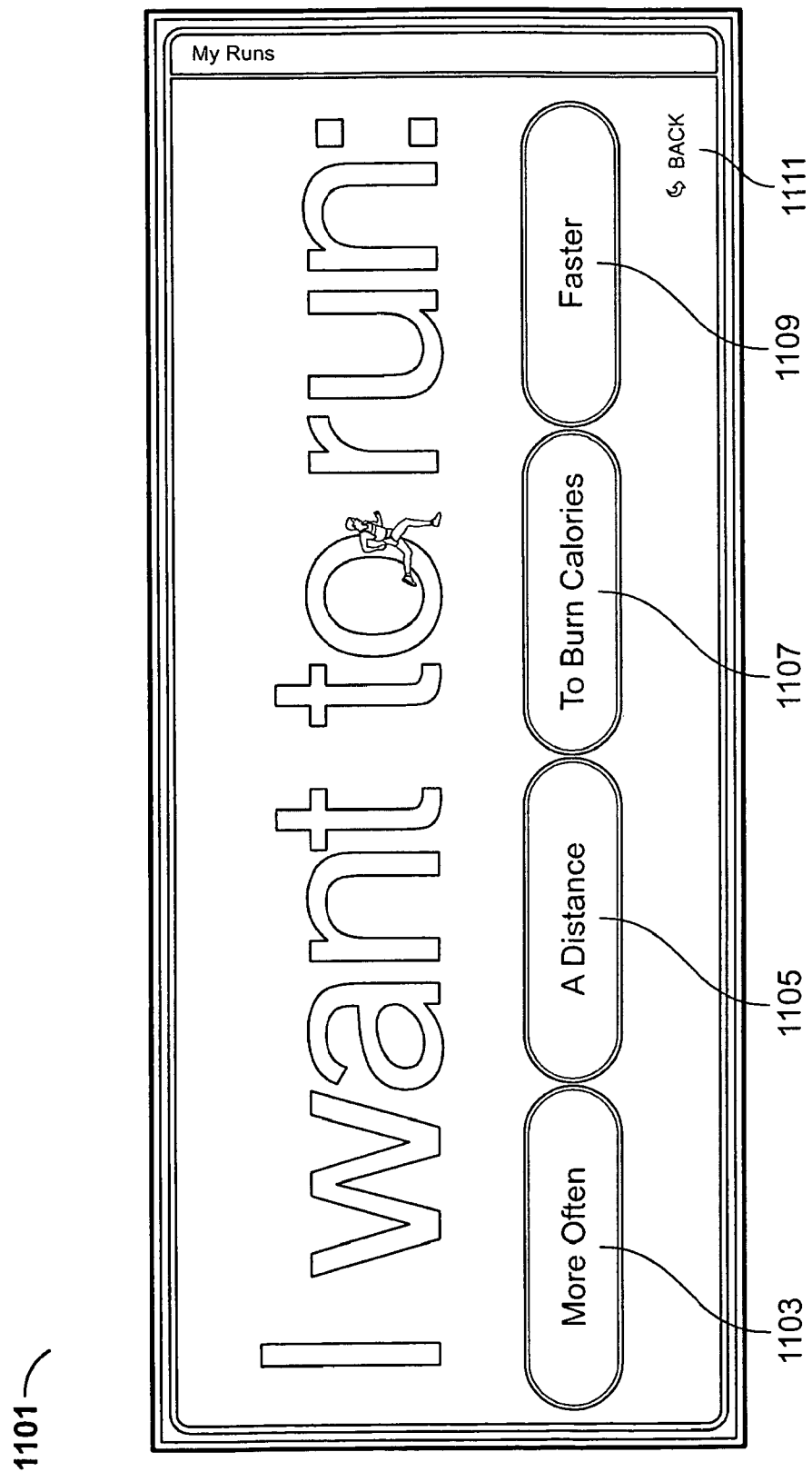
Figure 11B:
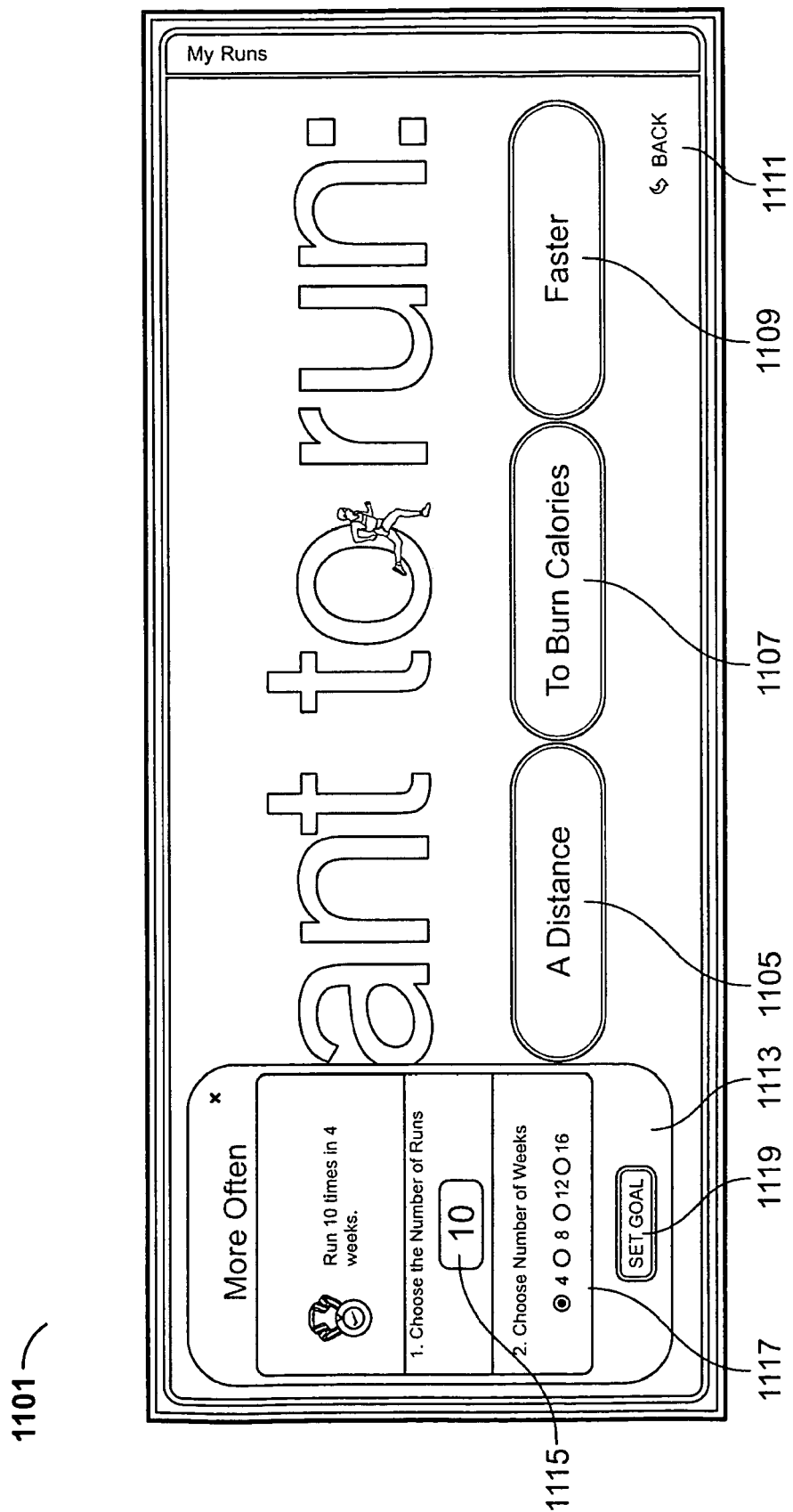

If a user wishes to perform the athletic activity more often, then the user activates the "More Often" button 1103. In response, the athletic data display configuration module 605 reconfigures the user interface 1101 to include a sub-interface 1113. As seen in FIG. 11B, the sub-interface 1113 includes a "Number Of Runs" control 1115, a "Number Of Weeks" control 1117, and a "Set Goal" button 1119. By employing the "Number Of Runs" control 1115, a user can specify the number of runs (or the number of times to perform some other athletic activity, if appropriate) he or she wishes to make within a desired time period. Similarly, by employing the "Number Of Weeks" control 1117, a user can specify the number of weeks making up the desired time period allowed to reach the desired goal. In the illustrated example, the "Number Of Runs" control 1115 is a field control (i.e., having a field in which a value can be typed in) while the "Number Of Weeks" control 1117 is a radio control, but various examples of the invention may employ alternate types of controls as desired. Once a user has specified the number of runs that must be made and specified the time period in which they must be made to meet a desired goal, the user can finalize the goal parameters by activating the "Set Goal" button 1119.

Figure 11C:
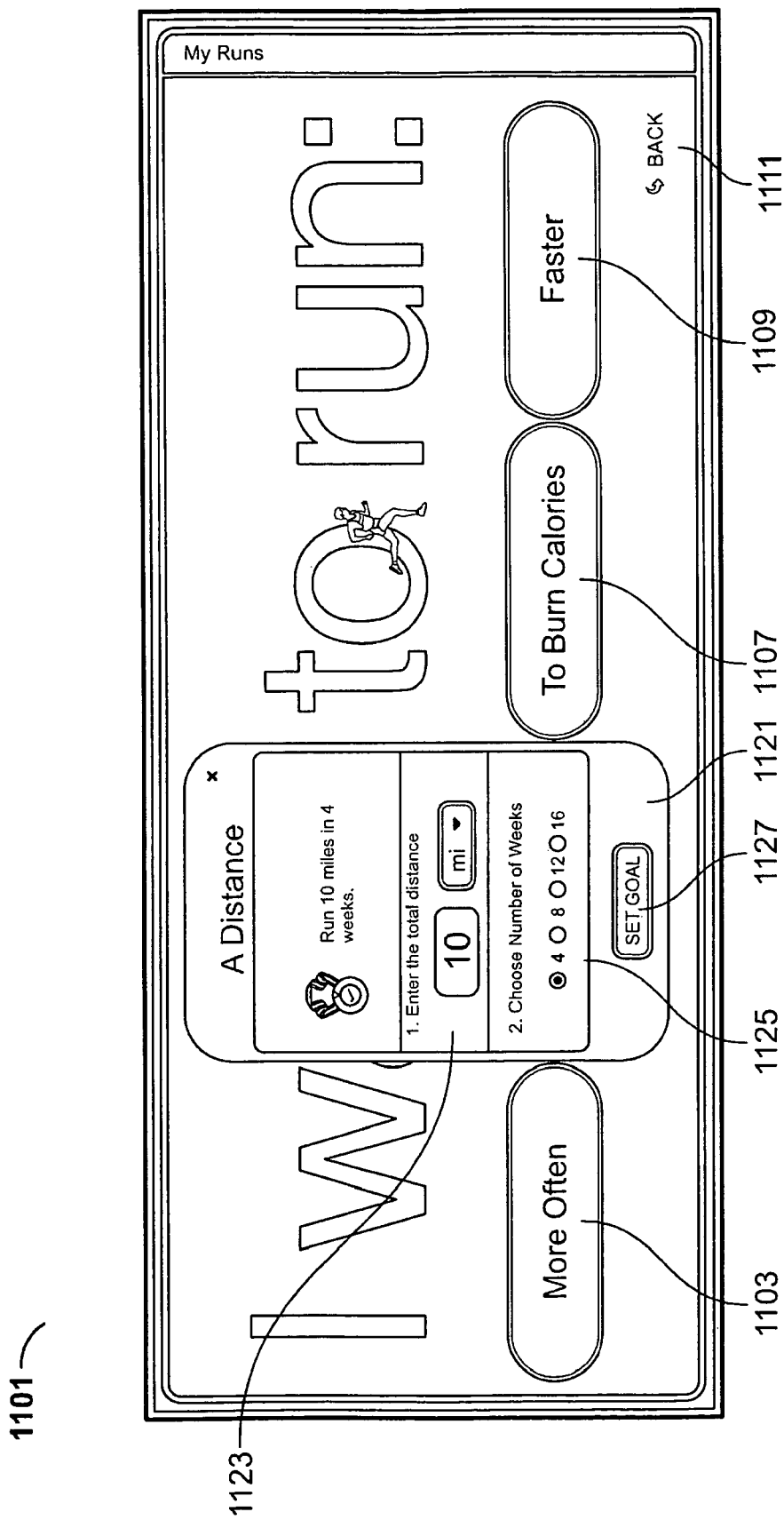

Similarly, if a user wishes to run a longer distance in a given time period, then the user activates the "Distance" button 1105. In response, the athletic data display configuration module 605 reconfigures the user interface 1101 to include a sub-interface 1121. As seen in FIG. 11C, the sub-interface 1121 includes a "Total Distance" control 1123, a "Number Of Weeks" control 1125, and a "Set Goal" button 1127. By employing the "Total Distance" control 1123, a user can specify the total distance he or she wishes to run within a desired time period. Similarly, by employing the "Number Of Weeks" control 1125, a user can specify the number of weeks making up the desired time period allowed to reach the desired goal. In the illustrated example, the "Total Distance" control 1123 is a combination control, with both a field control (i.e., a field in which a value can be typed) and a drop down menu control (i.e., to allow the user to select the units in which the distance would be measure). The "Number Of Weeks" control 1125 illustrated in FIG. 11C then is a radio control. Various examples of the invention, however, may employ alternate types of controls as desired. Once a user has specified the number of runs that must be made and specified the time period in which they must be made to meet a desired goal, the user can finalize the goal parameters by activating the "Set Goal" button 1127.

Figure 11D:
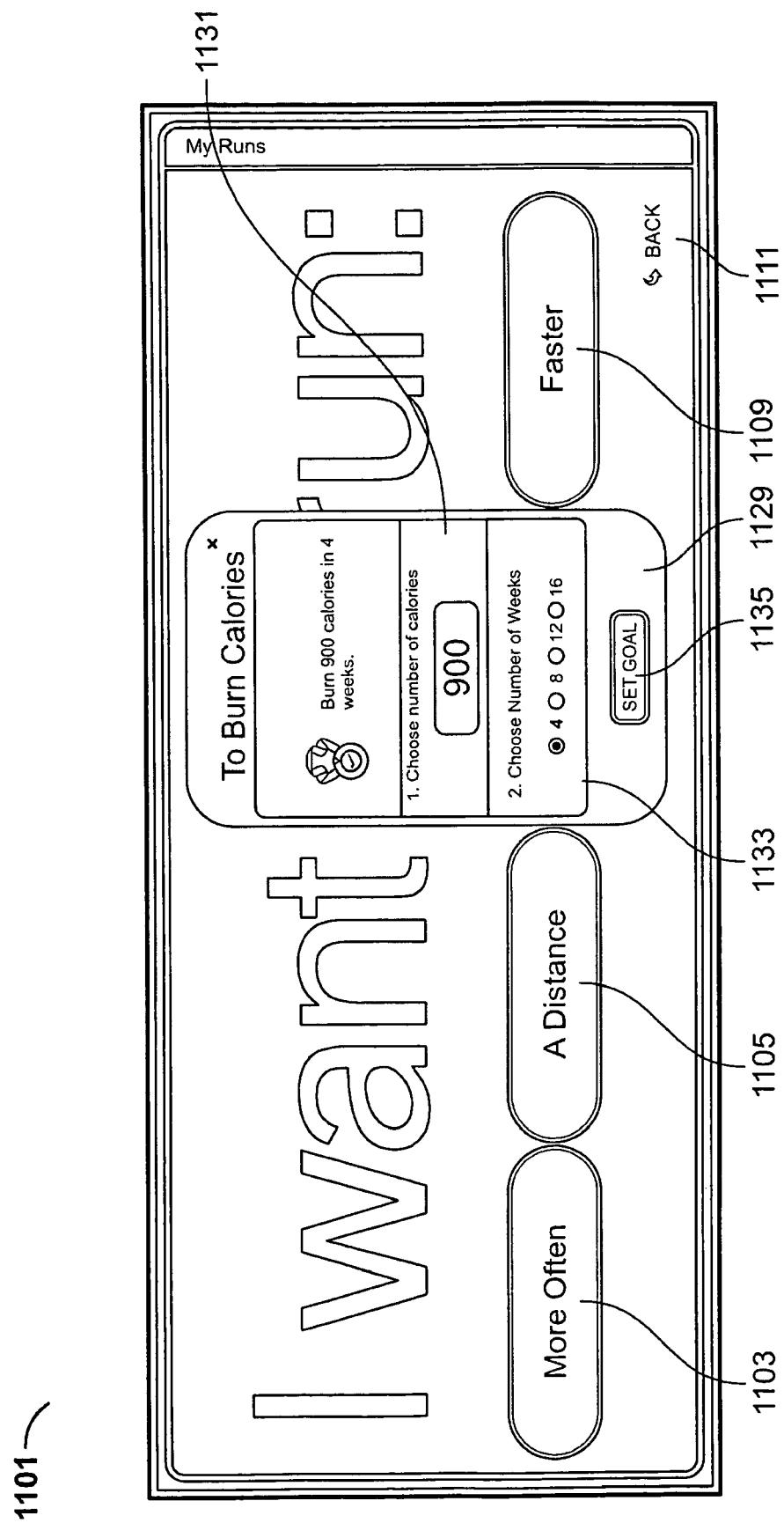

If a user wishes to burn more calories during a particular time period, then the user activates the "Burn More Calories" button 1107. In response, the athletic data display configuration module 605 reconfigures the user interface 1101 to include a sub-interface 1129. As seen in FIG. 11D, the sub-interface 1129 includes a "Number Of Calories" control 1131, a "Number Of Weeks" control 1133, and a "Set Goal" button 1135. By employing the "Number Of Calories" control 1131, a user can specify the number of calories he or she wishes to burn within a desired time period. Similarly, by employing the "Number Of Weeks" control 1133, a user can specify the number of weeks making up the desired time period allowed to burn the desired number of calories. In the illustrated example, the "Number Of Calories" control 1131 is a field control (i.e., having a field in which a value can be typed in) while the "Number Of Weeks" control 1133 is a radio control, but various examples of the invention may employ alternate types of controls as desired. Once a user has specified the number of runs that must be made and specified the time period in which they must be made to meet a desired goal, the user can finalize the goal parameters by activating the "Set Goal" button 1135.

Lastly, if a user wishes to run faster for a desired number of runs, then the user activates the "Faster" button 1109. In response, the athletic data display configuration module 605 reconfigures the user interface 1101 to include a sub-interface 1137. As seen in FIG. 11E, the sub-interface 1137 includes an "Average Pace" control 1139, a "Number Of Runs" control 1141, and a "Set Goal" button 1143. By employing the "Average Pace" control 1139, a user can specify the minimum pace at which he or she wishes to travel for the desired number of runs. Similarly, by employing the "Number Of Runs" control 1141, a user can specify the number of runs for which the user wishes to run faster in order to reach the desired goal. In the illustrated example, the "Average Pace" control 1139 is a field control (i.e., having fields in which values can be typed) while the "Number Of Runs" control 1141 is a radio control, but various examples of the invention may employ alternate types of controls as desired. Once a user has specified the average pace and the number of runs for which he or she must run at or faster than the specified average pace to meet a desired goal, the user can finalize the goal parameters by activating the "Set Goal" button 1143.

After the user has specified a desired goal, the athletic data display configuration module 605 will monitor the athletic data collected by the athletic data collection module 505. When the user subsequently wishes to view his or her progress toward accomplishing the specified goals (by, e.g., selecting the "Goals" tab), then the athletic data display configuration module 605 will aggregate the relevant data from the collected athletic data set and configure a user interface graphically displaying the user's progress toward the specified goals. For example, with some implementations of the invention, the athletic data display configuration module 605 may configure a user interface displaying bar graph, such as the bar graph 1201 shown in FIG. 12. A portion of the bar graph corresponding to the user's progress is marked with fill 1203. Thus, in the illustrated example, the fill 1203 in the bar graph 1203 indicates that the user has accomplished more than 50% of the athletic activity required to complete his or her goal. Some implementations may simultaneously display a bar graph or other progress indicator for each goal set by the user. Still other implementations of the invention may provide controls to allow a user to select a single bar graph or other progress indicator for display in the user interface.

Display of Other User's Athletic Data

Challenges

Figure 13A:
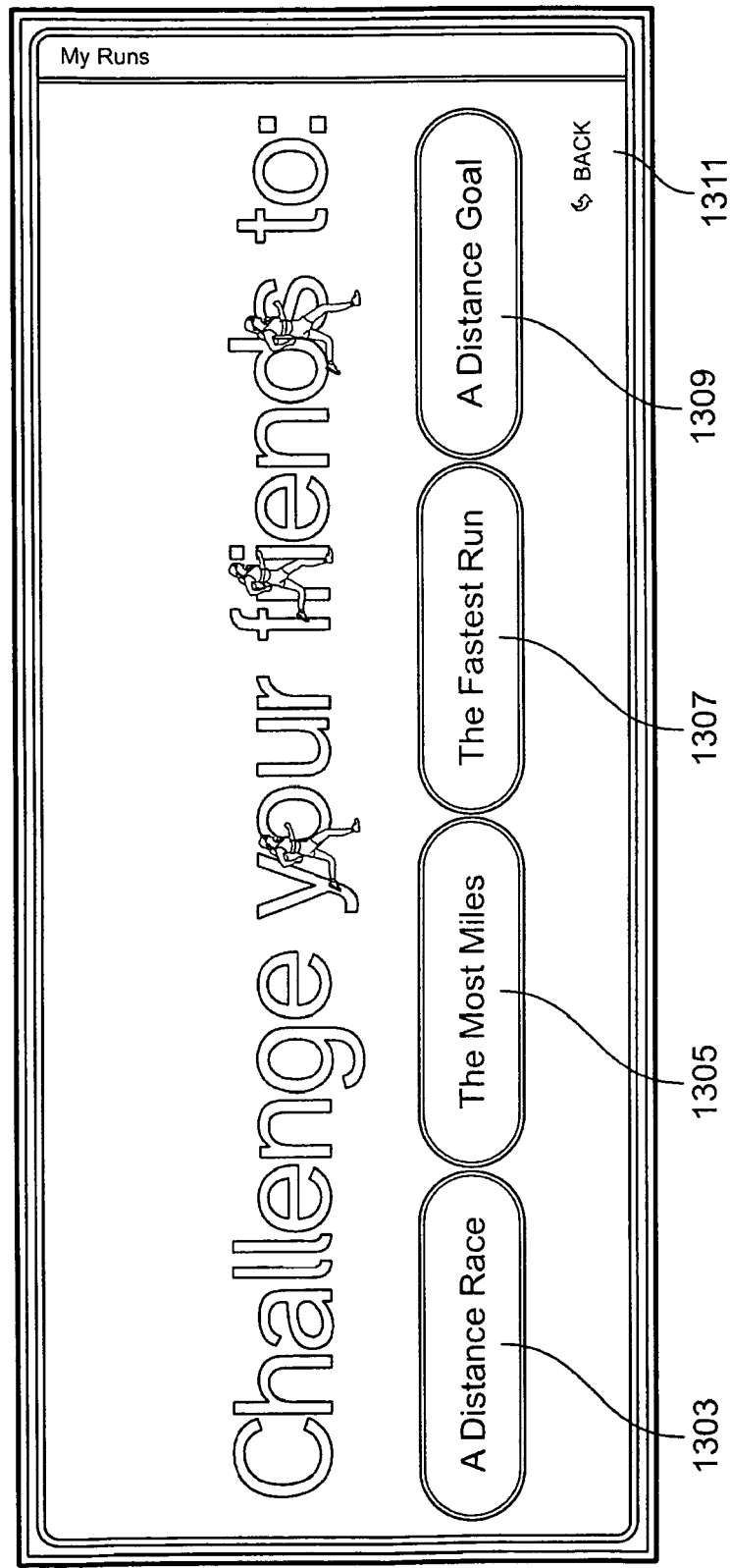
FIGS. 13A-13F illustrate examples of user interfaces that may be provided to create a challenge to other users according to various implementations of the invention.

Various examples of the invention may allow a user to "challenge" one or more other users (i.e., athletes employing embodiments of the invention) to a competition regarding athletic activities. With some implementations of the invention, for example, a user may issue a challenge to one or more other athletes by requesting the user interface 1301 shown in FIG. 13A. As seen in this figure, the interface 1301 includes a "Distance Race" button 1303, a "Most Miles" button 1305, a "Fastest Run" button 1307, a "Distance Goal" button 1309, and a "Back" button 1311. As known in the art, activating the "Back" button 1311 will cause the athletic data display configuration module 605 (or, with some examples of the invention, the athletic data display module 509) to configure and display the previously displayed configuration of the user interface 1301, or if the currently displayed configuration of the user interface 1301 is its initial configuration, a previously-shown user interface.

Figure 13B:
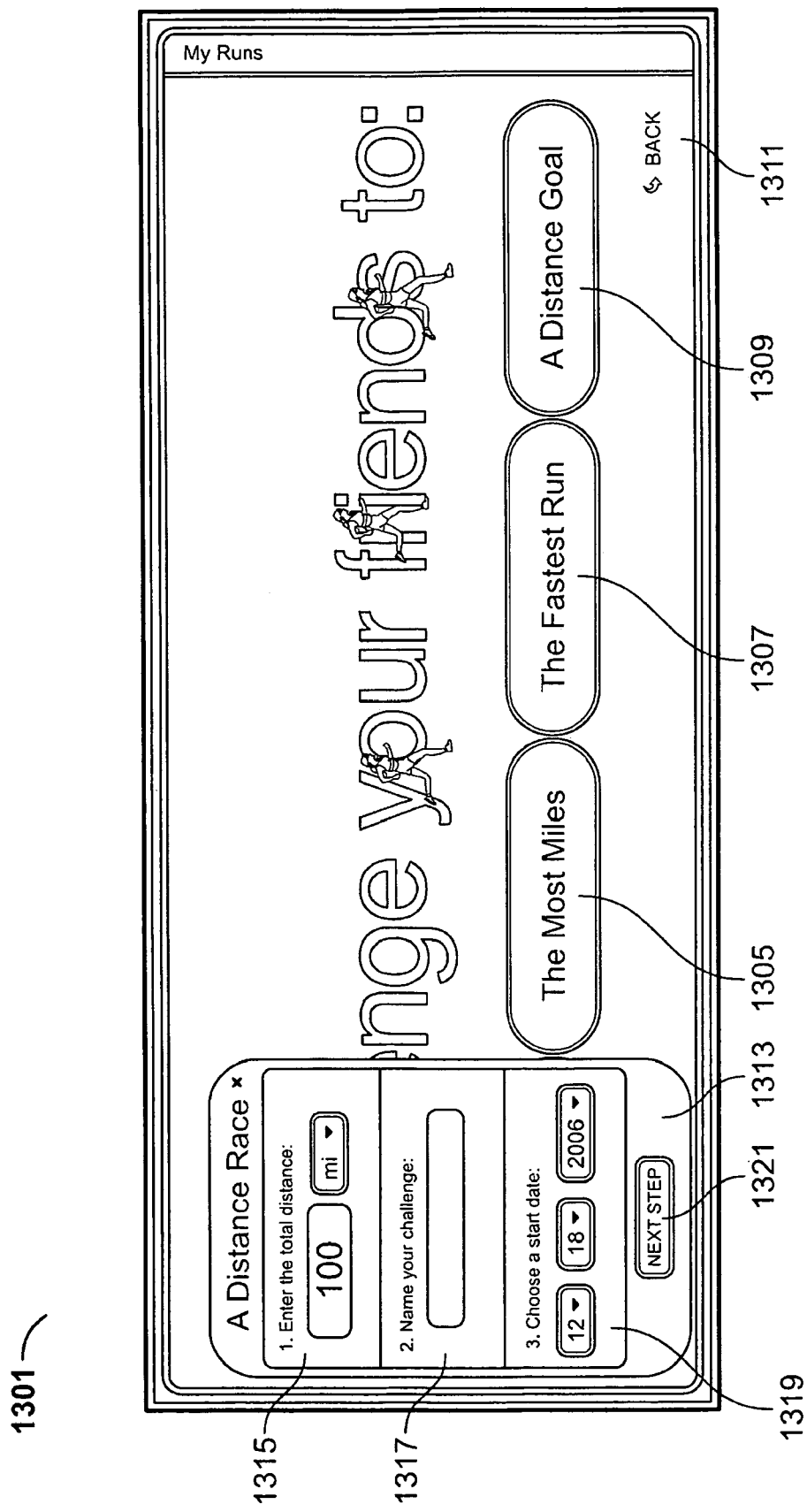

If a user wishes to establish a challenge regarding who can run a specified distance first, then the user activates the "Distance Race" button 1303. In response, the athletic data display configuration module 605 reconfigures the user interface 1301 to include a sub-interface 1313. As seen in FIG. 13B, the sub-interface 1313 includes a "Total Distance" control 1315, a "Challenge Name" control 1317, a "Start Date" control 1319, and a "Next Step" button 1321. By employing the "Total Distance" control 1315, a user can specify the total distance that a challenge participant must be the first to run in order to win the challenge. Next, the user can provide a specific name for the challenge using the "Challenge Name" control 1317. Naming each challenge allows an athlete to identify and keep track of a plurality of different challenges in which he or she may be concurrently participating. The user can then specify the starting date for the challenge using the "Start Date" control 1319. In the illustrated example, the "Total Distance" control 1315 and the "Challenge Name" control 1317 are each field controls (i.e., controls having a field in which a value can be typed), while the "Start Date" control 1319 is made up of a number of drop-down menus. It should be appreciated, however, that various examples of the invention may employ alternate types of controls as desired. Once a user has specified the parameters of the challenge, the user can begin the process of inviting specific athletes to participate in the challenge by activating the "Next Step" button 1321.

Figure 13C:
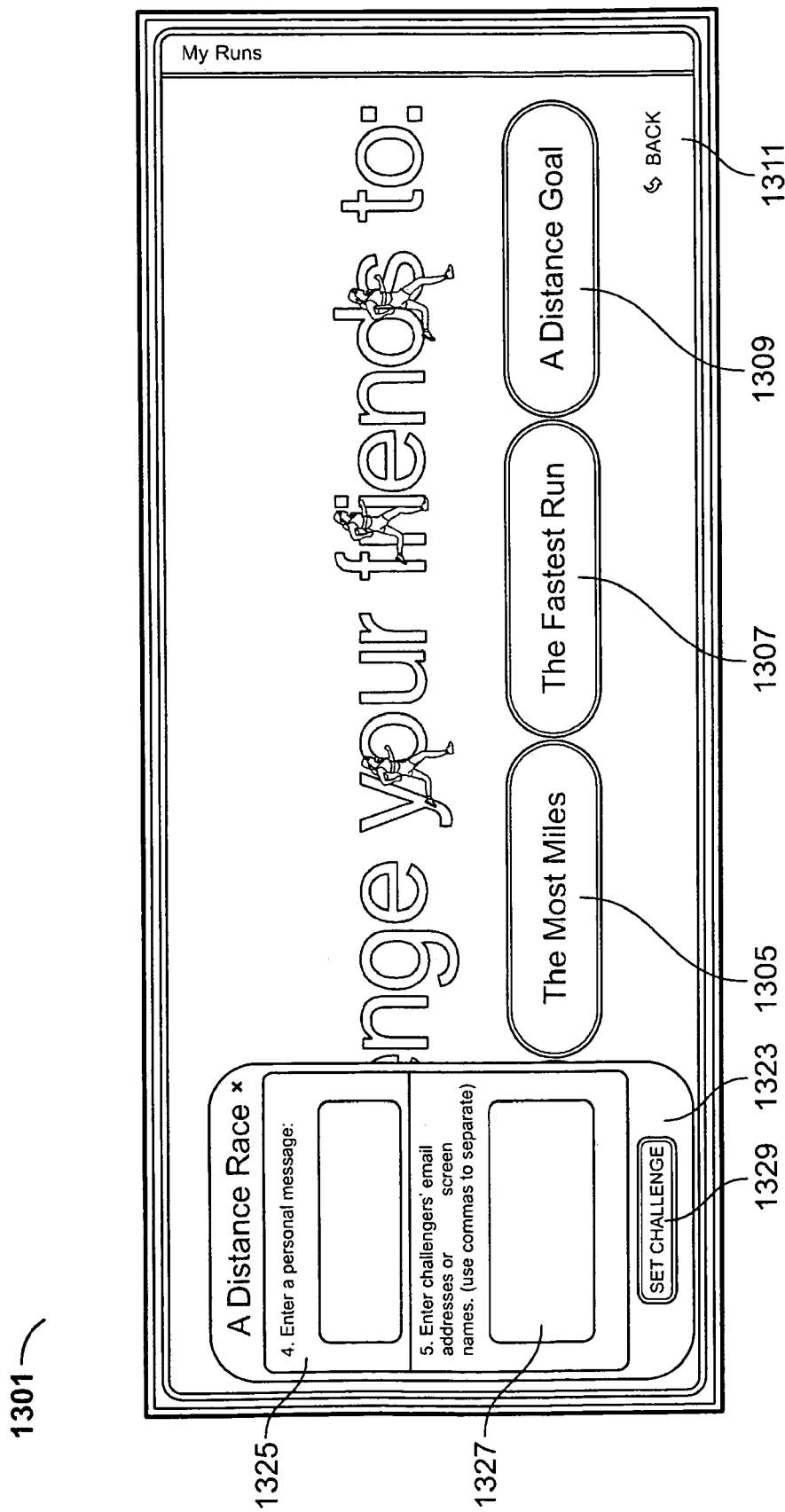

When the user activates the "Next Step" button 1321, the athletic data display configuration module 605 reconfigures the user interface 1301 to include a sub-interface 1323 in place of the "Distance Race" button 1303, as shown in FIG. 13C. As seen in this figure, the sub-interface 1323 includes a "Personal Message" control 1325, an "Email Address" control 1327, and a "Set Challenge" button 1329. The user can employ the "Personal Message" control 1325 to create a personal message to each athlete the user wishes to invite to participate in the challenge. Using the "Email Address" control 1327, the user can then specify the email address for each person he or she wishes to invite to participate in the challenge. In the illustrated example, the "Personal Message" control 1325 and the "Challenge Name" control 1317 are each field controls (i.e., controls having a field in which a value can be typed), but various examples of the invention may employ alternate types of controls as desired.

Once the user has provided the email address for each desired participant, the user can initiate the challenge by activating the "Set Challenge" button 1329. In response to the user activating the "Set Challenge" button 1329, the athletic data display configuration device 601 (or, with some implementations of the invention, the user's athletic information collection and display device 501) sends an email to each of the specified invitees. The email will contain the personal message and, e.g., an interactive prompt to join the challenge. If an invitee agrees to join the challenge by responding to the prompt, then the athletic data display configuration device 601 will be notified that the invitee has agreed to join the challenge. These types of email interactive prompts (such as the "voting" buttons provided in versions of the Outlook software tool available from Microsoft Corporation of Redmond, Wash.) are well known in the art, and will not be discussed here in detail.

After the athletic data display configuration device 601 has identified the participants in a challenge, it monitors the collected athletic data for each of the participants, and aggregates the relevant data values in the collected athletic data. For example, if the challenge is a race to determine who can be the first to run 100 miles, for each participant the athletic data display configuration device 601 will sum the total distance value in each athletic data set collected for that participant after the start date. When a participant has a sum of his or her total distance values that matches or exceeds the specified challenge distance (and is the first invitee to do so), then the athletic data display configuration device 601 will identify that participant as the winner of the challenge. In response, the athletic data display configuration device 601 will notify each participant of the winner. The athletic data display configuration device 601 may notify the participants using any desired technique, such as by sending an electronic mail message, by displaying a special-purpose interface when each participant connects to the athletic data display configuration device 601, etc. A variety of such notification techniques are well known in the art, and thus will not be discussed in detail.

With various examples of the invention, the athletic data display configuration device 601 may additionally provide updates regarding the status of a participant relative to the other participants. These updates also can be provided using any desired technique, such as by sending an electronic mail message, by displaying a special-purpose interface when each participant connects to the athletic data display configuration device 601, etc. For example, the athletic data display configuration device 601 may configure and provide a user interface showing each participant's progress toward the goal of the challenge using, e.g., bar graphs for each participant of the type previously described with regard to monitoring individual goals.

Figure 13D:
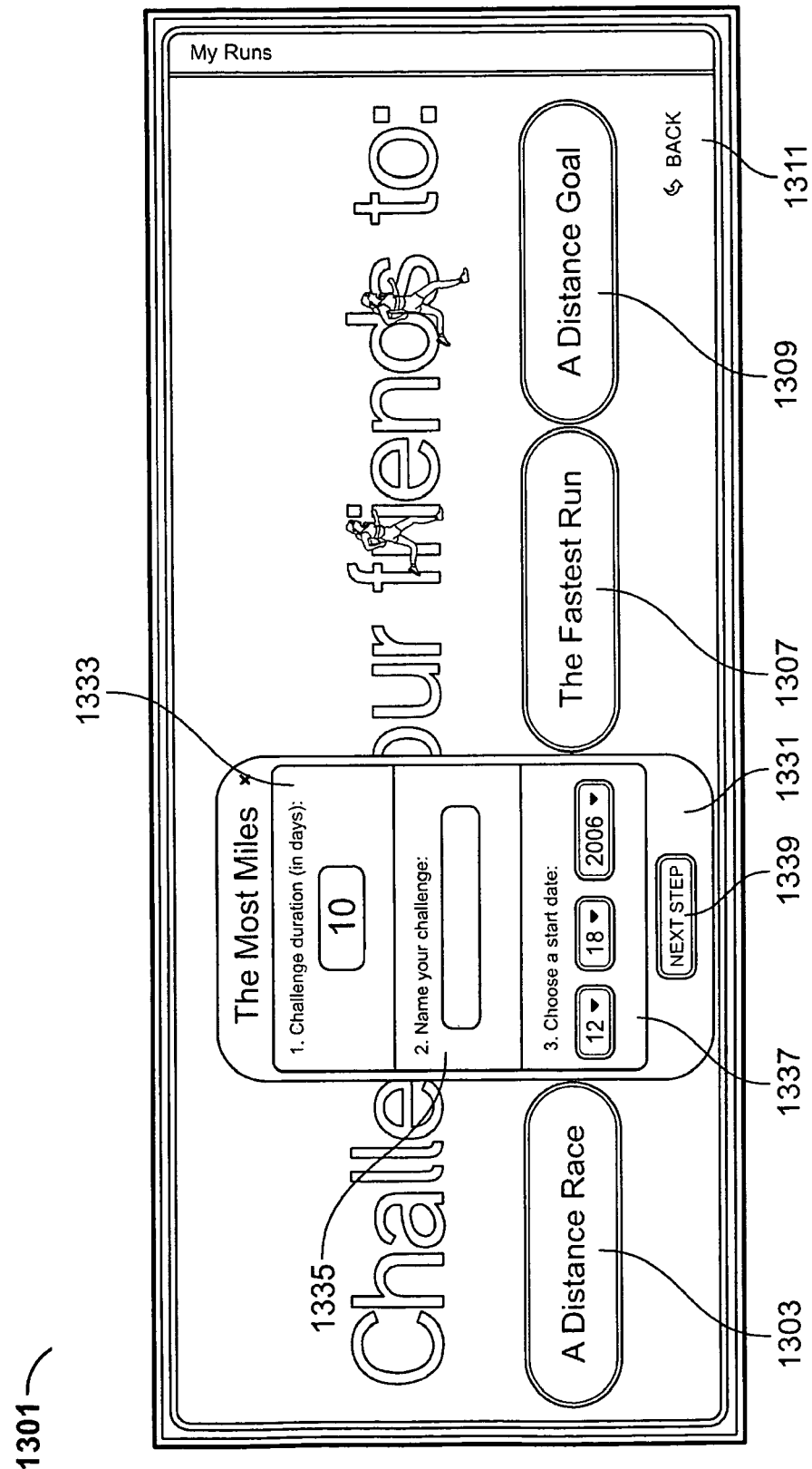

Returning now to FIG. 13A, if a user wishes to establish a challenge regarding who can run the most miles in a given period of time, then the user activates the "Most Miles" button 1305. In response, the athletic data display configuration module 605 reconfigures the user interface 1301 to include a sub-interface 1331, as seen in FIG. 13D. The sub-interface 1331 includes a "Challenge Duration" control 1333, a "Challenge Name" control 1335, a "Start Date" control 1337, and a "Next Step" button 1339. By employing the "Challenge Duration" control 1333, a user can specify the total amount of time for which a challenge participant has to run the greatest total distance in order to win the challenge. Next, the user can provide a specific name for the challenge using the "Challenge Name" control 1335. The user can then specify the starting date for the challenge using the "Start Date" control 1337. In the illustrated example, the "Challenge Duration" control 1333 and the "Challenge Name" control 1335 are each field controls (i.e., controls having a field in which a value can be typed), while the "Start Date" control 1337 is made up of a number of drop-down menus. It should be appreciated, however, that various examples of the invention may employ alternate types of controls as desired.

Once a user has specified the parameters of the challenge, the user can begin the process of inviting specific athletes to participate in the challenge by activating the "Next Step" button 1339. In response, the athletic data display configuration module 605 reconfigures the user interface 1301 to include the sub-interface 1323 in place of the "Most Miles" button 1305. (An example of sub-interface 1323 is illustrated in FIG. 13C.) As discussed in detail above, the user can employ the sub-interface 1323 to invite others to participate in the challenge, and ensure that the athletic data display configuration device 601 is informed of the participants in the challenge. As also previously discussed, the athletic data display configuration device 601 will monitor the collected athletic data for each participant, and aggregate the relevant data values from the collected athletic data to determine who wins the challenge. Still further, the athletic data display configuration device 601 can notify the participants of the winner of the challenge, and, with various examples of the invention, of the status of each participant during the challenge as described above.

Figure 13E:
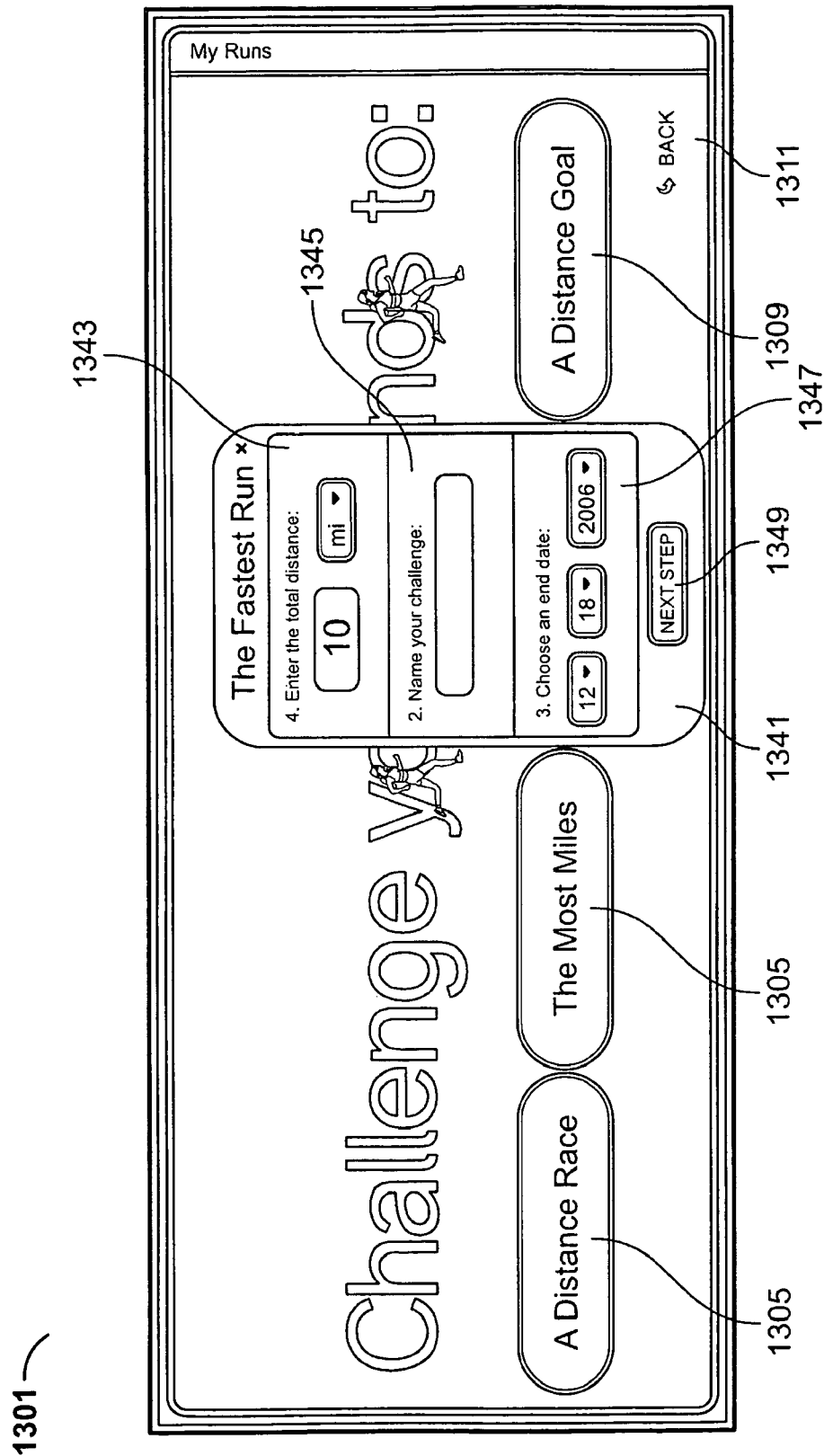

If a user wishes to establish a challenge regarding who can make the fastest run in a given period of time, then the user activates the "Fastest Run" button 1307. In response, the athletic data display configuration module 605 reconfigures the user interface 1301 to include a sub-interface 1341 as seen in FIG. 13E. The sub-interface 1341 includes a "Total Distance" control 1343, a "Challenge Name" control 1345, a "Start Date" control 1347, and a "Next Step" button 1349. By employing the "Total Distance" control 1343, a user can specify the total distance a user must run in order to have his or her run time eligible to win the challenge. Next, the user can provide a specific name for the challenge using the "Challenge Name" control 1345. The user can then specify the starting date for the challenge using the "Start Date" control 1347. In the illustrated example, the "Total Distance" control 1343 and the "Challenge Name" control 1345 are each field controls (i.e., controls having a field in which a value can be typed), while the "Start Date" control 1347 is made up of a number of drop-down menus, but various examples of the invention may employ alternate types of controls as desired.

Once a user has specified the parameters of the challenge, the user can begin the process of inviting specific athletes to participate in the challenge by activating the "Next Step" button 1349. In response, the athletic data display configuration module 605 reconfigures the user interface 1301 to include a sub-interface 1323 in place of the "Fastest Run" button 1307. (An example of sub-interface 1323 is illustrated in FIG. 13C.) As discussed in detail above, the user can employ the sub-interface 1323 to invite others to participate in the challenge, and ensure that the athletic data display configuration device 601 is informed of the participants in the challenge. As also previously discussed, the athletic data display configuration device 601 will monitor the collected athletic data for each participant, and aggregate the relevant data values from the collected athletic data to determine who wins the challenge. Still further, the athletic data display configuration device 601 can notify the participants of the winner of the challenge, and, with various examples of the invention, of the status of each participant during the challenge as described above.

Figure 13F:
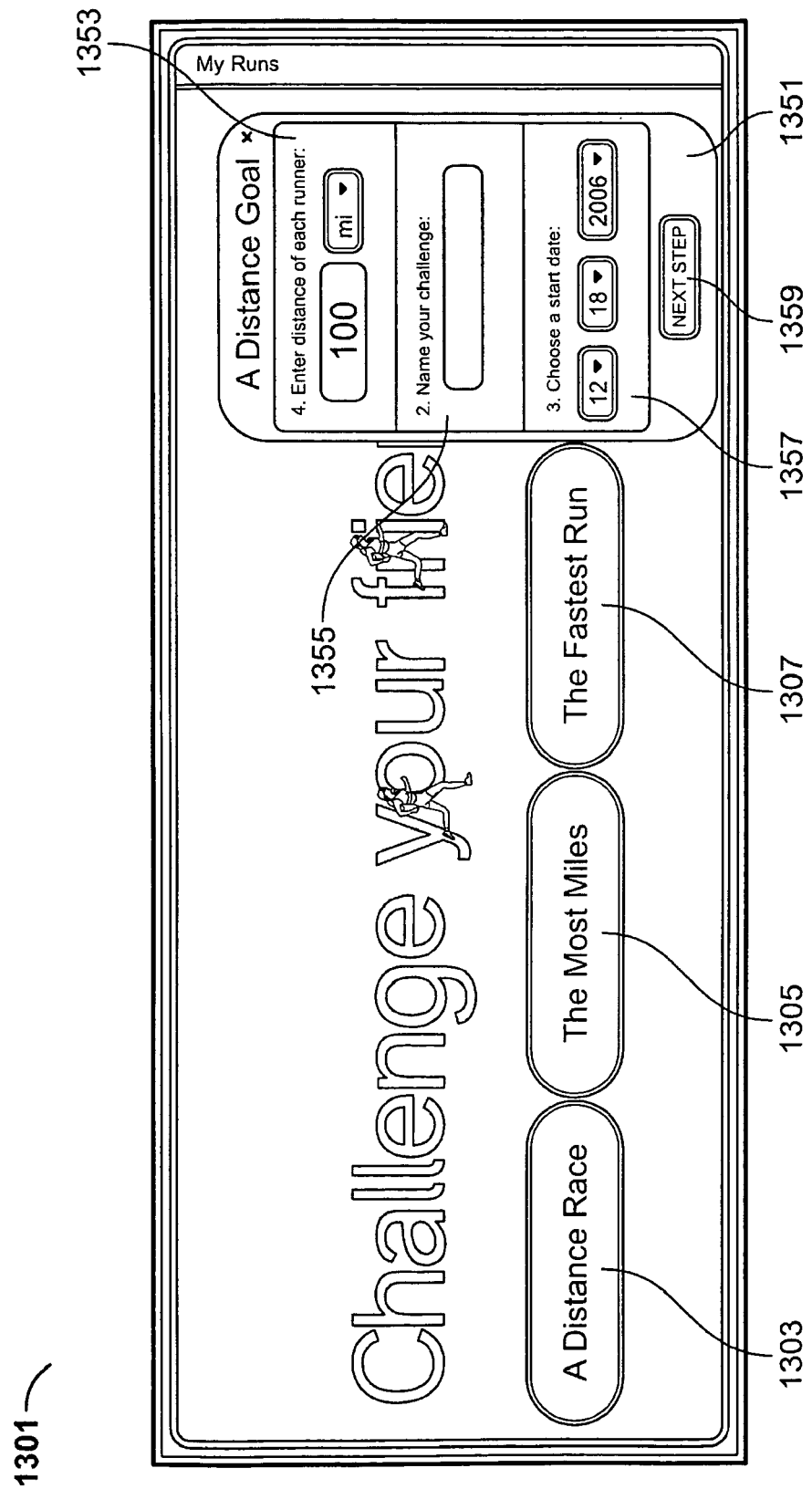

Lastly, if a user wishes to establish a challenge regarding who can run a specified distance in a given period of time, then the user activates the "Distance Goal" button 1309. In response, the athletic data display configuration module 605 reconfigures the user interface 1301 to include a sub-interface 1351. As seen in FIG. 13F, the sub-interface 1351 includes a "Total Distance" control 1353, a "Challenge Name" control 1355, a "Start Date" control 1357, and a "Next Step" button 1359. By employing the "Total Distance" control 1353, a user can specify the total distance a user must run over the specified time period in order to meet the challenge. Next, the user can provide a specific name for the challenge using the "Challenge Name" control 1355. The user can then specify the starting date for the challenge using the "Start Date" control 1357. In the illustrated example, the "Total Distance" control 1353 and the "Challenge Name" control 1355 are each field controls (i.e., controls having a field in which a value can be typed), while the "Start Date" control 1357 is made up of a number of drop-down menus, but various examples of the invention may employ alternate types of controls as desired.

Once a user has specified the parameters of the challenge, the user can begin the process of inviting specific athletes to participate in the challenge by activating the "Next Step" button 1359. In response, the athletic data display configuration module 605 reconfigures the user interface 1301 to include the sub-interface 1323 in place of the "Distance Goal" button 1309. (An example of sub-interface 1323 is illustrated in FIG. 13C.) As discussed in detail above, the user can employ the sub-interface 1323 to invite others to participate in the challenge, and ensure that the athletic data display configuration device 601 is informed of the participants in the challenge. As also previously discussed, the athletic data display configuration device 601 will monitor the collected athletic data for each participant, and aggregate the relevant data values from the collected athletic data to determine who wins the challenge. Still further, the athletic data display configuration device 601 can notify the participants of the winner of the challenge, and, with various examples of the invention, of the status of each participant during the challenge as described above.

Lists

As well as interactive comparisons of a user's athletic data with other users, such as the goals and challenges described in detail above, some implementations of the invention may alternately or additionally allow a user to passively compare his or her athletic data with other users. For example, some implementations of the invention may provide a ranking of where a user stands with respect to other users. The ranking may be based upon a simple comparison, or it may be limited to a specific demographic group, a particular geographic region, or some combination therefore.

For example, with some implementations of the invention, a user may request that the athletic data display configuration module 605 generate and display the user interface 1401 illustrated in FIG. 14A. As seen in this figure, the user interface 1401 includes a comparison criteria region 1403, a filter region 1405, and display region 1407. The comparison criteria region 1403 includes a plurality of "radio" style controls 1409, while the filter region 1405 includes a plurality of "drop-down" controls 1411-1413. The display region 1407 then displays user information based upon athletic data selected using the comparison and filter information selected using the controls 1409-1413.

More particularly, a user employs the "radio" style controls 1409 to specify the basic criteria according to which the athletic data display configuration module 605 will compare athletic data for a plurality of users. These controls 1409 are referred to herein as "radio" style controls because the selection of one of the controls (e.g., control 1409C) will automatically deselect a previously selected control, and only one control may be selected at any given time. Of course, it should be appreciated that other type of selection tools, including other types of controls, may be alternately or additionally employed with other implementations of the invention. Each control 1409 is associated with both a sorting criterion for sorting measured athletic data and a time criterion specifying a time period during which the athletic data being compared must have been measured. For example, each of controls 1409A-1409C is associated with total distance as a sorting criterion, while control 1409A is associated with a week time period, control 1409B is associated with a month time period, and control 1409C is associated with an unlimited time period. Control 1409D is then associated with a duration sorting criterion and a week time period.

With the example of the interface 1401 shown in FIG. 14A, each of the filter controls 1411-1415 are selected to "ALL," as will be discussed in more detail below. Further, the control 1409A is selected. Because the control 1409A is associated with the "distance" sorting criterion and the "week" time criterion, the athletic data display configuration module 605 will sort the aggregated distance data for participating users that was measured during the preceding week. It then lists the names of the participating users having the ten highest aggregated distance data values in the filter region 1405. In addition, the athletic data display configuration module 605 will display in the aggregated distance data values measured during the preceding week for each of the identified participating users. Still further, the athletic data display configuration module 605 will display the user's corresponding aggregated distance measured for the preceding week. With some implementations of the invention, the athletic data display configuration module 605 also may display the ranking of the user's corresponding aggregated distance information measured for the preceding week relative to those participating users having a greater aggregated distance measured for the preceding week. Thus, in the illustrated example, the user "Rauchholz" has a ranking of 2932 relative to other participating users.

With some implementations of the invention, the participating users will be any user who provides athletic data to the athletic data storage 607 (or to an affiliated athletic data storage). For still other implementations of the invention, however, the participating users may be a subset of the all of the users who provide athletic data to the athletic data storage 607 or to an affiliated athletic data storage. For example, the participating users may be only those users who agree in advance to have their data shared with other users, or those users who do not specifically indicate that they wish for their athletic data to be private. Of course, still other criteria may be used to determine which users will be treated as participating users.

FIG. 14B illustrates another example of the interface 1401. Again, each of the filter controls 1411-1415 are selected to "ALL." Further, the control 1409E is selected, which is associated with the "duration" sorting criterion and the "month" time criterion. Accordingly, the athletic data display configuration module 605 will sort the aggregated running (or walking) duration data for participating users that was measured during the preceding month. It then lists the names of the participating users having the ten highest aggregated duration data values in the filter region 1405. In addition, the athletic data display configuration module 605 will display in the aggregated duration data values measured during the preceding month for each of the identified participating users. Still further, the athletic data display configuration module 605 will display the user's corresponding aggregated duration data measured for the preceding month. Again, the athletic data display configuration module 605 also displays the ranking of the user's corresponding aggregated duration data measured for the preceding month relative to those participating users having a greater aggregated duration value measured for the preceding month. Thus, in the illustrated example, the user "Rauchholz" has a ranking of 28636 relative to other participating users.

Figure 14C:
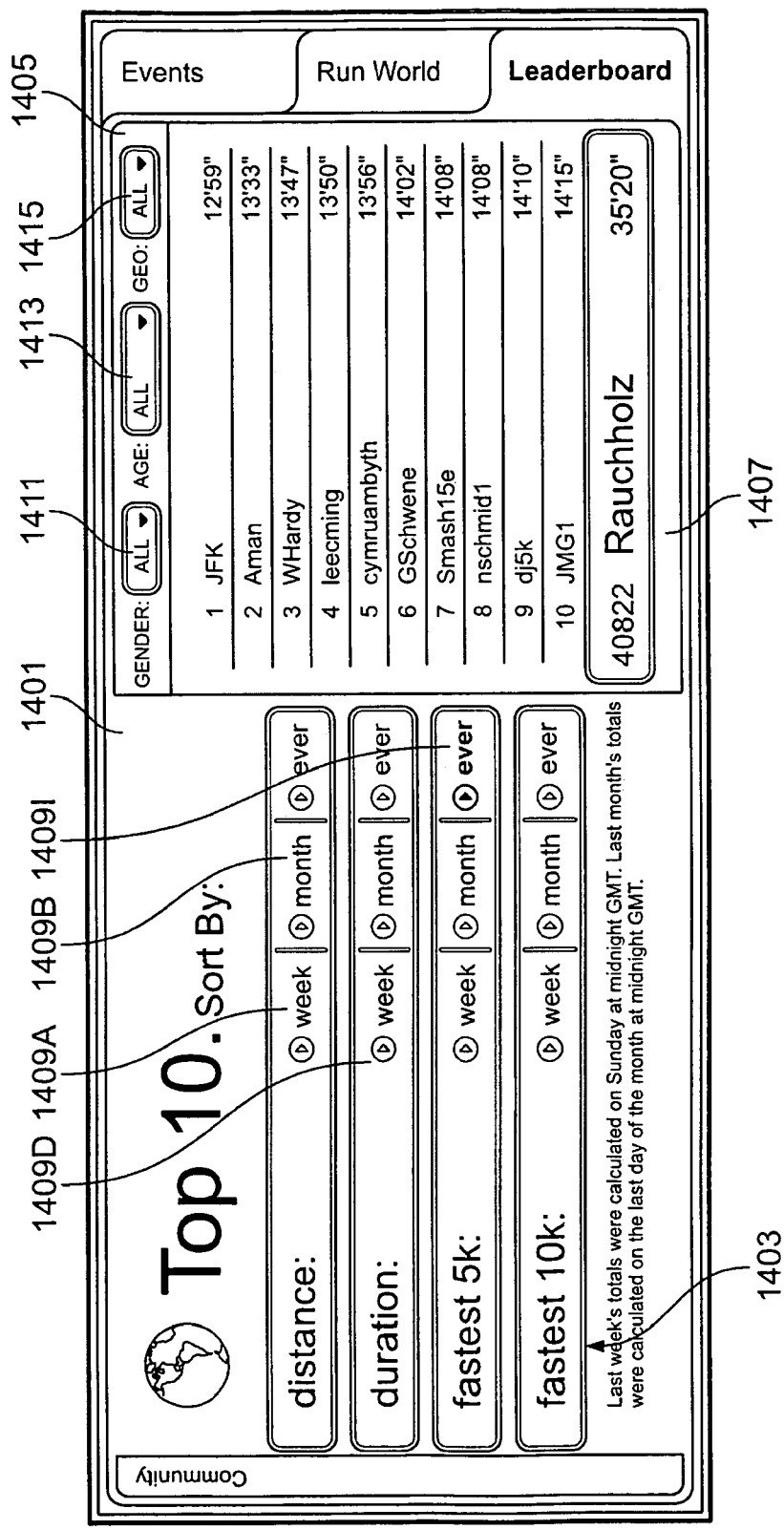

FIG. 14C illustrates yet another example of the interface 1401. Again, each of the filter controls 1411-1415 are selected to "ALL." Further, the control 14091 is selected, which is associated with the "fastest 5 k" sorting criterion and the "ever" time criterion. Accordingly, the athletic data display configuration module 605 will identify and display the participating users with the ten fastest travel times for a 5 k run that was measured at any time preceding the user's selection of the control 14091. In addition, the athletic data display configuration module 605 will display in the fastest 5 k time value for each of the identified participating users. Still further, the athletic data display configuration module 605 will display the user's fastest measured time for a 5 k run, together with a ranking of that time relative to those participating users having a faster measured time for a 5 k run. Thus, in the illustrated example, the user "Rauchholz" has a ranking of 40822 relative to other participating users.

Figure 14E:
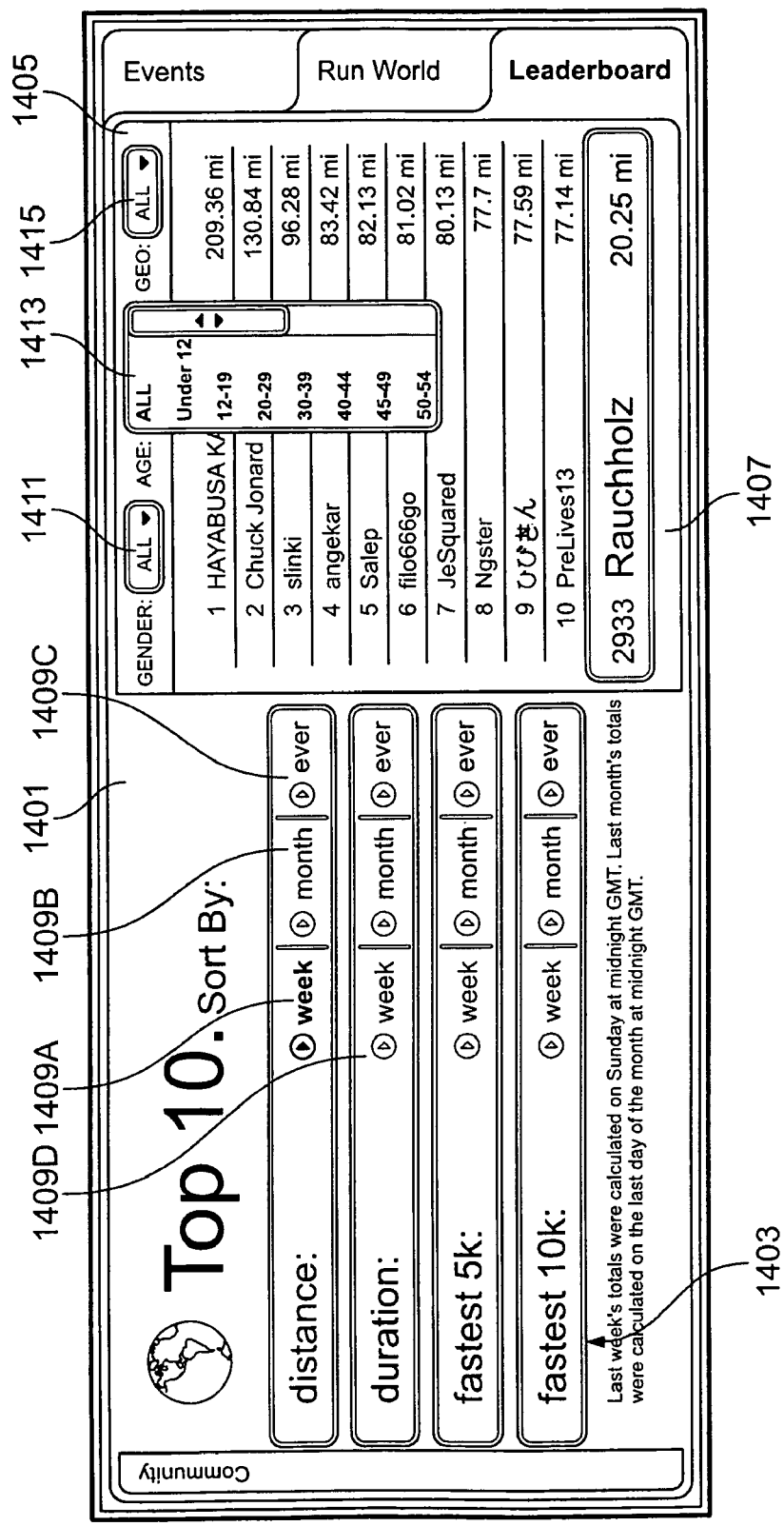
Figure 14F:
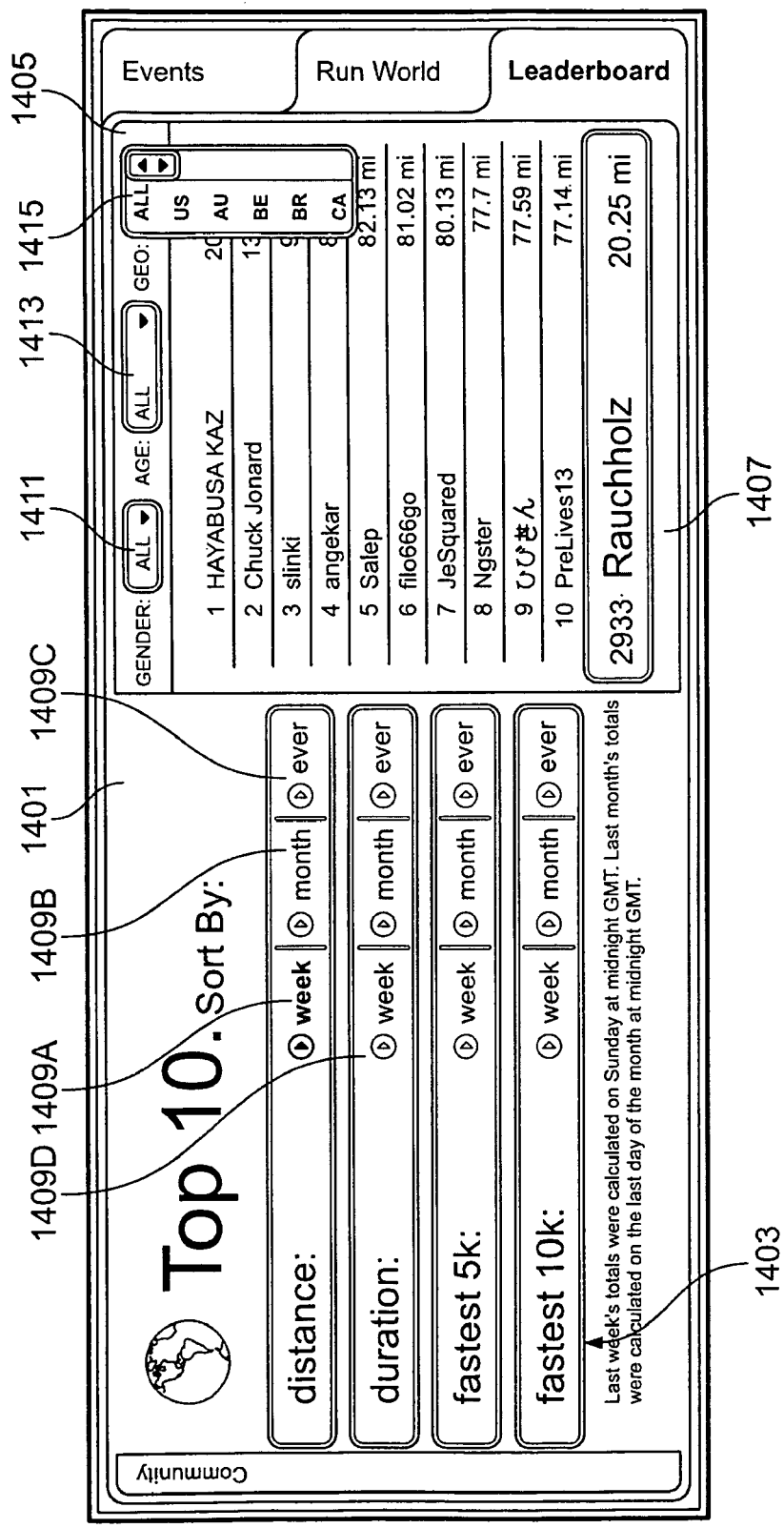

In some situations, a user may wish to limit the pool of participating users to whom the user will be compared. As previously noted, the filter region 1405 includes filter controls 1411-1415. These filter controls may be employed to limit the participating users that will be considered for a desired comparison. For example, as illustrated in FIG. 14D, a user can employ the filter control 1411 to select between including all participating users for comparison, only male participating users for comparison, or only female participating users for comparison. Similarly, as shown in FIG. 14E, a user can employ filter control 1413 to limit the comparison to only those participating users within a desired age group. Still further, as shown in FIG. 14F, a user can employ the filter control 1415 to limit the comparison to participating users within a geographic region.

It should be appreciated that, with some implementations of the invention, a user can employ each of the filters 1411-1415 simultaneously. For example, a user may employ the filter controls 1411-1415 to limit the participating users considered for comparison with the users's athletic data to only men between the ages of 40-44 residing in the United States. The information required to filter the participating users may be obtained from any available source. Conveniently, however, the information may be obtained by requesting the users to submit this information for a user profile during an initial registration process. Of course, while three specific filtering criteria have been disclosed, it should be appreciated that any desired type and/or combination of characteristics be employed as filters.

Other Features

Record of Achievements

As discussed in detail above, various implementations of the invention may provide positive reinforcement to an athlete. For example, as discussed above, a user can employ various embodiments of the invention to set goals for himself or herself, and then track his or her progress toward attaining those goals. Similarly, a user may employ various embodiments of the invention to participate in a challenge. Once the goal is completed or the challenge is won, however, these achievements may be forgotten and thus not provide the user with any further positive reinforcement.

Figure 15:
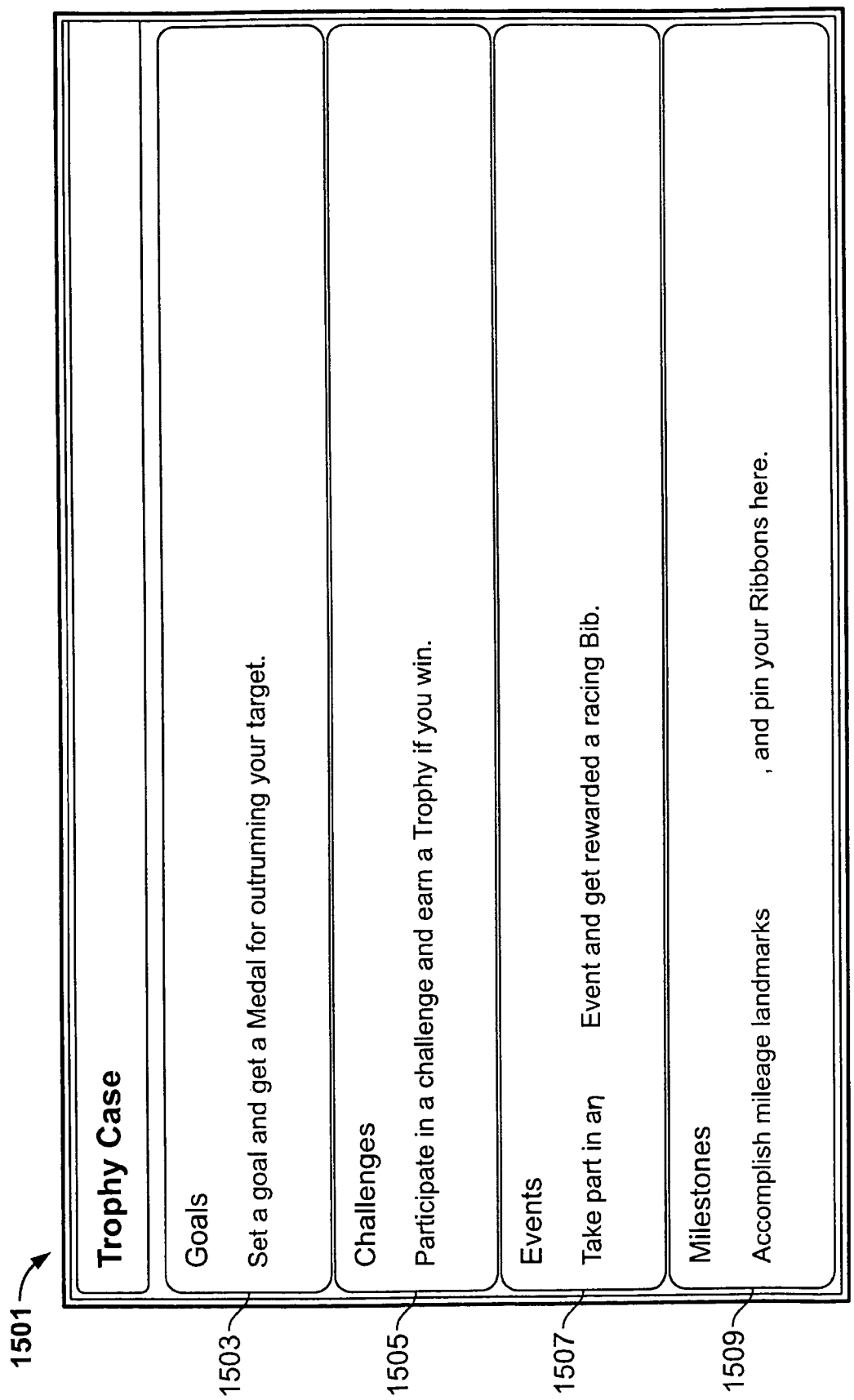
FIG. 15 illustrates an example of a user interface that may be provided to memorialize a user's athletic achievements according to various implementations of the invention.

Accordingly, some implementations of the invention may provide a feature for memorializing a user's various athletic achievements. For example, with some embodiments of the invention, the athletic data display configuration module 605 may provide a user interface, such as the user interface 1501 shown in FIG. 15, for displaying athletic achievements recorded for a user. As seen in this figure, the user interface 1501 includes a "goal" region 1503, a "challenges" region 1505, an "events" region 1507, and a "milestones" region 1509. Each of these regions can be used to display an icon representing a user's previous achievement.

For example, if a user sets and then subsequently meets a goal, the achievement of this goal will be recorded by the athletic data display configuration module 605. In response, the athletic data display configuration module 605 will display an icon, such as a representation of a medal, graphically commemorating that achievement. Similarly, if the user wins a challenge, that achievement will be recorded by the athletic data display configuration module 605. In response, the athletic data display configuration module 605 will display an icon, such as a representation of a trophy, graphically commemorating that achievement.

Still further, a user may participate in an event associated with one or more implementations of the invention. For example, a race sponsor, such as a marathon race sponsor, may affiliate itself with embodiments of the invention. If a user runs in the race, completes the race, or places in the race, then the athletic data display configuration module 605 may record that achievement. In response, the athletic data display configuration module 605 will display an icon, such as a representation of a racing bib, graphically commemorating that achievement. The athletic data display configuration module 605 may employ any desired technique to record the user's participation in the race. For example, the race sponsor may physically monitor the user's participation, and subsequently update the athletic data storage 607 directly. Alternately, the user may update the athletic data storage 607 on an honor system basis.

Of course, still more sophisticated techniques can be used to have the athletic data display configuration module 605 record the user's achievement. For example, the race sponsor or a third party may provide the user with an electronic recording device that records the user's progress through the race. The user can then download the data from the electronic recording device to the athletic data storage 607 or to the athletic data display configuration module 605. With some implementations of the invention, the electronic interface device 205 or the athletic parameter measurement device 207 may even be used to record the user's progress through the race, and to subsequently download the data from the electronic recording device to the athletic data storage 607 or to the athletic data display configuration module 605.

Still further, a user may have still other milestones associated with his or her athletic performance. For example, a user may run achieve a relatively large total distance, such as 100 kilometers, 100 miles, 250 kilometers, 250 miles, etc., run at a particularly fast speed, such as a mile in less than five minutes, or run for a relatively large total duration, such as 1000 hours. In response, the athletic data display configuration module 605 may record that milestone achievement, and then display an icon, such as a representation of an award ribbon, graphically commemorating that achievement.

In this manner, various implementations of the invention can memorialize a user's past achievements to provide the user with positive feedback to inspire future athletic performance. Of course, some implementations of the invention may memorialize alternate or additional achievements.

Resolutions

Figure 16:
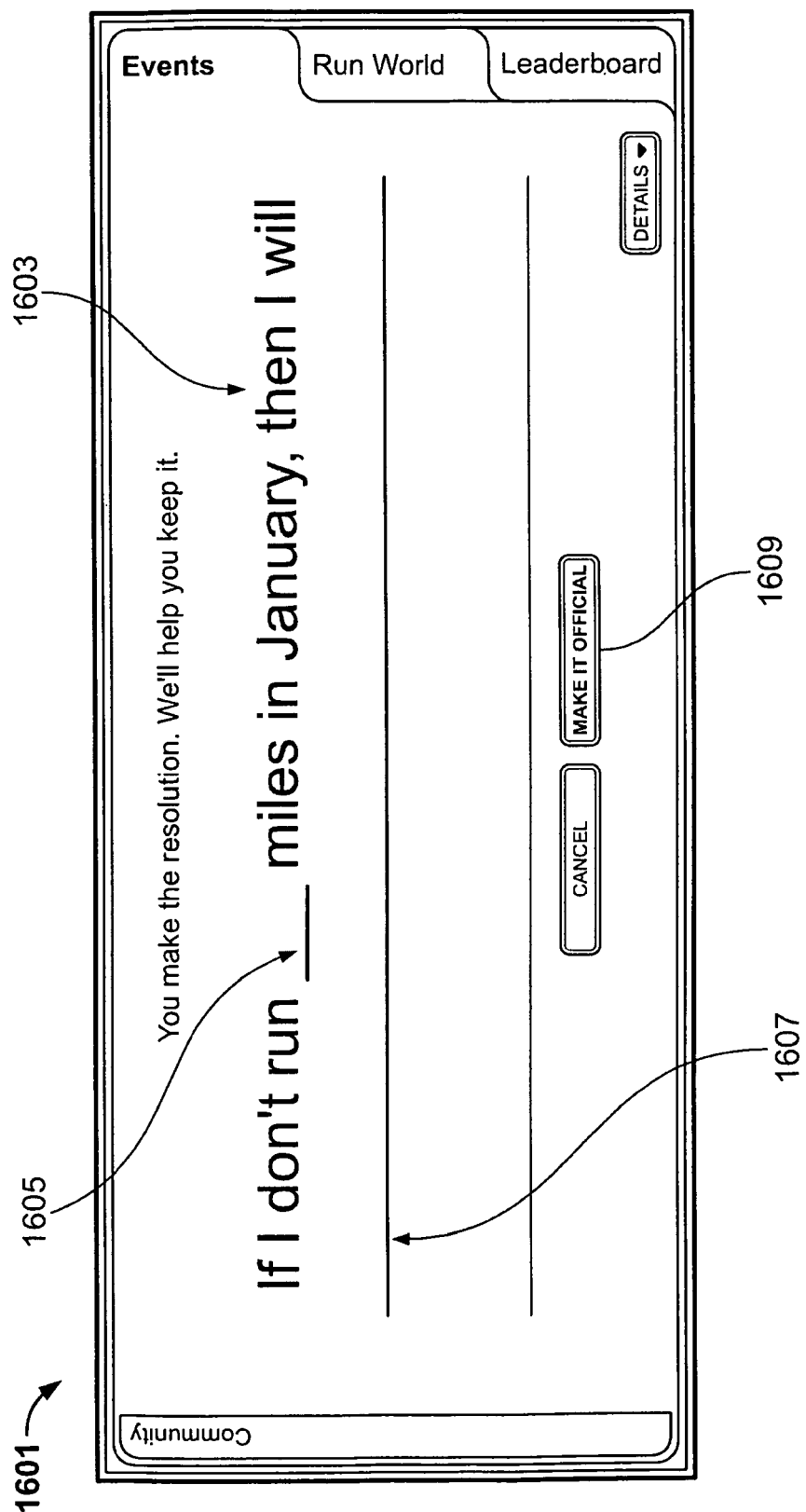
FIG. 16 illustrates an example of a user interface that may be provided to create a resolution to perform an athletic achievement according to various implementations of the invention.

Some implementations of the invention may assist a user in resolving to achieve a specific athletic achievement, and then keep that resolution. For example, various embodiments of the invention may provide a user interface like the user interface 1601 illustrated in FIG. 16. As seen in this figure, the interface 1601 provides a resolution statement 1603 with an achievement field 1605 and a consequence field 1607. The user interface also includes a submission button 1609. When a user wishes to make a resolution, he or she can insert the desired achievement goal (such as a distance) into the achievement field 1605, and some task or other action that will occur if the user does not meet the stated achievement in the consequence field 1607. Once the user has completed the information in the achievement field 1605 and the consequence field 1607, then the user actives the submission button 1609 to submit the resolution information to the athletic data display configuration module 605.

After receiving the resolution information, the athletic data display configuration module 605 will monitor the user's athletic activity to determine whether the user has complied with his or her resolution. If the athletic data display configuration module 605 determines that the user has met the stated resolution, then the athletic data display configuration module 605 may provide some type of positive feedback to the user. For example, the athletic data display configuration module 605 may send the user an electronic mail message congratulating the user on keeping his or her resolution. Alternately or additionally, the athletic data display configuration module 605 may memorialize the achievement as described above. If, however, the user does not meet the stated resolution, then the athletic data display configuration module 605 may encourage the user to perform the specified task or action. The athletic data display configuration module 605 may, for example, send an electronic mail message to the user to remind the user of his or her resolution. Of course, various implementations of the invention may perform alternate or additional actions to encourage the user to perform the specified task or action.

Athletic Equipment Interface

As users or athletes such as runners utilize the systems of embodiments of the present invention to collect information, a user interface of an embodiment may provide additional features and functionality for athletes to use and share information relating to their physical activity. In one exemplary form of the invention, athletic information is displayed on a user interface 1700 and/or user interface 2400 as described in greater detail below.

For example, a user or athlete may wish to perform their walking, jogging, running, or other athletic activity with the help of an athletic performance device or machine (i.e., athletic equipment). For example, the user or athlete may wish to use a stair stepping machine, elliptical machine, treadmill, resistance training (i.e., weight) machine, ergometer, stationary bicycle, climbing machine, or any other athletic performance device or machine. As described above with reference to FIGS. 1-16, the user or athlete may provide a digital music player 203 that may, among other features, monitor and store athletic performance data. In an alternate embodiment, the user or athlete may provide another storage device, such as flash drive or other similar Universal Serial Bus (USB) storage device, compact flash, memory stick, secure digital card, or any other portable storage device. As will be described in more detail below, the digital music player 203 or other storage device may couple to the athletic performance device or machine, for example via a wired or wireless connection, to interact with the athletic performance device or machine. Additionally, the digital music player 203 or other storage device may couple to the athletic performance device or machine via a combination of wired and wireless connections. For example, the digital music player 203 or other storage device may couple to the athletic performance device or machine via a wired connection while the user or athlete may interact with or control the digital music player 203 or other storage device with a wireless connection, for example with a remote control or other similar wireless device.

In an embodiment, the athletic performance data may be generated by one or more athletic performance sensors located on or adjacent to the user or athlete, for example on or in the user or athlete's shoe as illustrated by FIG. 4. In an alternate embodiment, athletic performance data may be generated by one or more athletic performance sensors coupled to the athletic performance device or machine. In yet another embodiment, athletic performance data may be generated by one or more athletic performance sensors located on or adjacent to the user or athlete and may be generated by one or more athletic performance sensors coupled to the athletic performance device or machine.

In an embodiment, and as described above with reference to FIGS. 1-16, the user or athlete may provide a digital music player 203 or other storage device that may, among other features, monitor and store current athletic performance data. The digital music player 203 or other storage device may further store and provide historical athletic performance data. The digital music player 203 or other storage device may communicate directly with the user interface 1700 via wired or wireless connection. For example, the athletic performance device or machine including user interface 1700 may further include an interface 1740 that may be a wireless transceiver or wired connector to bi-directionally interface with the digital music player 203 or other storage device.

More specifically, a particular athletic performance device or machine may measure or sense performance data for a user or athlete interacting with the athletic performance device. For example, a stair stepping machine may communicate weight, climbing rate (e.g., vertical feet per minute), calories burned, heart rate, and the like to the digital music player 203 or other storage device coupled thereto as described above. Further, the digital music player 203 or other storage device may communicate historical athletic performance data or other stored athletic performance data to the athletic performance device or machine. In an embodiment, the current athletic performance data, the historical or stored athletic performance data (e.g., as stored by digital music player 203 or other storage device), or a combination thereof may be displayed by user interface 1700. In an embodiment, the user interface 1700 may be a console or the like coupled to the athletic performance device or machine that is viewable by and accessible to the user or athlete interacting with the athletic performance device or machine. More specifically, the user interface 1700 may be a console that displays the user or athlete's athletic performance substantially in real-time. Further, the user interface 1700 console may display a comparison of substantially real-time athletic performance data to historical or otherwise stored athletic performance data.

In an embodiment, the user interface 1700 console may include one or more portions. For example, the user interface 1700 console may include a workout portion 1710, a history portion 1720, and a message portion 1730. Further, the user interface 1700 may include an interface 1740 to couple to the digital music player 203 or other storage device. In an embodiment, the interface 1740 may be a wired or wireless interface as introduced above. The workout portion 1710 may include, for example, an input device for the user or athlete to input a workout goal or other workout parameters. For example, the input device may be a numerical pad for the user or athlete to input a workout goal or other workout parameters. The user or athlete may utilize the input device to select a quick start (e.g., a predetermined time at a predetermined intensity), or to input workout time, distance, calorie burn, or any other workout program. Further, the workout portion 1710 may include a display so that the user or athlete has an indication of their progress in the quick start, time, distance, calorie burn, or any other workout program.

In one arrangement, data may be sent to and received from an athletic performance monitoring or tracking site. For example, a user may transfer data recorded in a digital music player 203, as discussed above, to the athletic performance tracking site for storage. The digital music player 203 may have a connection to a network hosting the athletic performance tracking site. Alternatively, access to the athletic performance tracking site may be facilitated by a piece of athletic equipment such as an elliptical device, treadmill and the like that is connected to a network. The athletic performance tracking site may be configured to track various types of athletic performance data such as best times, most recent workout information, goals, resolutions, challenges and/or combinations thereof. Data stored in the digital music player 203 may be used to update athletic performance tracking site and vice versa. In one or more arrangements, other devices may also be used to store athletic performance data and/or to communicate with athletic performance tracking site and a piece of athletic equipment. For example, such devices may include mobile phones, personal digital assistants (PDAs), watches, USB type devices having athletic functionality, activity monitoring devices as well as other athletic oriented devices.

The information stored on the digital music player 203 or other portable device may be displayed on interface 1700. For example, information corresponding to a most recent workout may be displayed on interface 1700 to provide a user with a basis of comparison with a current workout. In another example, a best workout time for a particular piece of athletic equipment may be displayed on the athletic equipment to challenge a user to beat that time. A piece of athletic equipment may be configured to automatically select or extract information relating to that type of athletic equipment while ignoring or discarding other information. Alternatively, the portable device might only transmit information relating to a type of athletic equipment the user is using. In one or more configurations, athletic equipment may query an athletic performance tracking site to obtain workout information. Once such information is obtained, the information can be displayed on the interface 1700 or on the portable device 203. Furthermore, the portable device 203 and/or athletic equipment can be configured to transmit information to the athletic performance tacking site. For example, workout data may be immediately transferred from the athletic equipment to the athletic performance tracking site upon completion of a workout. Thus, bi-directional communication is provided between the portable device 203/athletic equipment and the athletic performance tracking site. Constant updates can be provided from the athletic performance tracking site to the athletic equipment and portable device 203. Communication between the athletic equipment and athletic performance tracking site may be via wired or wireless connections.

The history portion 1720 may interact with the digital music player 203 or other storage device via interface 1740 to retrieve historical data related to the user or athlete's past performance. For example, the history portion 1720 may retrieve and display the user or athlete's last workout and best workout for a particular athletic performance device or machine. In particular, the history portion 1720 may retrieve and display the user or athlete's last and best workout time, distance, calorie burn, distance equivalent (e.g., "cardiovascular miles") and floors (e.g., if the history portion is coupled to a stair stepper athletic performance device or machine). Further, the history portion may display the user or athlete's current athletic performance compared to their last workout and historical best workout so that they have an indication of their current athletic performance. In an alternate embodiment, the user interface 1700 may receive at least part of the historical or otherwise stored athletic performance data associated with a user or athlete via a wired and/or wireless connection to an additional athletic performance database such as the athletic performance tracking site. For example the user interface 1700 may include Internet or other web-based connectivity to bi-directionally communicate current and/or historical athletic performance data.

The distance equivalent, for example cardiovascular miles, may represent athletic performance data of differing types converted to a common unit. For example, a runner may wear a shoe that includes a pedometer or accelerometer to track distance run, pace, average speed, and the like. The pedometer may further communicate the athletic performance data to the digital musical player 203 or other storage device for storage and transmission/relay to the user interface 1700. Alternatively, the user or athlete may be resistance training (i.e., lifting weights) on any number of resistance training machines including one or more athletic performance sensors coupled thereto. The athletic performance sensor(s) may detect total weight lifted (i.e., weight lifted multiplied by the number of repetitions), maximum weight lifted, lifting rate/pace, delay between sets, and the like. Similarly, the resistance training machines may further communicate the athletic performance data to the digital musical player 203 or other storage device for storage and transmission/relay to the user interface 1700.

In an embodiment, the user interface 1700 may thereafter convert the received athletic performance data to a common unit. In an embodiment, an athletic performance module may convert the received athletic performance data to distance (in an embodiment, miles) run. In the above example, the runner's data already represents miles run. However, the resistance trainer's data represents total weight lifted, maximum weight lifted, lifting rate/pace, delay between sets, and the like. The user interface 1700 may convert the resistance trainer's data to distance run in a variety of manners. For example, the user interface 1700 may include a database, look-up table, or the like that stores predetermined conversion factors between, for example, total weight lifted and miles run. The database or look-up table may further contemplate additional metrics such as maximum weight lifted, etc., as introduced above. Alternatively, the athletic performance module may apply the data to one or more algorithms to calculate the distance run equivalent. Accordingly, a goal or challenge may be set in terms of a common unit so that a user may perform a variety of activities to meet the goal or challenge.

The user interface 1700 may further determine the calorie usage or burn for each athletic performance. Once the calorie usage or burn has been determined, a database, look-up table, or algorithm may convert calorie usage or burn to miles run based on one or more physical characteristics (e.g., age, weight, gender, heart rate, and the like) of the user or athlete. In one example, 100 calories may equal 1 common unit (e.g., a cardiovascular mile). A conversion unit may depend on one or more characteristics including weight, height, age, type of athletic activity and the like. Additional comparisons may then be based on the cardiovascular miles or actual miles run or a combination thereof. The one or more physical characteristics may be provided, for example, by the digital music player 203, other storage device, or the user interface 1700 Internet or web connectivity. Alternatively, instead of determining the calorie usage or burn for an athletic performance, the user interface (in an embodiment via transmission or relay from a digital music player 203, other storage device, or the user interface 1700 Internet or web connectivity) may receive the calorie usage or burn from the athletic performance device or machine for subsequent conversion to distance run. For example, an ergometer may track the number of miles rowed by a user athlete. However, it may also track the calorie usage or burn corresponding to the miles rowed. Instead of converting the miles rowed to miles run, the user interface 1700 may convert calorie usage or burn to miles run. Accordingly, the operation of user interface 1700 may be simplified for those athletic performance devices or machines that already calculate calorie usage or burn. Though described with reference to one or few athletic performance metrics, it is to be understood that the user interface 1700 may calculate, determine, or otherwise generate the equivalent distance run based on any number of athletic performance metrics.

Once the athletic performance of the user or athlete has been converted to a common unit, for example miles run, they may compare their athletic performance with personal goals, against athletic performance benchmarks, and/or against historical athletic performance. For example, a user or athlete may establish a personal goal of running 100 miles, but may wish to achieve the equivalent of running 100 miles by performing a variety of athletic activities including activities involving one or more athletic performance devices or machines. Similarly, an athletic benchmark or milestone may suggest running 25 miles per week. A user or athlete may reach the benchmark or milestone by any form of athletic activity. Finally, once their athletic performance or activities have been converted to a common unit, in an embodiment miles run, multiple active people and athletes may participate in competitions, races, or other events. Such competitions, races, or other events are described herein and generally by U.S. patent application Ser. No. 12/031,380 filed Feb. 14, 2008, and incorporated herein in its entirety.

A message portion 1730 may display messages for the user or athlete. For example, the message portion 1730 may remind the user or athlete to synchronize their digital music player 203 or other storage device with the user interface 1700 or 2300 to transfer athletic performance data. Further, the message portion may provide an indication as to how a current workout or athletic performance data compares to the best workout or athletic performance data for the user or athlete. If the user or athlete is participating in a challenge, competition, or the like, the message portion 1730 may provide an indication as to the user or athlete's progress or comparison to the challenge or competition leader. Additionally, the message portion 1730 may provide congratulatory remarks or other feedback should the user or athlete achieve a personal goal, benchmark, or milestone.

FIGS. 18-22 disclose another exemplary embodiment of the present invention. This embodiment utilizes a portable device in the form of a wearable device assembly 1800 that communicates with the athletic performance device or machine similar to the communication between the athletic performance device or machine and digital music player 203 or other storage device as described above. The wearable device assembly 1800 generally includes a wearable device 1802 that in one exemplary embodiment is a USB (Universal Serial Bus) type device 1802, and a carrier 1804 that in one exemplary embodiment takes the form of a wristband 1804. The device 1802 has many features similar to a USB flash drive, but has additional athletic functionality like that described above with respect to the digital music player 203 or other storage device. In addition, the device 1802 is removably connected to the wristband 1804.

Figure 17:
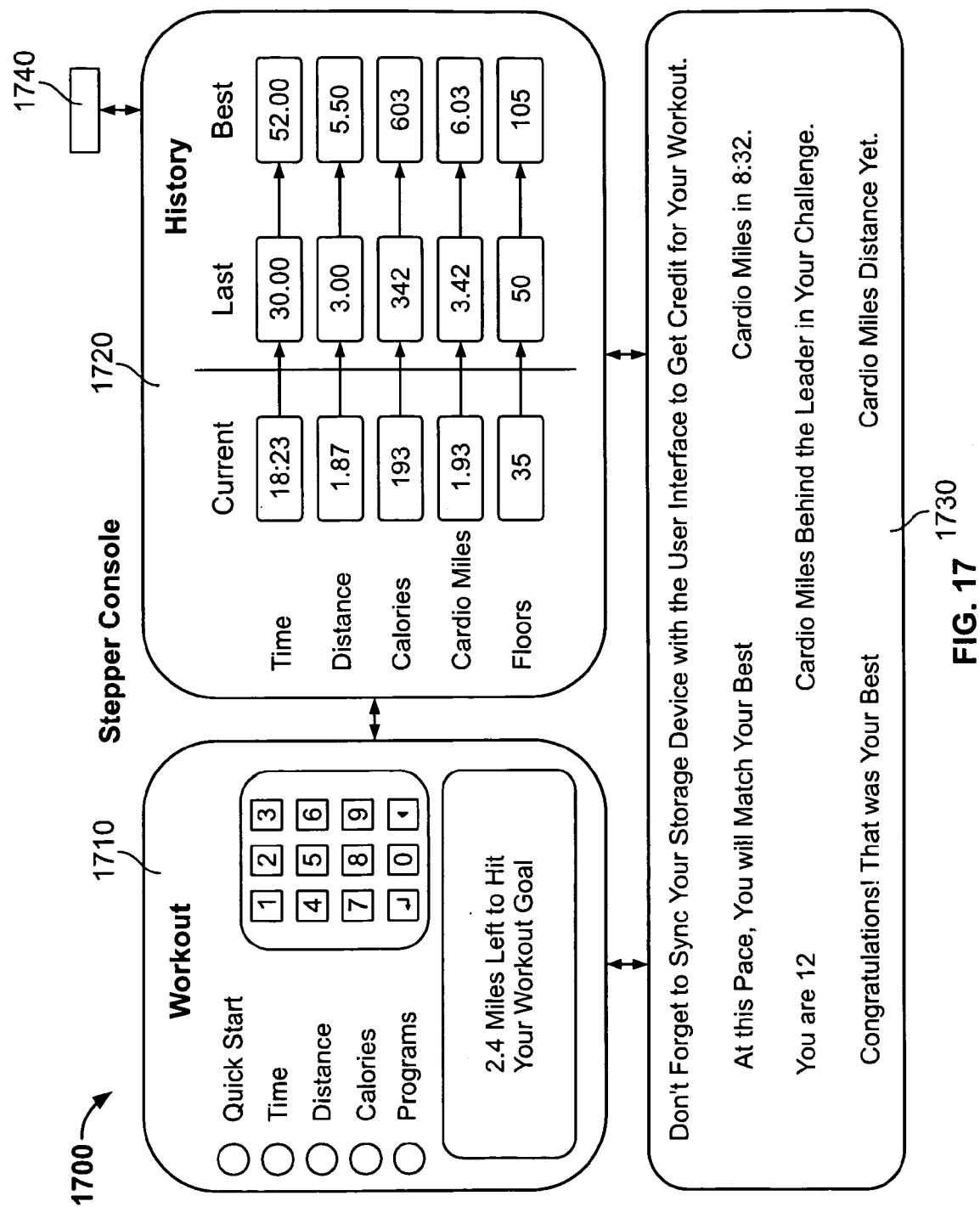
FIG. 17 illustrates an example of a user interface that may be provided as part of athletic equipment according to various implementations of the invention
Figure 42:
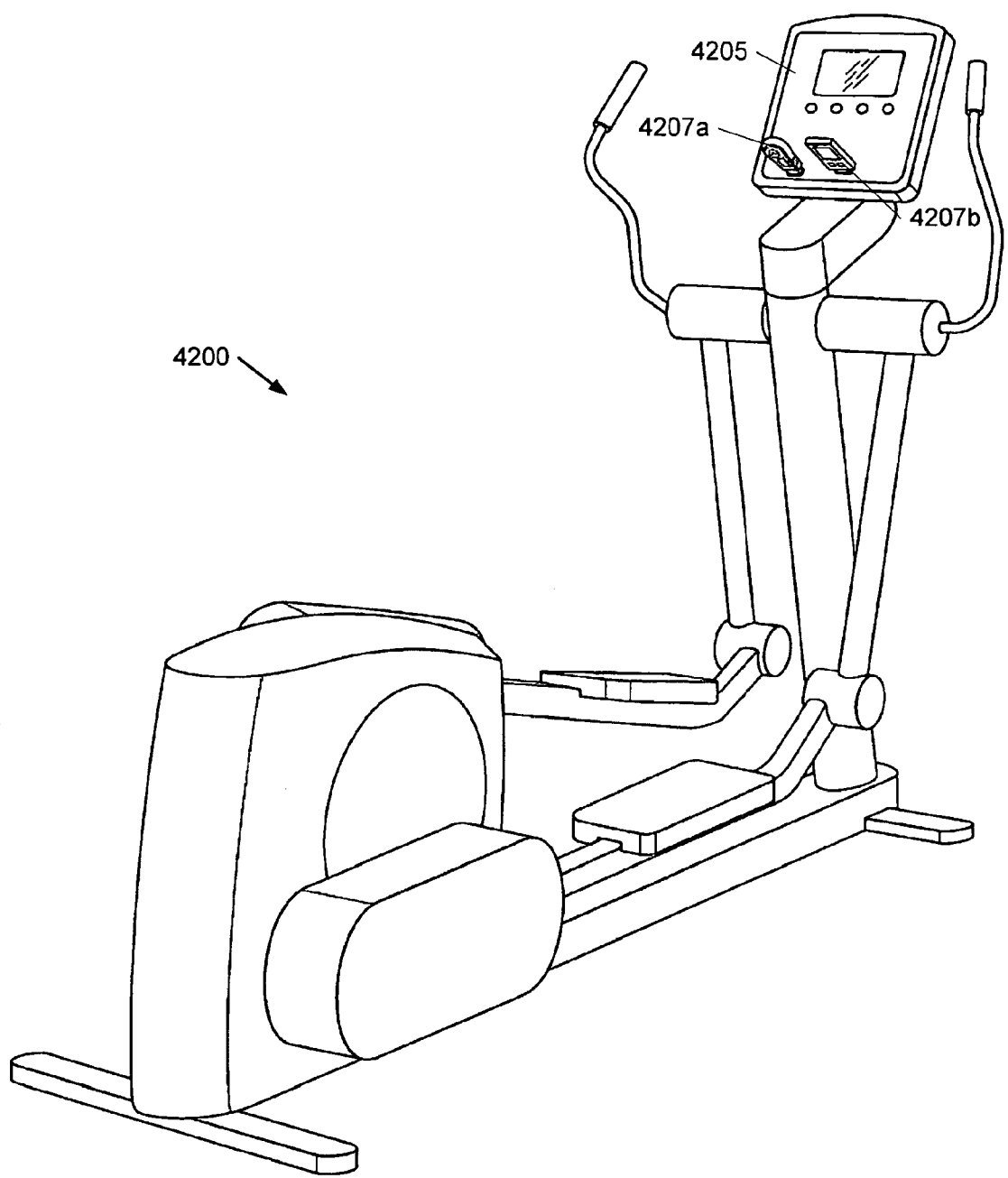
FIG. 42 illustrates gym equipment in the exemplary form of an elliptical machine having a user interface according to an embodiment of the invention.

As further shown in FIGS. 18-21, the USB type device 1802 generally includes a housing 1806 and a controller 1808 that is contained by the housing 1806. General components and functional capabilities of the controller 1808 regarding athletic functionality are similar to the digital music player 203 or other storage device described above. The housing 1806 includes a connector 1810 that is generally a standard USB connector having leads 1812 or contacts embedded therein. As explained in greater detail below, the connector 1810 is adapted to connect to a USB hub of a computer (FIG. 22) or a USB hub or other interface located on the athletic performance device or machine (shown schematically on the console shown in FIG. 17). Such a connection is also shown schematically on the fitness equipment 4200 shown in FIG. 42. In FIG. 42, fitness equipment 4200 includes a console 4205 to which a sportband such as sportband 4207*a* and a digital music player such as digital music player 4207*b* may be connected. In some arrangements, sportband 4207*a* and digital music player 4207 may plug directly into console 4205. In other arrangements, sportband 4207*a* and digital music player 4207 may be connected through a cable (not shown). The illustrated connection between each of sportband 4207*a* and digital music player 4207*b* with console 4205 is illustrated as a physical connection. However, various other connection types may be used including wireless connections (e.g., infrared connections, wireless local area network connections, BLUETOOTH connections and the like).

Referring again to FIGS. 18-21, the housing 1806 has a first pushbutton 1814 that will cooperate with a first input of the controller 1808 for controlling the wearable device 1802 as needed. The housing 1806 also has a second pushbutton 1816 that cooperates with a second input of the controller 1808 for controlling the wearable device 1802 as needed. The front side of the housing 1806 accommodates a display 1818 of the controller 1808. As further shown in FIGS. 19 and 21, the back side of the housing 1806 has a protrusion 1820. The protrusion 1820 has a generally circular cross-section and an enlarged rounded head. The protrusion 1820 is adapted to be inserted into a receiver or aperture in the carrier 1804.

Figure 21:
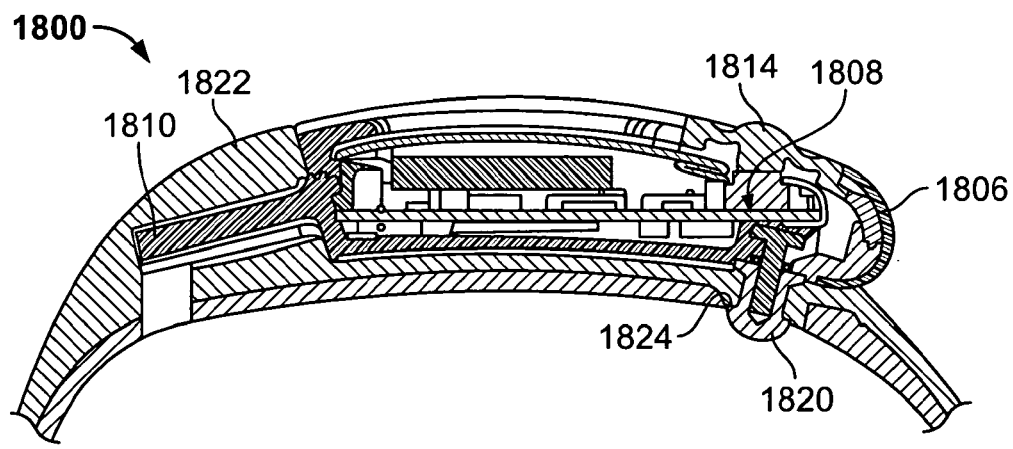

As further shown in FIG. 21, the components of the controller 1808 are contained within and supported by the housing 1806. The controller 1808 includes various electrical components allowing the controller 1808 and device 1802 to act as an interface device wherein the device 1802 can communicate with, for example, a shoe-based sensor, record and store data relating to athletic performance, other time information, as well as upload performance data to a remote location or website as described in greater detail below. The controller 1808 can also interact with an athletic performance device or machine for data recording as described above. Thus, athletic performance data can be transferred from the athletic equipment during a workout and stored on the device 1802.

Figure 18:
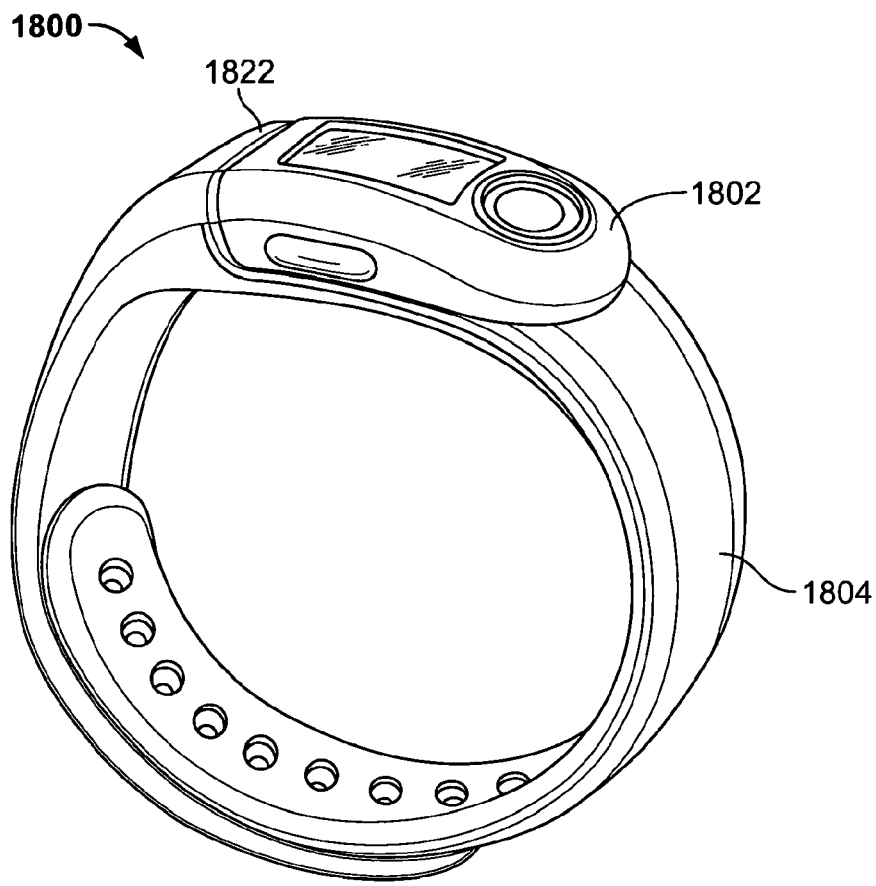
FIGS. 18, 19, 20, 21 and 22 illustrate an example of an athletic performance data storage device.
Figure 19:
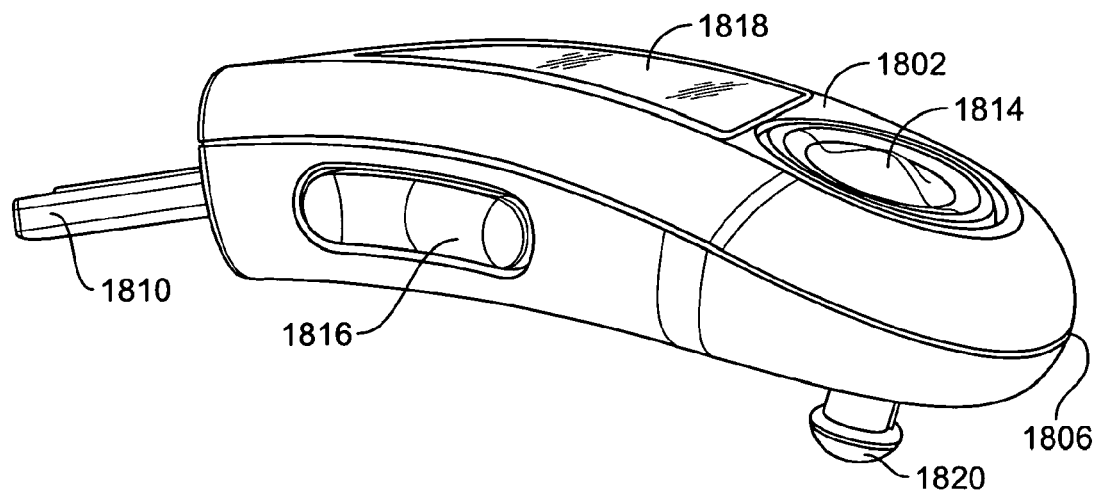
Figure 20:
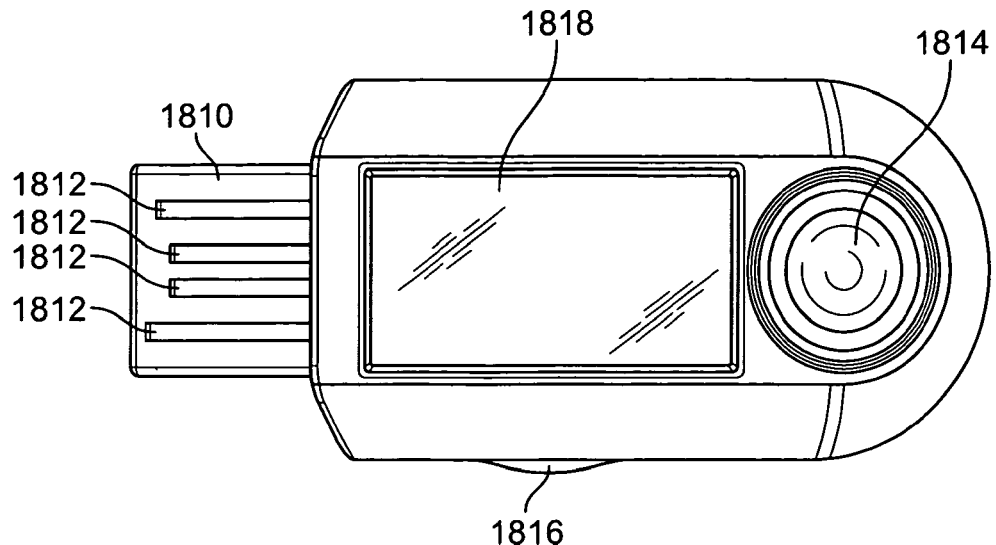

As shown in FIG. 18, the carrier 1804 is generally in the form of a wristband having a central portion between a first end and a second end. The wristband 1804 may include a first member and second member generally molded or connected together. The wristband is flexible to fit around a user's wrist. The wristband 1804 has receiving structures for connection to the device 1802. The carrier 1804 includes a protective sleeve 1822 proximate the central portion for receiving the connector 1810. The protective sleeve 1822 has a generally contoured surface. The sleeve 1822 may have internal structure for assisting in securing the connector 1810. Also at the central portion, the carrier 1804 has an aperture 1824 (FIG. 21) dimensioned to receive the protrusion 1820 of the wearable device 1802. Thus, when the wearable device 1802 is connected to the wristband 1804, the connector 1810 is secured within the protective sleeve 1822 and the protrusion 1820 is received by the aperture 1824.

Figure 22:
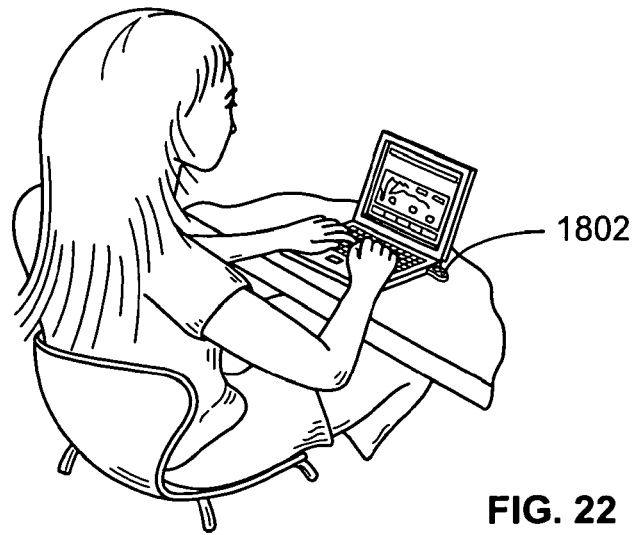

As discussed, in one configuration, the wearable device assembly 1800 is operably connected to a sensor such as mounted in a shoe. Similar to the digital music player 203 or other storage device, the wearable device 1802 receives data from the sensor associated with the athletic performance of a user. It is understood that the user may wear the device on the wrist while performing an athletic activity. The user may then remove the wearable device 1802 from the wristband 1804 and plug the device 1802 into a personal computer such as shown in FIG. 22, wherein collected data can be uploaded to a remote location such as a website dedicated to displaying the athletic performance of users, such as the athletic performance tracking site described above.

In another configuration, the wearable device 1802 can be used in conjunction with athletic performance devices or machines, for example gym equipment. For example, gym equipment such as treadmills, elliptical machines, stair machines, bicycles, other weight equipment and the like may have USB ports for added functionality. A user may remove the wearable device 1802 from the wristband 1804 and insert the device 1802 into the gym equipment, such as in a USB port or other interface located on the stepper console shown in FIG. 17. Such configuration is also shown in FIG. 42. The user performs athletic activity wherein data associated with the activity is received by the USB device 1802. The type of data capable of being received by the USB device is generally similar to the data reception described above with the operable connection between the digital music player 203 or other storage device and the gym equipment. Once the athletic activity is complete, the user removes the USB device 1802 from the gym equipment and again mounts the device on the wristband 1804 or some other carrier as desired. The user can then insert the USB device 1802 into a personal computer wherein the data from the athletic activity associated with the gym equipment can be uploaded to a remote location such as the above described website. Additional wired or wireless communication capabilities could also be incorporated into the device 1802.

Though described with reference to bi-directionally communicating athletic performance data, in an additional embodiment, the digital music player 203, other storage device, and/or user interface 1700 Internet or web-based connectivity may control one or more parameters of the athletic performance device or machine. For example, the digital music player 203, other storage device, and/or user interface 1700 Internet or web-based connectivity may provide a workout level, duration, intensity, pace, incline, target heart rate, resistance, or any other parameter associated with an athletic performance device or machine. In an embodiment, the one or more parameters may reflect current and/or historical athletic performance data. Alternately or additionally, the one or more parameters may reflect an athletic performance training program or plan.

FIGS. 23-39 illustrate the collection and display of a user or athlete's performance data by user interface 2400 as collected from the digital music player 203 or other storage device. In an embodiment, athletic performance data is collected, for example and as illustrated by FIG. 23, when the digital music player 203 is synchronized. In an alternate embodiment, at least the performance data associated with the athletic performance device or machine (i.e., gym equipment) may be communicated and collected via a network, Internet, or other wired or wireless connection. For example, the athletic performance device or machine may couple to a network and or the Internet via a wired or wireless connection to transmit and receive athletic performance data associated with the user or athlete. Once the user or athlete's data has been collected, the user or athlete may view and interact with the athletic performance data as illustrated by user interface 2400 of FIG. 24.

Figure 24:
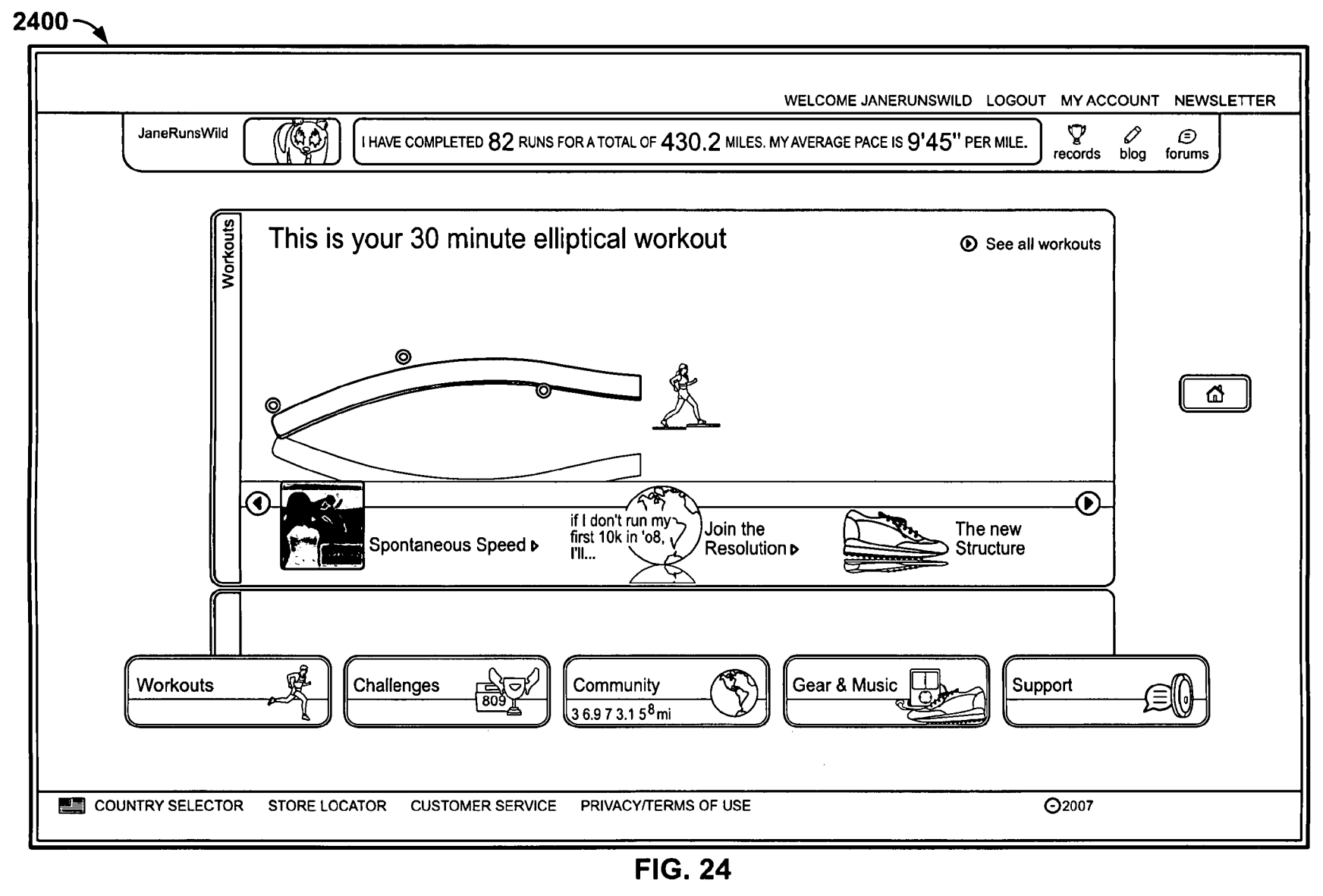
Figure 25:
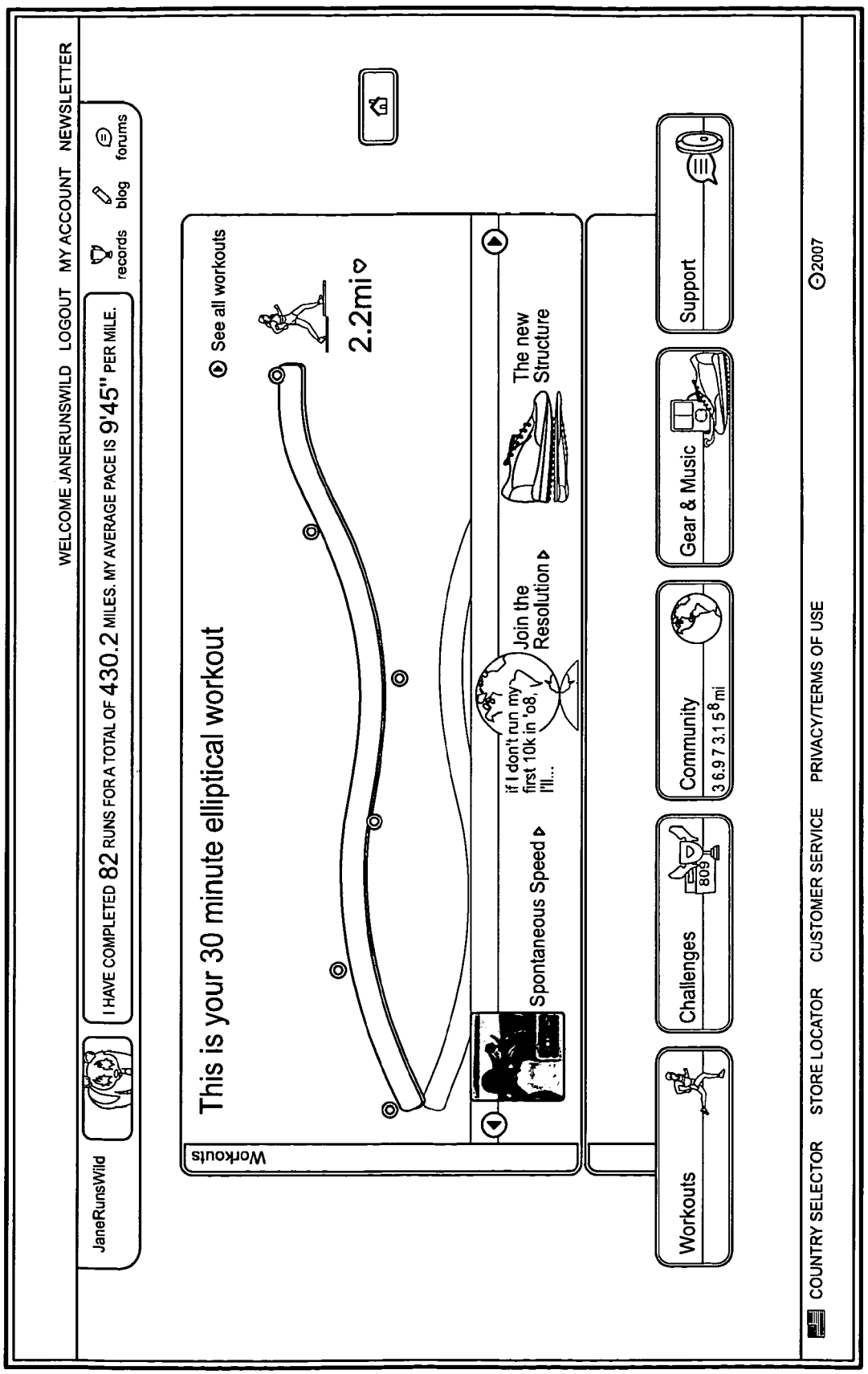

For example, FIGS. 24 and 25 illustrate that user interface 2400 may display details associated with a workout or other athletic performance. As illustrated, the details correspond to a workout on an elliptical machine. FIG. 25 in particular illustrates that the thirty minute elliptical workout has been converted to an equivalent miles run. Once a workout has been converted to its equivalent in miles run, it may be displayed alongside actual miles run as part of, for example, an interactive athletic training tool and/or interactive athletic training log. Such an interactive athletic training tool and/or interactive athletic training log is described by U.S. Provisional Patent Application No. 61/032,018, filed Feb. 27, 2008, and incorporated herein in its entirety.

Figure 26:
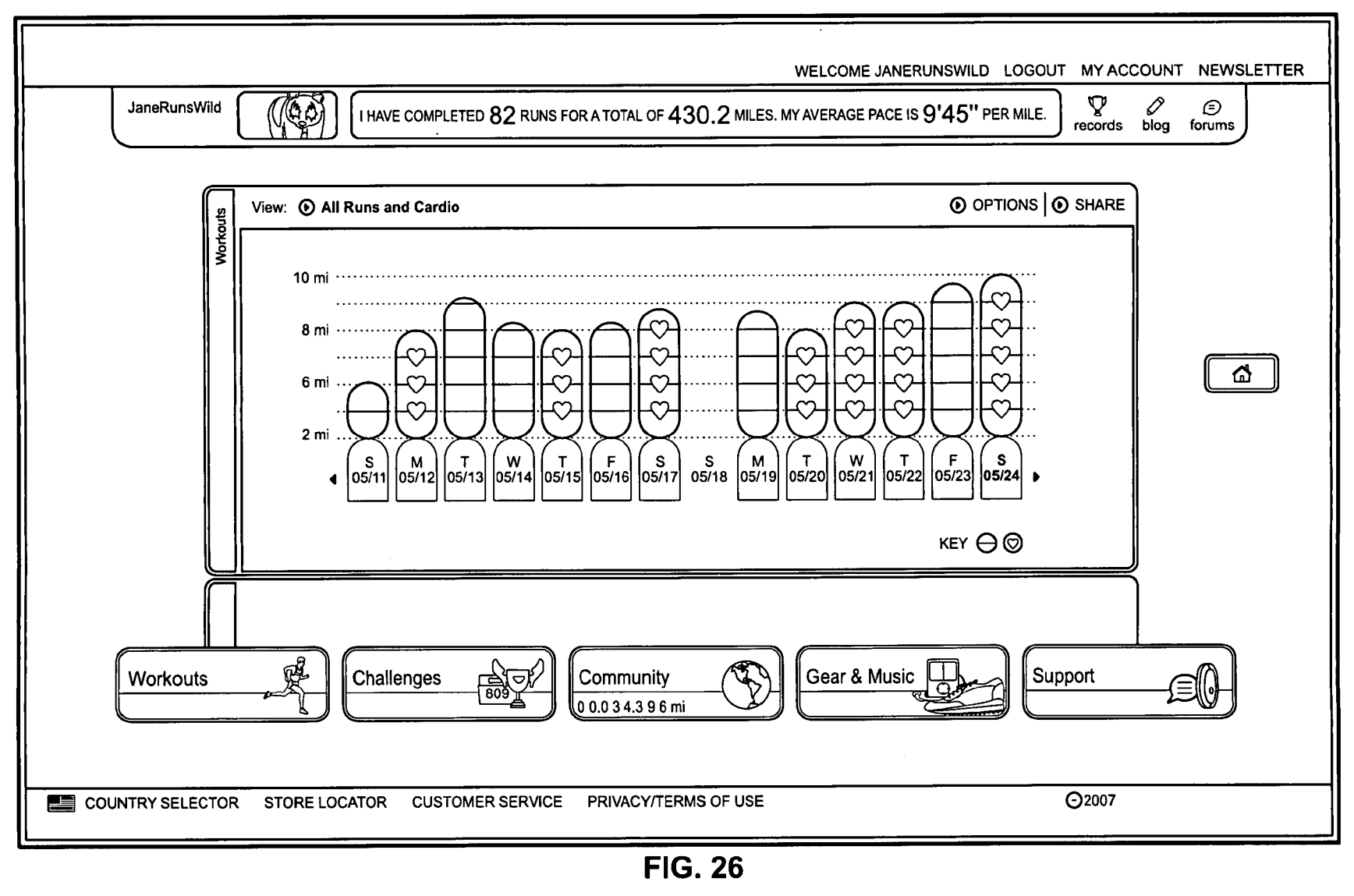
Figure 27:
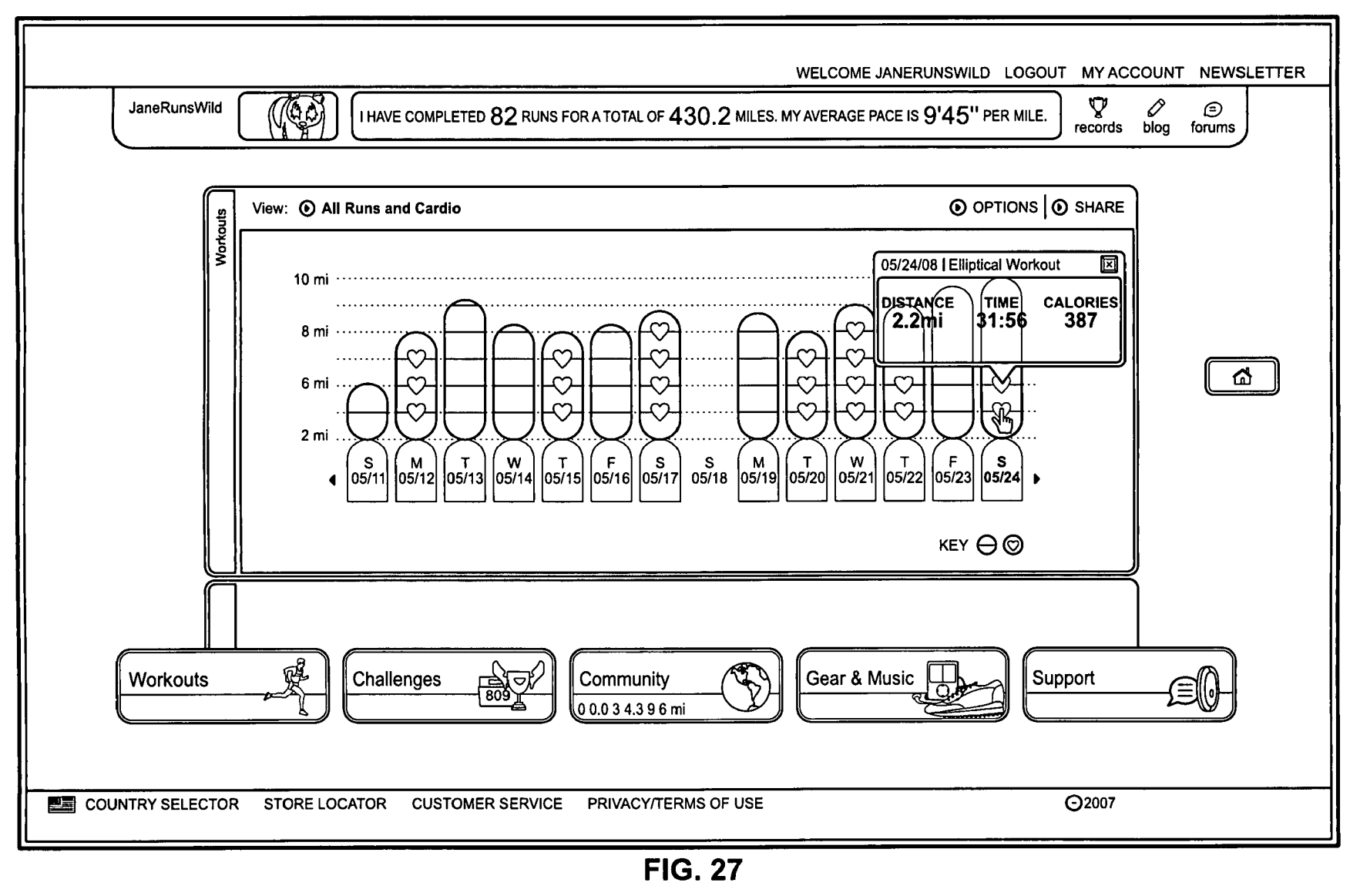

More specifically, FIG. 26 illustrates a range of dates for which the user or athlete has completed a run or other athletic performance. For dates on which the user or athlete completed their workout at least in part on one or more athletic performance devices or machines, the athletic performance data is illustrated with, for example, a different legend than actual running athletic performance data. For example, dates such as May 15 are displayed with a heart icon or other similar identification to illustrate that the user interface 2400 is displaying an equivalent distance (i.e., "cardiovascular miles") for a particular workout or athletic performance. FIG. 27 illustrates that the user interface 2400 may display details of a workout, for example type of athletic performance device or machine, equivalent distance, duration, and calorie usage or burn.

Figure 28:
FIG. 28 illustrates an example user interface that allows a user to choose whether to show all workouts, only workouts expressed in a common unit or only workouts expressed in an athletic activity specific unit according to one or more aspects described herein.
Figure 29:
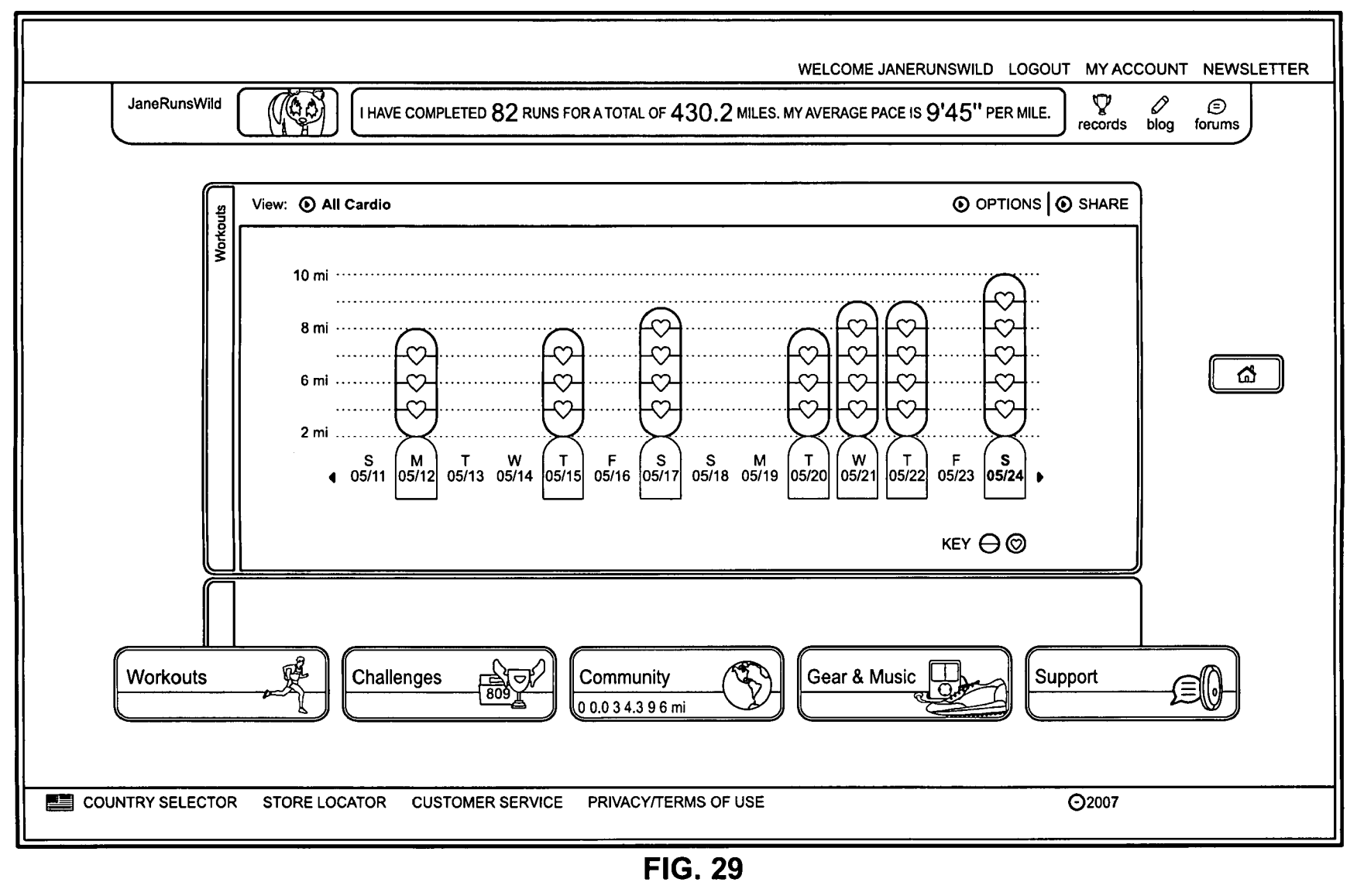
Figure 30:
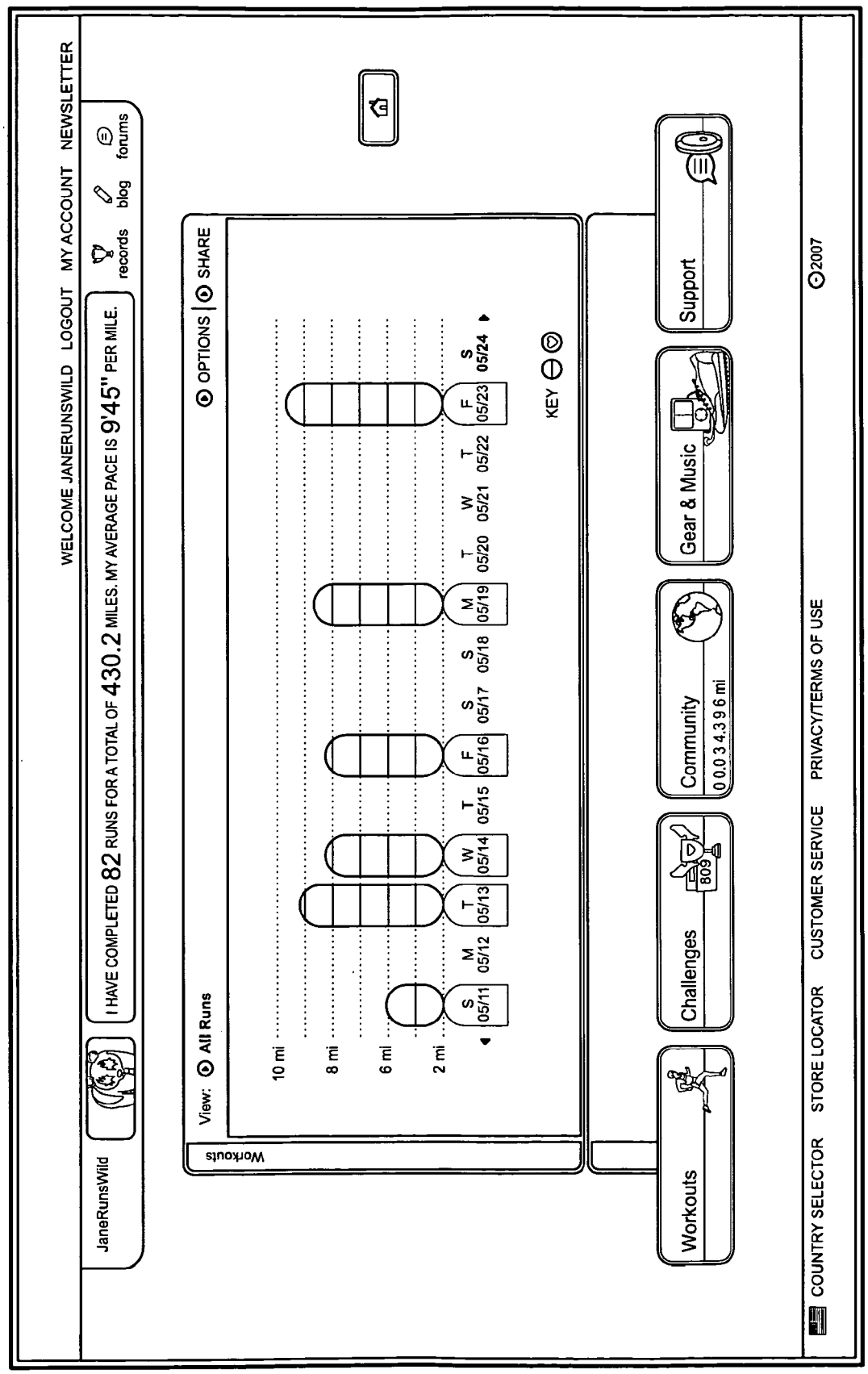
FIG. 30 illustrates an example user interface showing only workouts recorded or stored in an athletic activity specific unit according to one or more aspects described herein.

FIG. 28 illustrates that the user or athlete may sort their workouts or athletic performance based on whether the workouts or athletic performance represent actual distance run or equivalent cardiovascular distance. For example, the user or athlete may select that user interface 2400 display all runs and cardiovascular distance, all runs only, or all cardiovascular distance only. FIG. 29 illustrates user interface 2400 displaying only equivalent cardiovascular distance or athletic performance. FIG. 30 illustrates user interface 2400 displaying only actual distance run.

Figure 31:
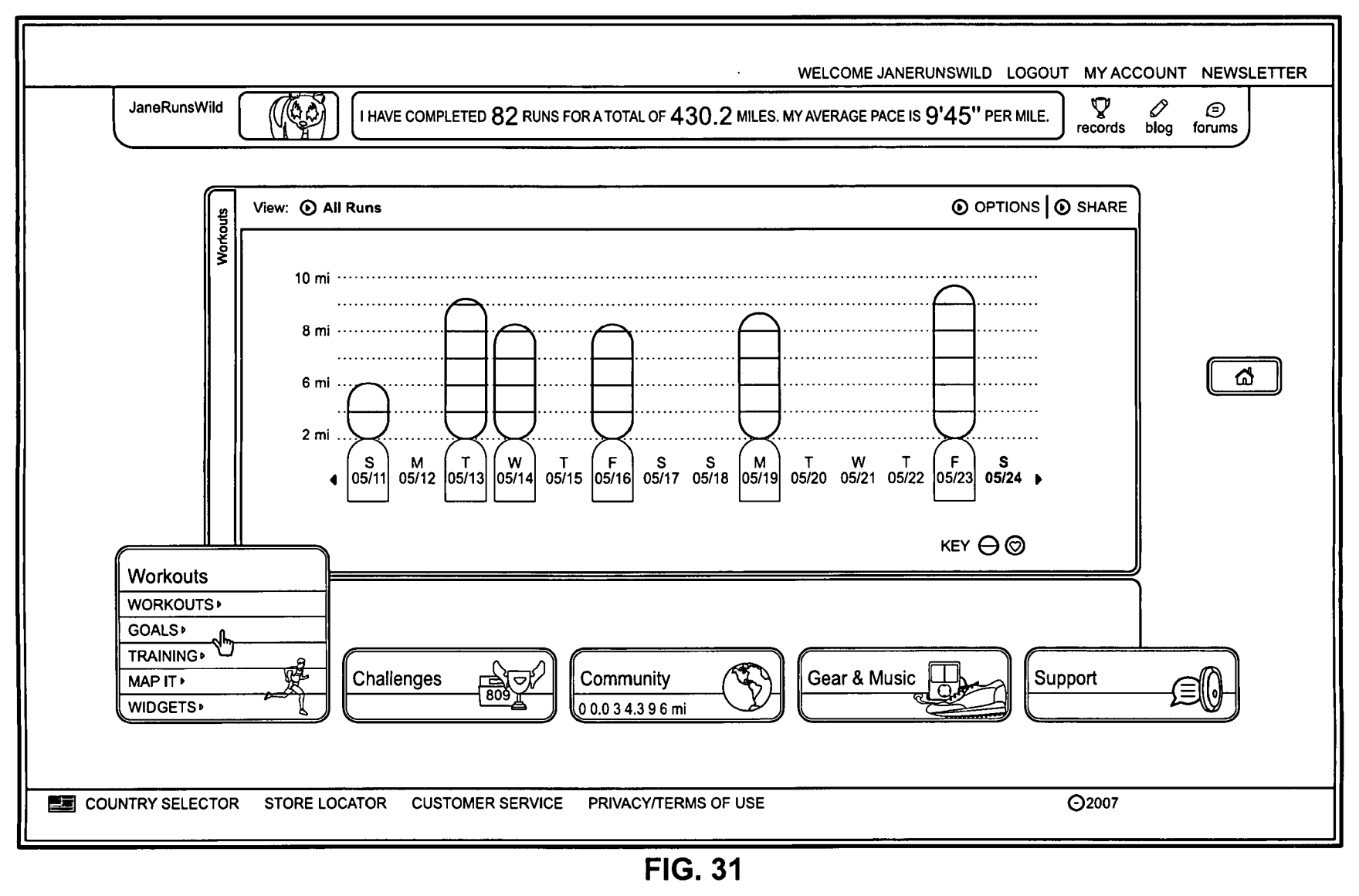
Figure 32:
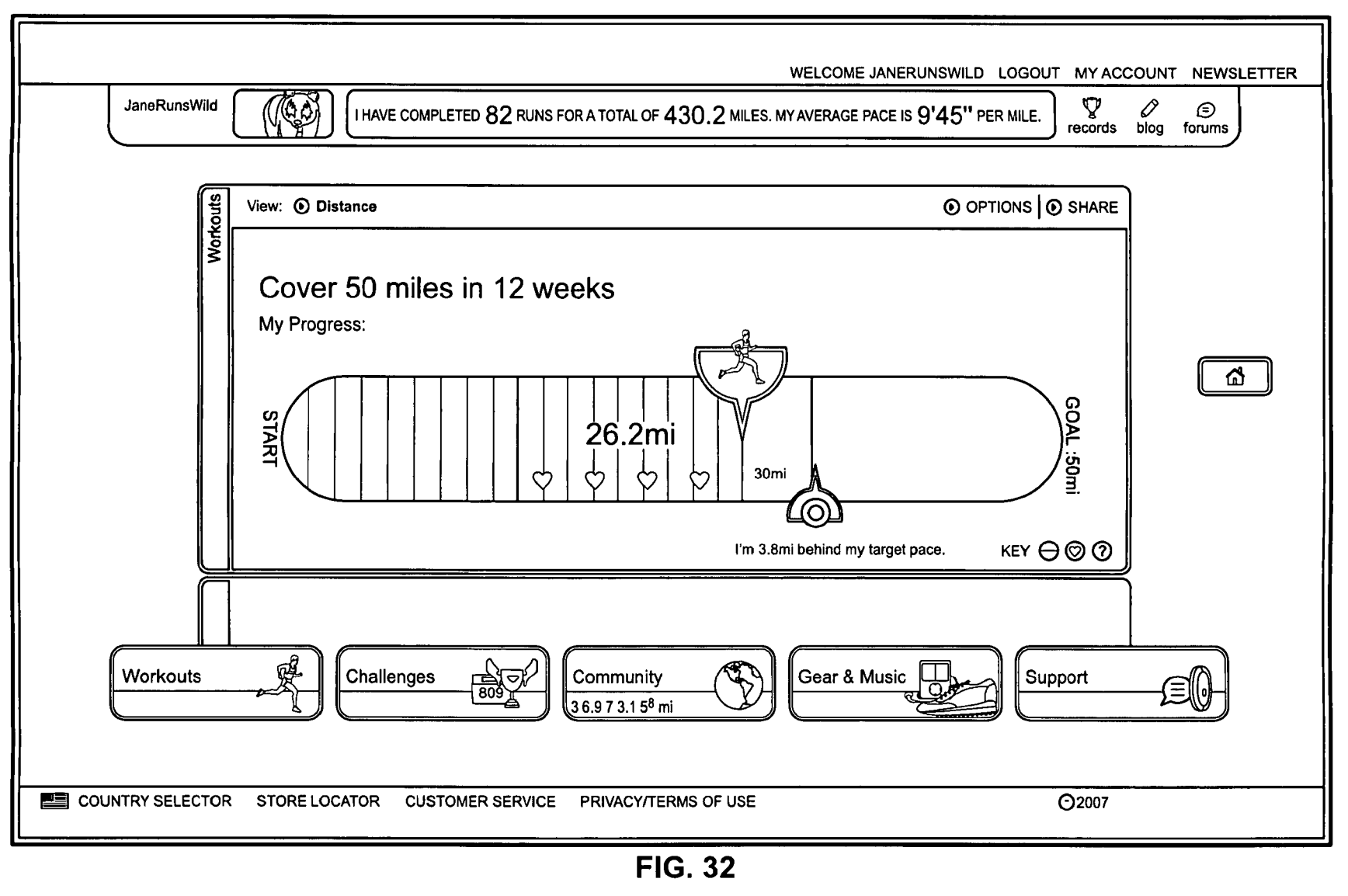

FIG. 31 illustrates that the user or athlete may utilize user interface 2400 to establish goals, benchmarks, milestones, and/or athletic training programs. For example, FIG. 32 illustrates that the user or athlete has established a goal of covering fifty miles in twelve weeks. Further, FIG. 32 illustrates the user or athlete's progress. In an embodiment, the user or athlete may achieve their goal by running, performing other athletic activities, or a combination thereof. Accordingly, the user or athlete's progress is displayed as a sum of any actual run distance and any equivalent cardiovascular distance. The user or athlete may therefore utilize various athletic performance activities to achieve their goal. If a user chooses to use a variety of athletic activities, interface 2400 or a goal tracking system may record the type of machine used to achieve various portions of the goal. Additionally or alternatively, users or athletes may publish their goals and their progress to others individuals such as other users, friends, trainers, teammates and family members. In one example, a trainer may track the progress of multiple trainees in reaching a specified goal and offer suggestions for improvement, encouraging comments and the like.

Figure 33:
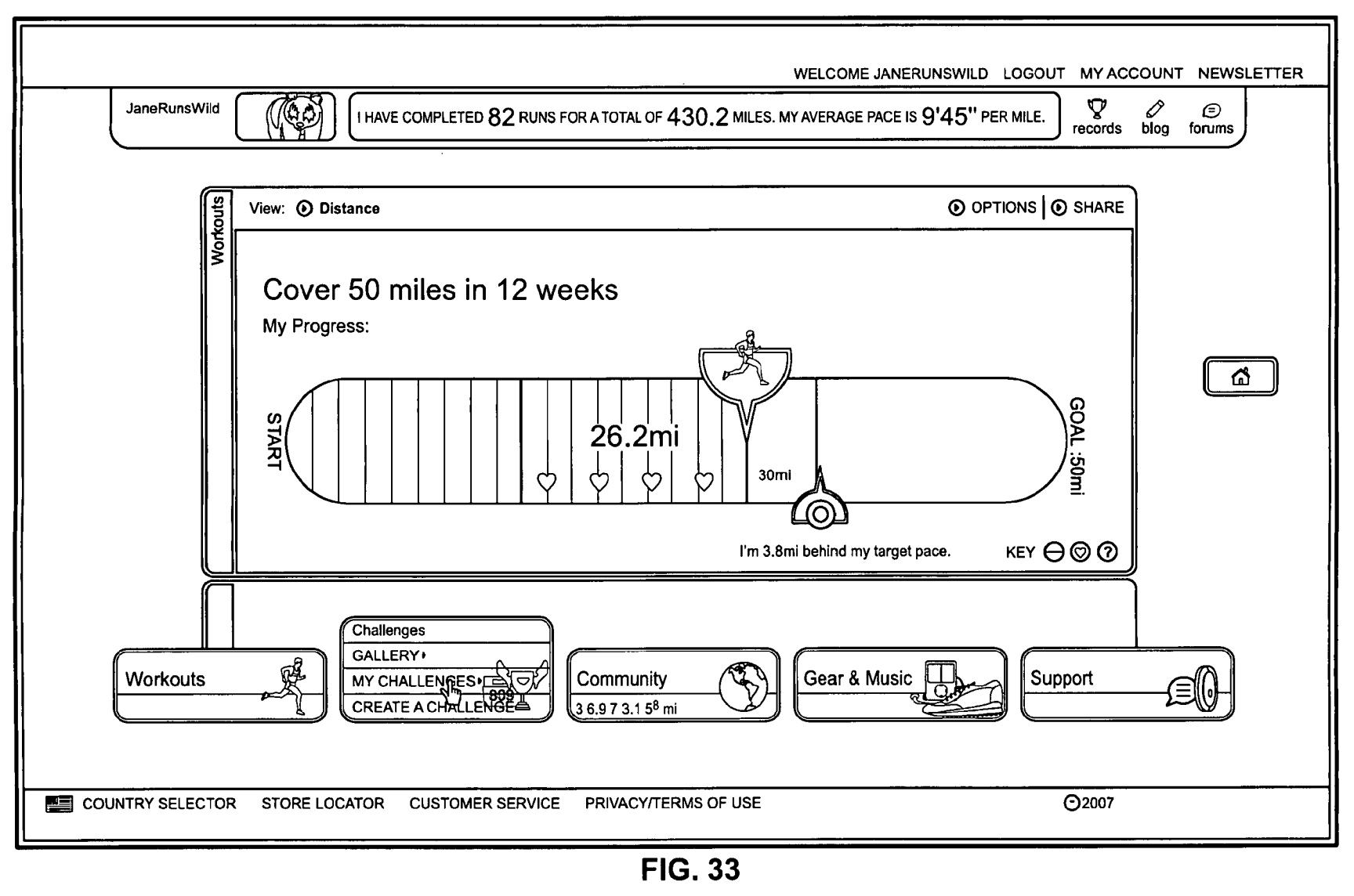

FIG. 33 illustrates that the user or athlete may utilize user interface 2400 to participate in competitions, challenges, races, or other events as described herein and generally by U.S. patent application Ser. No. 12/031,380 filed Feb. 14, 2008. In particular, the user or athlete may participate in the competition, challenge, race, or other event by completing runs, other athletic performance activities, or a combination thereof. Accordingly, their progress within the competition, challenge, race, or other event is determined by a sum of any actual runs and any other athletic performance as measured by equivalent cardiovascular distance. Further, the competition, challenge, race, or other event may specify a run portion and an athletic performance activity portion. For example, a fifty mile challenge may include twenty-five miles of actual running distance and twenty-five miles of equivalent cardiovascular distance.

Figure 35:
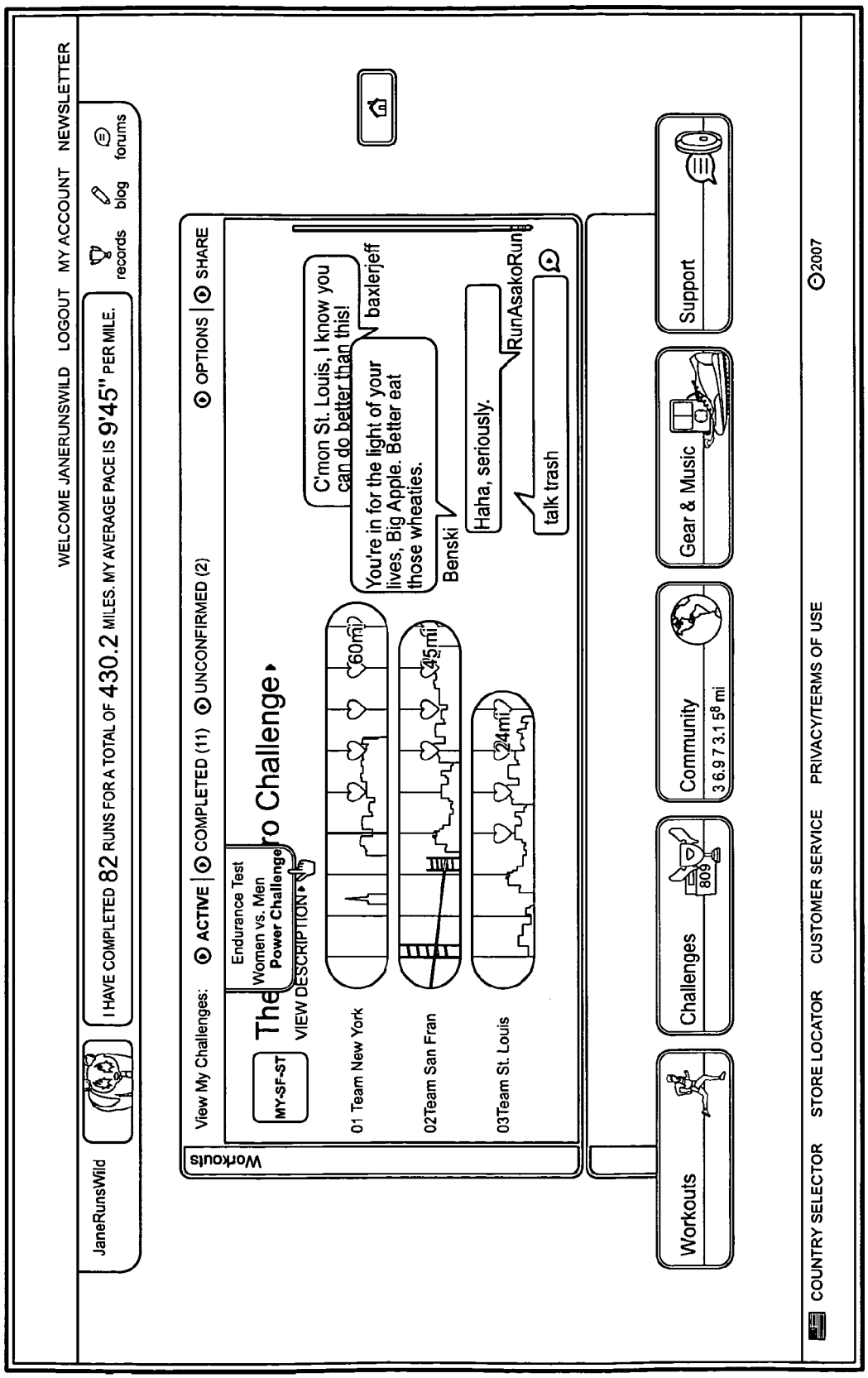
Figure 36:
Figure 37:
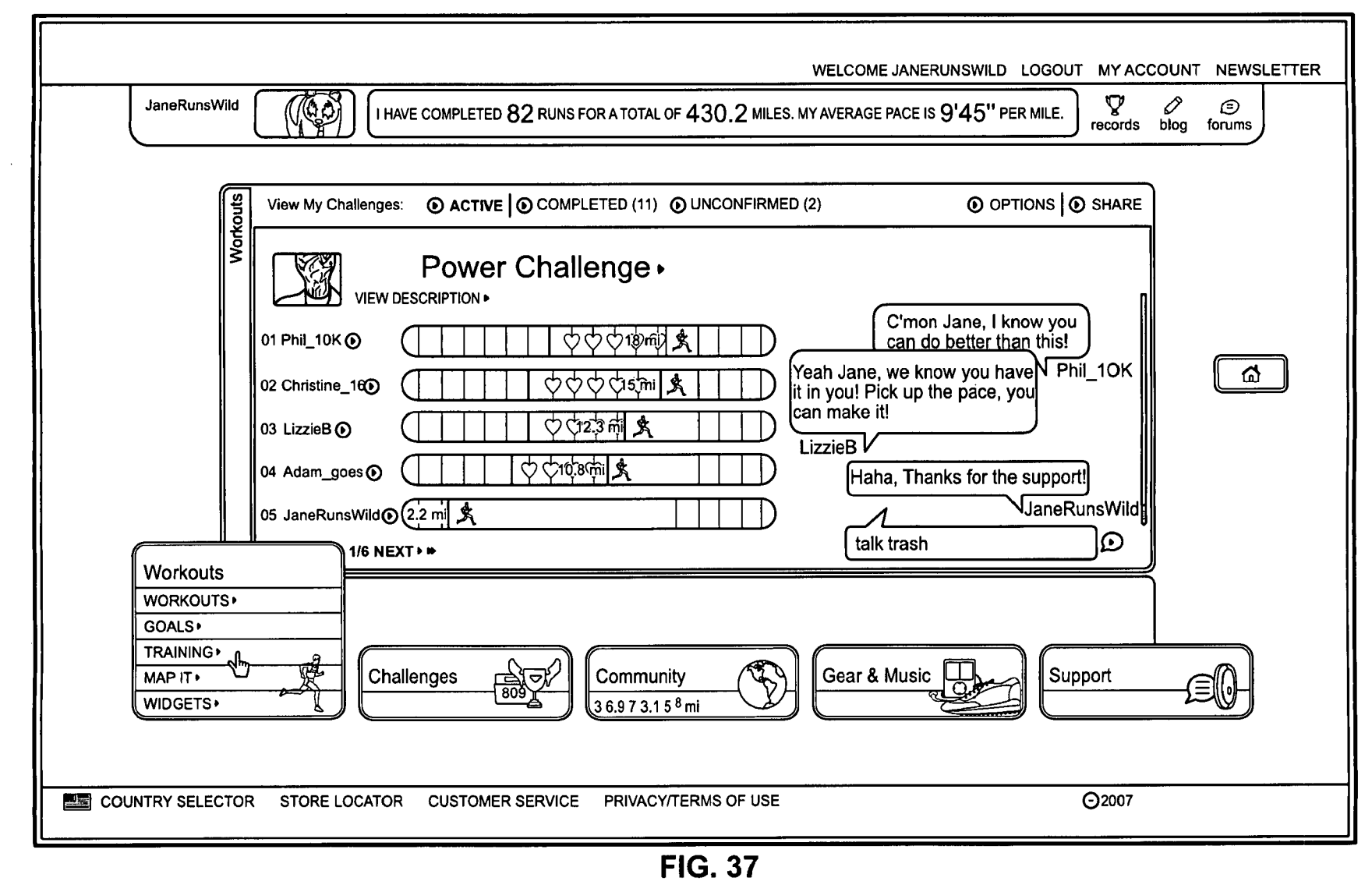

FIG. 35 illustrates that a user or athlete may select one or more challenges in which to participate. In an embodiment, the challenges are sorted by total distance (i.e., including actual run distance and equivalent cardiovascular distance). FIGS. 36 and 37 illustrate that the user interface 2400 may display the progress of one or more users or athletes participating in the competition, challenge, race, or other event. The progress of each user or athlete may be illustrated as a combination of actual run distance and equivalent cardio miles. For example, the progress of each user or athlete may be illustrated by a bar chart for which the actual run distance and equivalent cardiovascular distance have different colors, color schemes, patterns, or the like to distinguish which portion of the total distance covered represents each. Alternatively, the competition, challenge, race, or other event may include individual requirements for actual run distance and equivalent cardiovascular distance for which a user or athlete's progress in each may be displayed separately. Further, the user or athlete's run performance may be compared to their other athletic performance, for example as measured by equivalent cardiovascular distance.

Challenges may further specify specific types of athletic activity that are required to reach the challenge goal. For example, a challenge may indicate that 25 cardio miles must be performed on an elliptical, 50 cardio miles in weightlifting and 30 cardio miles in rowing. Alternatively, a challenge might only specify a total amount of cardio miles (or other common unit) regardless of the machine or activity performed. Challenges may also include a certain distance run as well as certain activity on a machine such as an elliptical machine and specifying a certain number of cardio miles. Thus, the challenges can include a variety of different activities. According to another aspect, challenges may take into account locations where athletic activity is performed. For example, a challenge may be issued for members of a particular gym or gym location. In another example, a challenge may be specific to all locations of a particular gym chain/provider. In yet another example, a challenge may be offered to a specific gym location or branch. Accordingly, gyms may compete against other gyms in a challenge. Similarly, challenges may be issued to have classes or groups within a gym compete with other classes or groups within the same gym or another gym.

Figure 38:
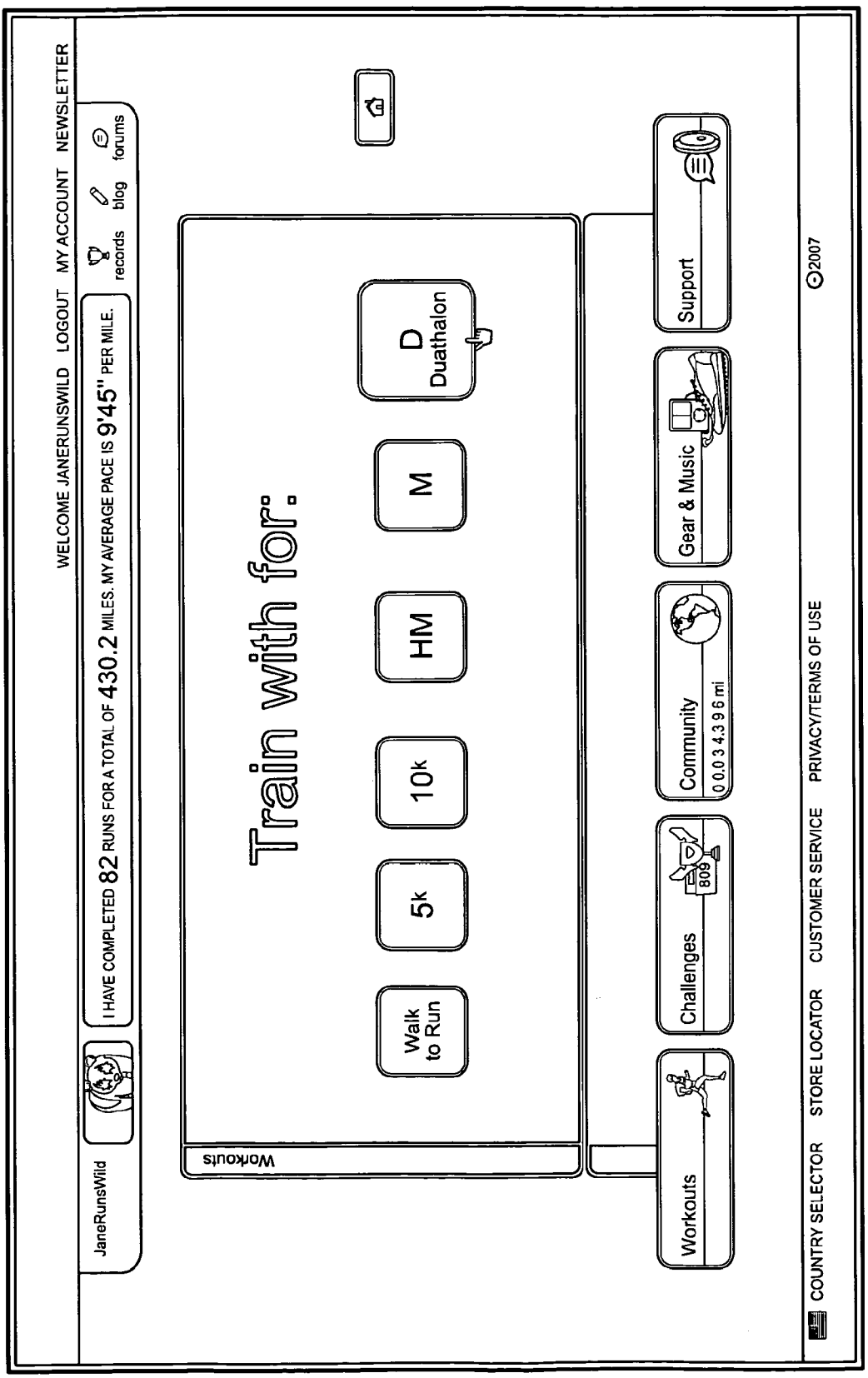
FIG. 38 illustrates an example user interface for creating a training program according to one or more aspects described herein.
Figure 39:
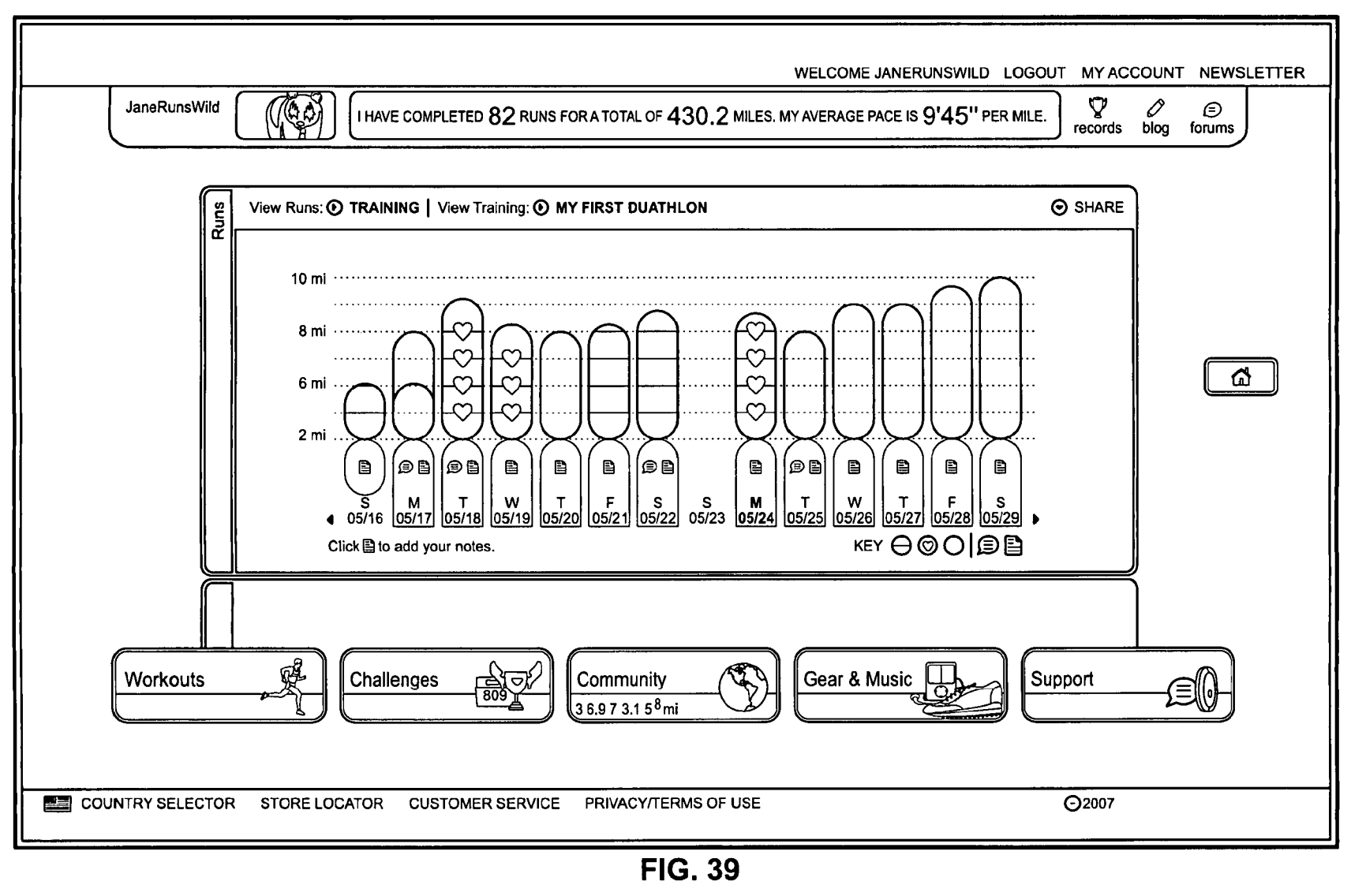

FIGS. 38 and 39 illustrate that the user interface 2400 may also serve as an athletic training tool and/or athletic training log such as described by U.S. Provisional Patent Application 61/032,018, filed Feb. 27, 2008. For example, a user or athlete may select a training program to train for walk-to-run, five kilometers, ten kilometers, a half marathon, and/or a marathon. Further, the user or athlete may train for a duathalon. More specifically, and as illustrated by FIG. 39, a duathalon may include actual run distance and equivalent cardiovascular distance components. Alternatively, a user or athlete may complete the training program with any combination of actual distance run or equivalent cardiovascular distance based on other athletic performance activity.

Training programs may be defined in a variety of ways and may include equipment specific tasks. For example, a training program may specify that 2 miles are to be walked on a treadmill on day one, while 3 miles are to be biked on a bicycle on day two. Training programs may thus record the type of machine on which athletic activity was performed. The use of different machines may aid in training different skills or athletic abilities in reaching an overall goal such as a triathlon or marathon. Training programs may be directed to an individual or may be defined for a group of people. Solo training programs may guide individuals in performing a single athletic activity or multiple types of athletic activity. The training program and the user's progress in reaching a specified goal may be shared with other users, friends, family, trainers, coaches and the like.

Figure 40:
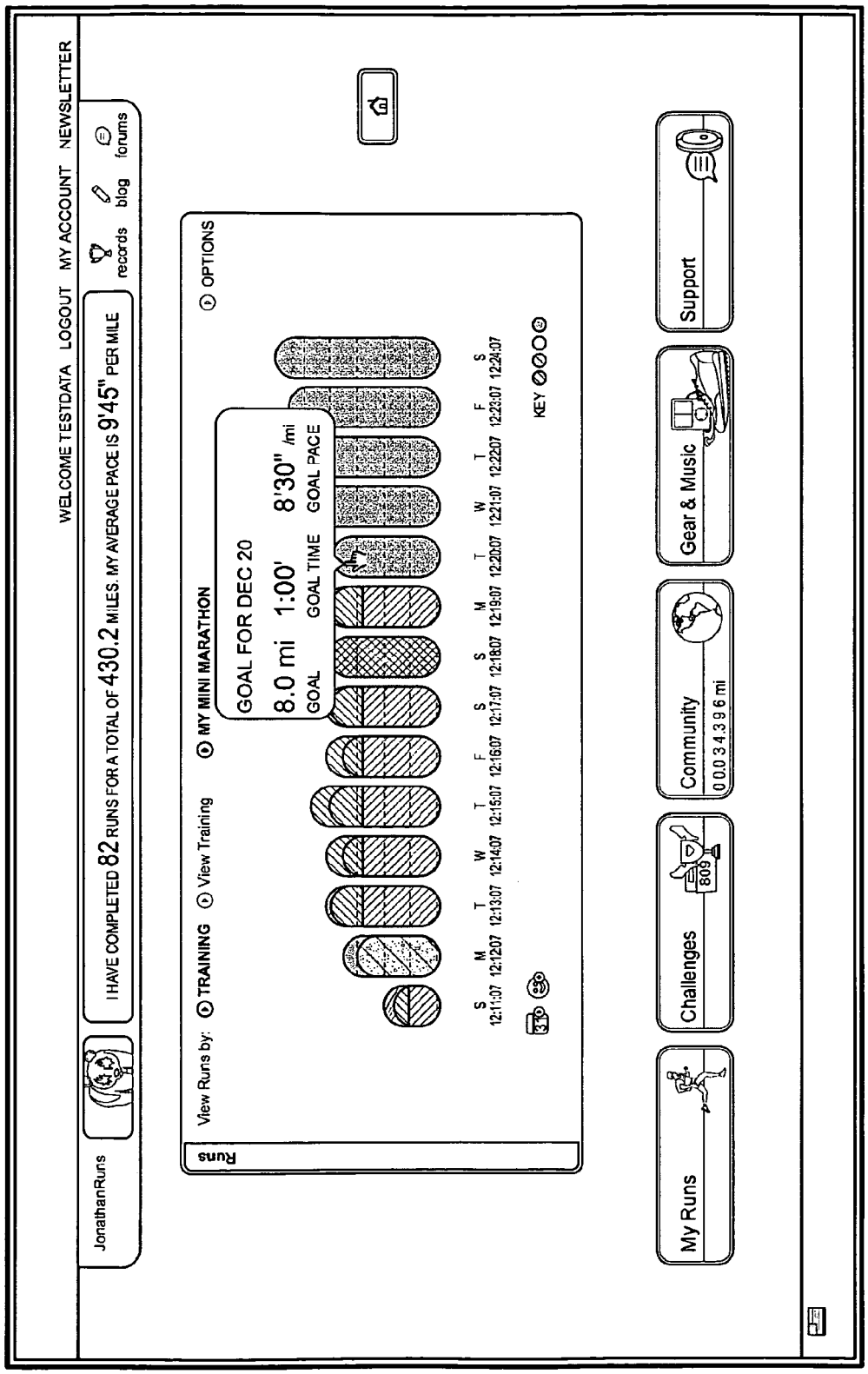
FIG. 40 illustrates an example training program interface displaying a series of objectives for reaching a specified goal according to one or more aspects described herein.

FIG. 40 illustrates a tracking interface for reaching a specified goal. For example, the user may set a goal to run a marathon in a desired amount of time (e.g., marathon in 5 hours) by a specified date. Accordingly, the training program may include a series of runs of increasing distance to help the user achieve his or her specified goal. Passed runs may be displayed with the goal or objective for that run as well as the actual miles run. Hovering or otherwise interacting with one of the goals or objectives shows the user the goal for that particular run or day. For December 20, for example, the goal is to run 8 miles in 1 hour. Interface 4000 may be provided on a console of an athletic training device (e.g., elliptical, rowing machine, bicycle, treadmill), on an athletic training network site and/or on a portable user device.

Group training may share features similar to those of solo training, but instead of a single user following the training program, multiple users may be participating in the training program based on the same schedule. A trainer, for example, may thus track the progress of the overall group to identify how the group is doing in terms of achieving each task and progressing toward a goal as well as how each individual member is performing and contributing to the group's overall goal. A trainer may issue comments and suggestions to all members of the group or may provide user-specific comments that only the user to which the comments are directed can view. Whether solo or group, training programs may be edited and adjusted according to user needs. For example, if a user cannot workout on Friday, Saturday and Sunday's planned workout may be increased to compensate for the lack of athletic activity on Friday. In another example, a trainer may edit a type of athletic activity to be performed if the trainer believes that a trainee is lacking a particular athletic ability such as endurance or speed.

In one or more arrangements, athletic activity may be tracked using electronic avatars. Generally speaking, an avatar may be a graphical two-dimensional icon or a 3-dimensional model that may represent a user. An avatar may be as simple as a picture of the user or may be a graphical object that may represent the user's actions, beliefs, interests, appearance, identity, personality, and the like. An avatar may be further animated. Avatars are further described in U.S. application Ser. No. 12/324,140, entitled "INTERACTIVE AVATAR FOR SOCIAL NETWORK SERVICES," and filed Nov. 26, 2008, the content of which is hereby incorporated by reference in its entirety.

In one or more arrangements, avatars or avatar appearance may further be athletic equipment specific. For example, a user may want to specify different avatars for a treadmill and an elliptical machine. In another example, a user may want to use the same avatar, but wearing different clothing for different athletic equipment. In one or more arrangements, an avatar may exist on a user's portable device, on athletic equipment, on a network site or combinations thereof. For example, when a user is working out on a treadmill, a user interface of the treadmill may display the user's avatar. The treadmill may receive avatar information from the user's portable device or from an athletic performance tracking site.

Various attributes of the avatar may change based on a user's athletic activity to provide motivation and encouragement. For example, new clothes or shoes may be made available to the user's avatar if the user reaches certain goals. In another example, an avatar may grow bigger or appear more muscular upon the user achieving various goals. In one or more arrangements, avatar rewards (e.g., shoes, t-shirts) may be specific to a gym provider, a gym location and/or to classes or programs within a gym. According to another aspect, avatar rewards may be defined by other users to help motivate a team member or friend.

Figure 41:
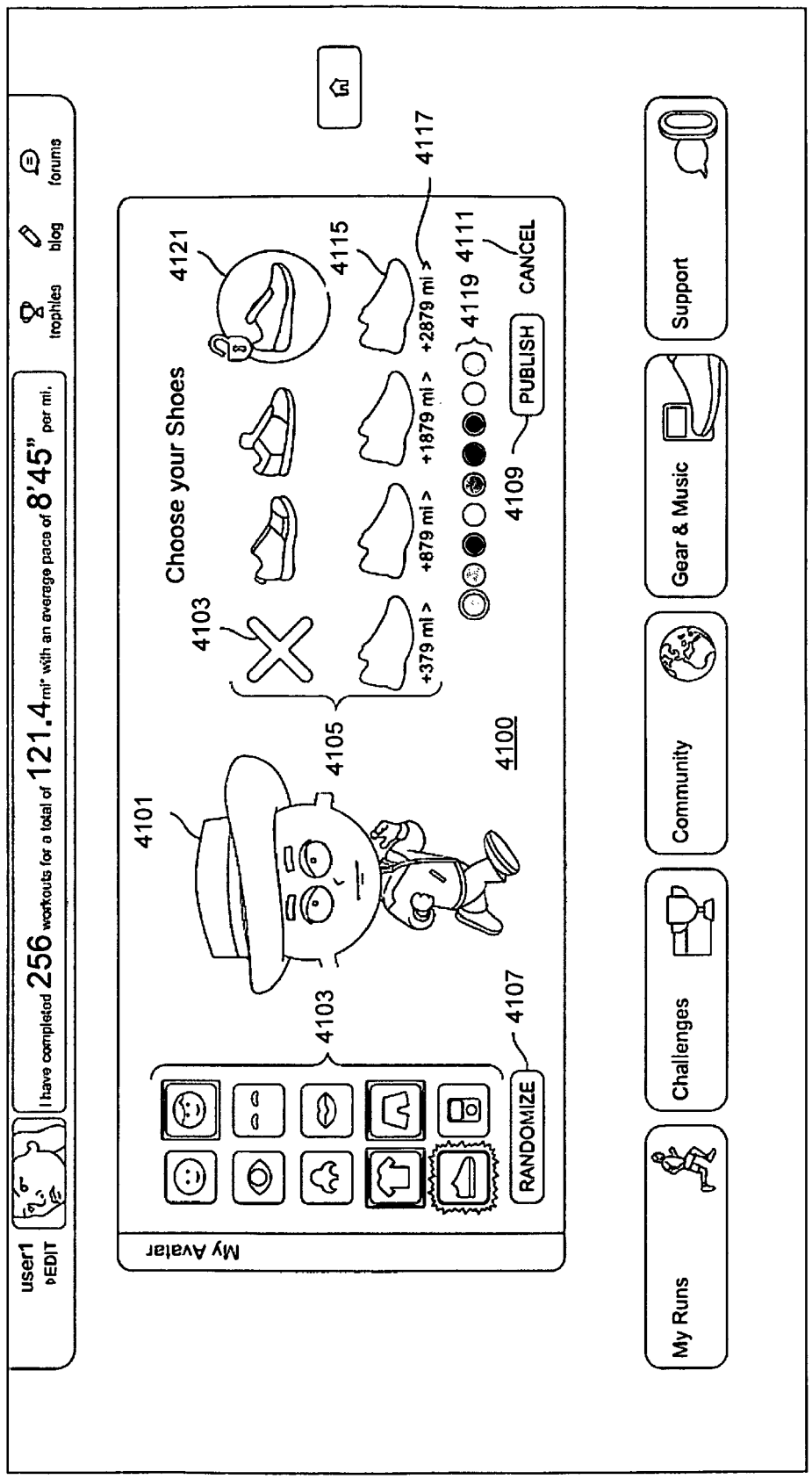
FIG. 41 illustrates an example avatar customization interface according to one or more aspects described herein.

FIG. 41 illustrates an example avatar customization interface through which a user may create a new avatar. Avatar creation interface 4100 may initially display a default avatar 4101, feature categories 4103, specific features 4105, a randomize option 4107, a publish option 4109 and a cancel option 4111. Starting from default avatar 4101, a user may modify various characteristics such as hair style or color, facial expression, lips, eye brows, eyes, nose, shirt, pants, shoes and accessories. Although not illustrated, other characteristics may also be modifiable. For example, in some embodiments, an avatar's body shape, ears and hands may be customized. Using categories 4103, each of the above mentioned characteristics may be customized according to the user's preference. In one example, and as illustrated, a user may modify the shoes that avatar 4101 is wearing. In particular, specific features 4105 include a variety of shoes that are available to the user for his or her avatar. In some instances, new shoes or other features might only be available upon completion of a certain challenge, action, goal or the like. The shoes available for the avatar could also correspond to a latest actual shoe model offered by a shoe manufacturer or some other shoe design currently in fashion among users. The unavailable shoes 4115 or other feature might be shown in a dark outline (i.e., without significant details) along with the goal 4117 that needs be met. For example, some shoes might not be available for selection until a user has run a specified distance. A user may further select the 'X' option 4113 if he or she wishes to remove shoes from avatar 4101. Additionally, a user may select a color of the shoe or other feature being customized using color palette 4119. An unlocked lock symbol 4121 next to or otherwise associated with a selectable feature may indicate that the selectable feature is newly available to the user. Interface 4100 may be access through a console of an athletic training device (e.g., elliptical, rowing machine, bicycle, treadmill), an athletic training network site and/or a portable user device.

In a group or challenge setting, multiple avatars may be displayed in an interface to illustrate the progress of each user in the group or challenge. For example, if two users are competing for a 10-miles run goal, a user interface may display both avatars in relative position to one another based on how far each user has actually run. This may help motivate users to close the gap if they are behind and to further increase a lead if they are leading in the challenge. In another example, if two users are teammates trying to achieve a common goal, a first user may send a reward or words of encouragement to a second user if the first user sees, via the avatars, that the second user is falling behind in training. Users may view performance information by hovering over or otherwise interacting with an avatar. Users may also share or otherwise publish their avatar to other users or the general public to show their athletic progress.

Depending on a location or circumstance, users may be able to view other users' avatars. For example, if a user is in a spinning class, avatars for all members of the class may be shared with the class. Alternatively, avatars of treadmill runners in a gym may be shared with all other treadmill runners. Users may elect to participate in avatar and athletic performance information sharing or may set their athletic information to private. The sharing of avatars and associated athletic performance data may encourage or motivate users.

Data collected by athletic performance tracking sites or by athletic equipment may be shared locally (e.g., at that machine) or across locations. For example, athletic data may be shared by all machines in a particular gym location or across all gym locations of a gym provider. In another example, data collected in the past 24 hours (or some other time frame) may be used as comparison data for a current user. That is, a user may be able to compare his or her current athletic activity to an average of athletic activity performed in the past 24 hours by other users. Athletic data may further be shared across gym locations of different gym providers. In one arrangement, an athletic performance tracking site may receive athletic performance data from one or more gym locations. The athletic performance tracking site may be configured to filter the received data and sort the information based on location, gym provider, user, athletic equipment used and/or combinations thereof. Once filtered, data may then be transmitted to various locations. For example, all data for a gym provider may be sent to all locations of that gym provider. In another example, data for spinning classes for all gym providers may be shared. Alternatively or additionally, gym locations or gym providers may collect their own data, e.g., in a back office system, and filter what is to be shared with other gym locations or providers.

Conclusion

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

What is claimed is:

1. An apparatus comprising:
   an athletic performance module configured to:
      detect athletic activity of a user;
      classify the detected athletic activity into one of a plurality of athletic activity categories based on at least one characteristic of the detected athletic activity; and
      identifying an athletic activity data set exhibiting a best value for an athletic activity metric among a plurality of athletic activity data sets categorized in the one of the plurality of athletic activity categories; and
   a display configured to display a user interface comprising:
      an athletic performance data section providing athletic activity information associated with the detected athletic activity of the user; and
      a message section providing one or more messages to the user, wherein the one or more messages provide a comparison between the athletic activity information and the identified athletic activity data set.

2. The apparatus of claim 1, wherein the one or more messages includes a comment from at least one other user received through a data network from another apparatus.

3. The apparatus of claim 1, wherein the user interface further includes an avatar display section for displaying an electronic avatar representing the user.

4. The apparatus of claim 3, wherein an appearance of the electronic avatar changes based on the athletic activity of the user.

5. The apparatus of claim 1, wherein the athletic activity information includes a measure of the athletic activity of the user in a common unit.

6. The apparatus of claim 5, wherein the athletic activity information is provided in the common unit and a unit in which the athletic activity is measured.

7. The apparatus of claim 6, wherein the user interface is configured to provide the athletic activity information in the common unit in a perceptively different manner than the unit in which the athletic activity is measured.

8. The apparatus of claim 1, wherein the display is further configured to display athletic activity information of at least one other user.

9. The apparatus of claim 8, wherein the display is configured to display athletic activity information of at least one other user in comparison with the athletic activity of the user.

10. The apparatus of claim 1, wherein the message section is configured to provide the one or more messages to the user upon the user reaching a halfway mark to a specified goal.

11. The apparatus of claim 1, wherein the one or more messages include a message of encouragement.

12. The apparatus of claim 1, wherein the user interface further includes a history section configured to display historical workout information of the user.

13. The apparatus of claim 12, wherein the athletic performance module is further configured to:
select the historical workout information from a plurality of historical workout information based on a type of the athletic activity detected, wherein the plurality of historical workout information includes workout information corresponding to a plurality of athletic activity types.

14. The apparatus of claim 1, wherein each of the plurality of athletic activity categories corresponds to a different distance over which athletic activity is performed.

15. The apparatus of claim 1, wherein the one or more messages are provided to the user in response to determining that the user is on track to beat the identified athletic activity data set, wherein the determination is made based on the comparing of the athletic activity detected by the athletic performance module and the identified athletic activity data set.

16. The apparatus of claim 1, wherein the apparatus corresponds to an athletic performance device comprising:
a first portion configured to remain stationary during performance of the athletic activity by the user using the athletic performance device; and
a second portion comprising one or more moveable mechanical devices through which the user performs the athletic activity.

17. A non-transitory computer readable storage medium storing computer readable instructions that, when executed, cause an apparatus to:
detect athletic activity of a user;
classify the detected athletic activity into one of a plurality of athletic activity categories based on at least one characteristic of the detected athletic activity; and
identifying an athletic activity data set exhibiting a best value for an athletic activity metric from a plurality of athletic activity data sets categorized in the one of the plurality of athletic activity categories; and
generate a user interface comprising:
an athletic performance data section providing athletic activity information associated with the detected athletic activity of the user; and
a message section providing one or more messages to the user, wherein the one or more messages provide a comparison between the athletic activity information and the identified athletic activity data set.

* * * * *